(12) United States Patent
Laga et al.

(10) Patent No.: US 10,619,165 B2
(45) Date of Patent: Apr. 14, 2020

(54) ***BRASSICA* PLANT COMPRISING A MUTANT INDEHISCENT ALLELE**

(71) Applicant: BASF AGRICULTURAL SOLUTIONS SEED, US LLC, Research Triangle Park, NC (US)

(72) Inventors: Benjamin Laga, Wingene (BE); Bart Den Boer, Merelbeke (BE); Bart Lambert, Ypres (BE)

(73) Assignee: BASF AGRICULTURAL SOLUTIONS SEED, US LLC, Research Triangle Park, NC (US)

( * ) Notice: Subject to any disclaimer, the term of this patent is extended or adjusted under 35 U.S.C. 154(b) by 1376 days.

(21) Appl. No.: 14/328,337

(22) Filed: Jul. 10, 2014

(65) Prior Publication Data

US 2014/0351967 A1 Nov. 27, 2014

Related U.S. Application Data

(63) Continuation of application No. 13/003,364, filed as application No. PCT/EP2009/005004 on Jul. 9, 2009, now Pat. No. 8,809,635.

(60) Provisional application No. 61/135,230, filed on Jul. 17, 2008.

(30) Foreign Application Priority Data

Jul. 18, 2008 (EP) ..................................... 08075648

(51) Int. Cl.
 *C12N 15/82* (2006.01)
 *C07K 14/415* (2006.01)

(52) U.S. Cl.
 CPC ........ *C12N 15/8266* (2013.01); *C07K 14/415* (2013.01)

(58) Field of Classification Search
 None
 See application file for complete search history.

(56) References Cited

U.S. PATENT DOCUMENTS

| 5,985,557 A | 11/1999 | Prudent et al. |
| 6,001,567 A | 12/1999 | Brow et al. |
| 2005/0120417 A1 * | 6/2005 | Yanofsky ............. C07K 14/415 800/287 |
| 2007/0006336 A1 | 1/2007 | Yanofsky et al. |
| 2007/0136893 A1 | 6/2007 | Yanofsky et al. |

FOREIGN PATENT DOCUMENTS

| EP | 0534858 | 3/1993 |
| WO | WO 97/13865 | 4/1997 |
| WO | WO 99/00503 | 1/1999 |
| WO | WO 01/59122 | 8/2001 |
| WO | WO 01/79517 | 10/2001 |
| WO | WO 2004/113542 | 12/2004 |
| WO | WO-2004113542 A1 * | 12/2004 ........... C07K 14/415 |
| WO | WO 2006/009649 | 1/2006 |
| WO | WO 2009/068313 | 6/2009 |

OTHER PUBLICATIONS

Barker, Guy C. et al., "Novel Insights into Seed Fatty Acid Synthesis and Modification Pathways from Genetic Diversity and Quantitative Trait Loci Analysis of the *Brassica* C Genome", Plant Physiology, Aug. 2007, vol. 144, pp. 1827-1842.
Bruce, D. M. et al., "Threshability of Shatter-resistant Seed Pods in Oilseed Rape", J. Agric. Engng Res., 2001, vol. 80, No. 4, pp. 343-350.
Bruce, D. M. et al., "Determining the Oilseed Rape Pod Strength Needed to Reduce Seed Loss due to Pod Shatter", Biosystems Engineering, 2002, vol. 81, No. 2, pp. 179-184.
Child, Robin et al., "Ethylene biosynthesis in oilseed rape pods in relation to pod shatter", J. of Experimental Botany, May 1998, vol. 49, No. 322, pp. 829-838.
Child, R. D. et al., "Increased resistance to pod shatter is associated with changes in the vascular structure in pods of a resynthesized *Brassica napus* line", Journal of Experimental Botany, Aug. 2003, vol. 54, No. 389, pp. 1919-1930.
Child, Robin et al., "Anatomical variation in the dehiscence zone of oilseed rape pods and its relevance to pod shatter", 1999, Proc 10th Int. Rapeseed Congress.
Davies, G. C. et al., "Fracture mechanics of oilseed rape pods", Journal of Materials Science, 1997, vol. 32, pp. 5895-5899.
Dinneny, Jose R. et al., "The role of JAGGED in shaping lateral organs", Development 131, 2004, pp. 1101-1110.
Dinneny, Jose R. et al., "A genetic framework for fruit patterning in *Arabidopsis thaliana*", Development 132, 2005, pp. 4687-4696.
Ferrandiz, Cristina et al., "Negative Regulation of the Shatterproof Genes by Fruitfull During *Arabidopsis* Fruit Development", Science, 2000, vol. 289, pp. 436-438.
Gu, Qing et al., "The Fruitfull MADS-box gene mediates cell differentiation during *Arabidopsis* fruit development", Development 125, 1998, pp. 1509-1517.
Heim, Marc A. et al., "The Basic Helix-Loop-Helix Transcription Factor Family in Plants: A Genome-Wide Study of Protein Structure and Functional Diversity", Mol. Bioi. Evol., 2003, vol. 20, No. 5, pp. 735-747.
Henikoff, Steven et al., "TILLING. Traditional Mutagenesis Meets Functional Genomics", Plant Physiology, Jun. 2004, vol. 135, pp. 630-636.
Kadkol, G. P. et al., "Anatomical Basis of Shatter-resistance in the Oilseed *Brassicas*", Aust. J. Bot., 1986, vol. 34, pp. 595-601.
Li, Xin et al., "Reverse genetics by fast neutron mutagenesis in higher plants", Funct. lntegr. Genomics, 2002, vol. 2, pp. 254-258.
Li, Xin et al., "A fast neutron deletion mutagenesis-based reverse genetics system for plants", The Plant Journal, 2001, vol. 27, No. 3, pp. 235-242.

(Continued)

*Primary Examiner* — Charles Logsdon
(74) *Attorney, Agent, or Firm* — Arent Fox LLP

(57) ABSTRACT

This invention relates to crop plants of which the fruit dehiscence properties are modulated. More specifically the invention relates to improved methods and means for reducing seed shattering, or delaying seed shattering until after harvest, while maintaining at the same time an agronomically relevant treshability of the pods, and for increasing yield.

18 Claims, No Drawings
Specification includes a Sequence Listing.

(56) References Cited

OTHER PUBLICATIONS

Liljegren, Sarah J. et al., "Shatterproof MADS-box genes control seed dispersal in *Arabidopsis*", Apr. 13, 2000, Nature, vol. 404, pp. 766-770.
Liljegren, Sarah J. et al., "Control of Fruit Patterning in *Arabidopsis* by Indehiscent", Cell, Mar. 19, 2004, vol. 116, pp. 843-853.
Lysak Martin A. et al., "Chromosome triplication found across the tribe Brassiceae", Genome Research, 2005, vol. 15, pp. 516-525
MacLeod, John, "Harvesting", Harvesting in Oilseed Rape, pp. 107-119, published 1981.
Mandel, M. Alejandra et al., "The *Arabidopsis* AGL8 MADS Box Gene is Expressed in Inflorescence Meristems and is Negatively Regulated by APETALA1", The Plant Cell, Nov. 1995, vol. 7, pp. 1763-1771.
McCallum, Claire M. et al., "Targeted screening for induced mutations", Nature Biotechnology, Apr. 2000, vol. 18, pp. 455-457.
McCallum, Claire M. et al., "Targeting Induced Local Lesions in Genomes (TILLING) for Plant Functional Genomics", Plant Physiology, Jun. 2000, vol. 123, pp. 439-442.
Meakin, Paul J. et al., "Dehiscence of Fruit in Oilseed Rape (*Brassica napus* L.)", Journal of Experimental Botany, Aug. 1990, vol. 41, No. 229, pp. 995-1002.
Morgan, C. L. et al., "Genetic variation for pod shatter resistance among lines of oilseed rape developed from synthetic *B. napus*", Field Crops Research, 1998, vol. 58, pp. 153-165.
Murre, Cornelis et al., "A New DNA Binding and Dimerization Motif in Immunoglobulin Enhancer Binding, daughterless, MyoD, and myc Proteins", Cell, Mar. 10, 1989, vol. 56, pp. 777-783.
Needleman, Saul B. et al., "A General Method Applicable to the Search for Similarities in the Amino Acid Sequence of Two Proteins", J. Mol. Bioi., 1970, vol. 48, pp. 443-453.
Ohno, Carolyn K. et al., "The *Arabidopsis* JAGGED gene encodes a zinc finger protein that promotes leaf tissue development", Development 131, 2004, pp. 1111-1122.
Petersen, Morten et al., "Isolation and characterisation of a pod dehiscence zone-specific polygalacturonase from *Brassica napus*", Plant Molecular Biology, 1996, vol. 31, pp. 517-527.
Prakash et al., Plant Breeding 101, 1988, pp. 167-168.
Prakash et al., "Reconstruction of allopolyploid *Brassicas* through non-homologous recombination: introgression of resistance to pod shatter in *Brassica napus*", Genetical Research, 1990, vol. 56, pp. 1-2.
Ptashne, Mark, "How eukaryotic transcriptional activators work", Nature, Oct. 1988, vol. 225, pp. 683-689.
Quong, Melanie W. et al., "A New Transcriptional-Activation Motif Restricted to a Class of Helix-Loop-Helix Proteins is Functionally Conserved in Both Yeast and Mammalian Cells", Molecular and Cellular Biology, Feb. 1993, vol. 13, No. 2, pp. 792-800
Rajani, Sarojam et al., "The *Arabidopsis* myc/bHLH gene ALCATRAZ enables cell separation in fruit dehiscence", Current Biology, 2001, vol. 11, pp. 1914-1922.
Rice, Peter et al., "EMBOSS: The European Molecular Biology Open Software Suite", Trends in Genetics, 2000, vol. 16, No. 6, pp. 276-277.
Roeder, Adrienne H. K. et al., "The Role of the Replumless Homeodomain Protein in Patterning the *Arabidopsis* Fruit", Current Biology, Sep. 16, 2003, vol. 13, pp. 1630-1635.
Sawa, Shinichiro et al, "Filamentous Flower, a meristem and organ identity gene of *Arabidopsis*, encodes a protein with a zinc finger and HMB-related domains", Genes Dev., 1999, vol. 13, pp. 1079-1088.
Siegfried, Kellee R. et al., "Members of the YABBY gene family specify abaxial cell fate in *Arabidopsis*", Development 126, 1999, pp. 4117-4128.
Spence, J. et al, "Pod Shatter in *Arabidopsis thaliana, Brassica napus* and *B. juncea*", Journal of Microscopy, Feb. 1996, vol. 181, pt. 2, pp. 195-203.
Toledo-Ortiz, Gabriela et al, "The *Arabidopsis* Basic/Helix-Loop-Helix Transcription Factor Family", The Plant Cell, Aug. 2003, vol. 15, pp. 1749-1770.
Vancanneyt, Guy et al, "Podshatter Resistance: Exploitation of *Arabidopsis* genes to develop a productivity trait in Oilseed Rape", XIII International Conference on *Arabidopsis* Research, Sevilla, Spain, Jun. 28-Jul. 2, 2002.
Vos, Pieter et al, "AFLP: a new technique for DNA fingerprinting", Nucleic Acids Research, 1995, vol. 23, No. 21, pp. 4407-4414.
Wu, Hong et al, "The Indehiscent protein regulates unequal cell divisions in *Arabidopsis* fruit", Planta, 2006, vol. 224, pp. 971-979.

\* cited by examiner

BRASSICA PLANT COMPRISING A MUTANT INDEHISCENT ALLELE

CROSS-REFERENCE TO RELATED APPLICATIONS

This application is a continuation of U.S. application Ser. No. 13/003,364, filed Jun. 29, 2011, now U.S. Pat. No. 8,809,635, issued on Aug. 19, 2014. U.S. application Ser. No. 13/003,364 is a National Phase application of International Patent Application No. PCT/EP2009/005004, filed Jul. 9, 2009, which claims the benefit of priority from U.S. Provisional Application No. 61/135,230, filed Jul. 17, 2008 and European Application No. 08075648.9, filed Jul. 18, 2008, the contents of each are hereby incorporated by reference in their entireties.

FIELD OF THE INVENTION

This invention relates to the field of agriculture, more specifically to the use of molecular biology techniques to alter dehiscent seed plants, particularly of the Brassicaceae family, in particular *Brassica* species, and/or accelerate breeding of such dehiscent seed plants. More specifically the invention relates to improved methods and means for reducing seed shattering, or delaying seed shattering until after harvest, in plants such as Brassicaceae plants, particularly Brassicaceae plants grown for seed production, while maintaining at the same time an agronomically relevant treshability of the pods. Methods are also provided to identify molecular markers associated with reduced or delayed seed shattering in a population of dehiscent seed plants. Also provided are methods and means to increase the yield, particularly grain and seed yield. The yield increase phenotype may be separate from the reduced or delayed seed shatter phenotype.

BACKGROUND OF THE INVENTION

Siliques or pods from *Brassica* plants release their seeds through a process called fruit dehiscence. A silique consists of two carpels joined margin to margin. The suture between the margins forms a thick rib, called replum. As pod maturity approaches, the two valves separate progressively from the replum, along designated lines of weakness in the pod, eventually resulting in the shattering of the seeds that were attached to the replum. The dehiscence zone defines the exact location of the valve dissociation.

Shedding of seed (also referred to as "seed shatter" or "pod shatter") by mature pods before or during crop harvest is a universal phenomenon with crops that develop dry dehiscent fruits. Premature seed shatter results in a reduced seed recovery, which represents a problem in crops that are grown primarily for the seeds, such as oil-producing *Brassica* plants, particularly oilseed rape. Another problem related to premature seed shattering is an increase in volunteer growth in the subsequent crop year. In oilseed rape, pod shatter-related yield losses are on average 20% (Child et al., 1998, J Exp Bot 49: 829-838), but can reach up to 50%, depending on the weather conditions (MacLeod, 1981, Harvesting in Oilseed Rape, pp. 107-120, Cambridge Agricultural Publishing, Cambridge).

Current commercial oilseed rape varieties are extremely susceptible to shattering. There is little variation for resistance to shattering within existing breeding programs of *B. napus* but resistant lines have been found within the diploid parents of *B. napus* (*B. oleracea* and *B. rapa*) as well as within other members of the *Brassica* genus, notably *B. juncea*, *B. carinata* and *B. nigra*. Kadkol et al. (1986, Aust. J. Botany 34 (5): 595-601) report increased resistance towards shattering in certain accessions of *B. campestris* that was associated with the absence of a separation layer in the region of attachment of the siliqua valves to the replum. Prakash and Chopra (1988, Plant breeding 101: 167-168) describe the introgression of resistance to shattering in *Brassica napus* from *Brassica juncea* through non-homologous recombination. Spence et al. (1996, J of Microscopy 181: 195-203) describe that some lines of *Brassica juncea* show a reduced tendency to shatter as compared to *Brassica napus* lines. Morgan et al., 1998 (Fields Crop Research 58, 153-165) describe genetic variation for pod shatter resistance among lines of oilseed rape developed from synthetic *B. napus* and conclude that lines which required much energy to open their pods appeared to have increased vascularisation in the dehiscence zone and to have reduced cell wall degradation within the dehiscence zone. They further found a significant negative correlation between the length of the pod beak and the force needed to cause pod shattering. Child and Huttly (1999, Proc 10th Int. Rapeseed Congress) describe variation in pod maturation in an irradiation-induced mutant *B. napus* and a population of its parent cultivar, Jet Neuf, wherein the most resistant wild-type and mutant plants showed much lignification of groups of cells throughout the dehiscence zone and wherein vascular traces situated close to the inner edge of the dehiscence zone in the mutant were described to help to secure the valves. Child et al. (2003, J Exp Botany 54 (389): 1919-1930) further describe the association between increased pod shatter resistance and changes in the vascular structure in pods of a resynthesized *Brassica napus* line. However, the traditional methods for breeding have been unsuccessful in introducing shatter resistance into rape cultivars, without interference with other desirable traits such as early flowering, maturity and blackleg resistance (Prakash and Chopra, 1990, Genetical Research 56: 1-2).

Several genes, which promote or inhibit pod dehiscence, have been identified in *Arabidopsis thaliana* through mutant analysis: Combined mutants in both SHATTERPROOF1 (SHP1; initially referred to as AGL1) and SHATTERPROOF2 (SHP2; initially referred to as AGL5) result in indehiscent siliques (i.e. siliques which remain closed upon maturity in *Arabidopsis thaliana*) (Liljegren et al., 2000, Nature 404, 766-770). Similarly, mutants in the INDEHISCENT gene (referred to as IND1) in *Arabidopsis thaliana* (Liljegren et al., 2004, Cell 116: 843-853; PCT publication WO 01/79517), as well as in ALCATRAZ (referred to as ALC; Rajani et al. 2001, Current Biology 11, 1914-1922) interfered with pod dehiscence leading to pod shatter resistance. Constitutive expression of FRUITFUL (FUL), a repressor of SHP and IND, in *Arabidopsis thaliana* also resulted in indehiscent siliques (Ferrandiz et al., 2000, Science, 289, 436-438). These transcription factors are believed to form a non-linear transcriptional network that controls valve margin identity and pod shatter. Liljegren et al. (2004, Cell 116: 843-853) further describe that IND, an atypical basic helix-loop-helix (bHLH) gene, directs the differentiation of the valve margin into the separation and lignified layers in *Arabidopsis thaliana*. The layer of lignified cells adjacent to the separation layer along with the endocarp b layer (a single lignified cell layer in each valve) produce a spring-like tension within the drying fruit that contributes to its opening. Lignification of the valve endodocarp b layer requires the activities of IND, SHP, ALC, and FUL, a MADS-domain transcription factor that is expressed throughout the valves (Liljegren et al., 2004, supra; Mandel and Yanofsky, 1995, Plant Cell 7, 1763-1771). FUL and REPLUMLESS (RPL), a homeodomain transcription factor that is expressed in the replum (Roeder et al., 2003, Curr Biol 13, 1630-1635), have been found to set the boundaries of the genes that confer valve margin identity (Gu et al., 1998, Development 125, 1509-1517; Ferrandiz et al., 2000, Science, 289, 436-438; Roeder et al., 2003, supra). Finally, FILAMENTOUS FLOWER (FIL) and YABBY3 (YAB3), two YABBY-family transcription factors (Sawa et al., 1999, Genes Dev 13, 1079-1088; Siegfried et al., 1999, Development 126, 4117-4128), and JAGGED (JAG), a C2H2 zinc-finger transcription factor (Dinneny et al., 2004, Development 131, 1101-1110; Ohno et al., 2004, Development 131, 1111-1122), were identified to redundantly contribute to proper valve and valve margin development by promoting the expression of FUL and SHP in a region-specific manner (Dinneny et al., 2005, Development 132, 4687-4696). Genes for a number of hydrolytic enzymes, such as endopolygalacturonases, which play a role, during pod dehiscence, in the programmed breakdown of the dehiscence zone in pods from *Brassica* plants have also been identified (see e.g. WO 97/13865; Petersen et al., Plant. Mol. Biol., 1996, 31:517-527).

Liljegren et al. (2004, Cell 116: 843-853) describe five mutant alleles of *Arabidopsis* IND. The lignified cells in the dehiscence zone are either absent or present in plants comprising these mutant alleles depending on the severity of the mutations (severe ind mutants do not contain lignified cells in the region corresponding to the inner part of the valve margin in wild-type plants), but in all cases the silique is indehiscent. Wu et al. (2006), Planta 224, 971-979) describe a sixth mutant allele of *Arabidopsis* IND. Plants comprising this mutant allele show no lignified cells at the junctions of the valve margin and the replum, contain fewer cells in a region of seven layers of cells, which appeared to encompass the commonly known dehiscence zone and replum border in wild-type plants, and exhibit incomplete cytokinesis in this layer.

US 2005/0120417 and US 2007/0006336 describe the identification and isolation of two IND1 orthologs from *Brassica napus*.

WO99/00503, WO01/79517 and WO0159122 describe down-regulation of the expression of the *Arabidopsis* ALC, IND, AGL1 and AGL5 genes and orthologs thereof using gene-silencing techniques (such as antisense suppression or cosuppression) and mutagenesis.

Vancanneyt et al., 2002 (XIII International Conference on *Arabidopsis* Research, Sevilla, Spain Jun. 28-Jul. 2; 2002) reported that the expression of FUL from *A. thaliana* under control of a CaMV 35S promoter in oilseed rape resulted in a number of pod shatter resistant transformants. Pods of such pod shatter resistant lines had no dehiscence zone, and opening of the pods could only be achieved by random fracture of the valves by applying considerable pressure.

Vancanneyt et al., 2002 (XIII International Conference on *Arabidopsis* Research, Sevilla, Spain Jun. 28-Jul. 2; 2002) also reported that silencing of the IND gene in *Arabidopsis thaliana* using so-called dsRNA silencing techniques resulted in almost complete pod shatter resistance. Ninety-eight percent of the transgenic *Arabidopsis* lines developed siliques, which did not open along the valve suture, and could only be opened by applying considerable pressure to the valves.

It is important to realize that while seed shattering constitutes an important problem in oilseed rape culture, which may be solved by developing pod shatter resistant lines, ultimately, separation of the seeds from the pods is still required. In normal agricultural practice this is achieved by treshing of the pods by a combine harvester. Treshing of the pods by a combine harvester must be complete and must cause minimum damage to the seeds thus released. However, as pod strength increases, the more severe action required to tresh them causes an unacceptable level of damage to the seed. The pods of pod shatter resistant Brassicaceae plants should thus not be so strong that they cannot be treshed in a combine harvester (Bruce et al. 2001, J. Agric. Engng Res. 80, 343-350).

WO 2004/113542 describes that moderate dsRNA gene silencing of genes involved in the development of the dehiscence zone and valve margins of pods in Brassicaceae plants allows the isolation of transgenic lines with increased pod shatter resistance and reduced seed shattering, the pods of which however may still be opened along the dehiscence zone by applying limited physical forces.

WO09/068313 (claiming priority of European patent application EP 07023052) discloses *Brassica* plants comprising at least two IND genes, in particular *Brassica napus* plants, characterized in that they comprise three full knock-out mutant IND alleles in their genome and wherein the pod shatter resistance of the plants is significantly increased compared to the pod shatter resistance of a plant not comprising mutant IND alleles, but wherein the plant preferably maintains an agronomically relevant treshability of the pods.

The inventions described hereinafter in the different embodiments, examples and claims provide further improved methods and means for modulating dehiscence properties in dehiscent seed plants. More specifically, the present invention describes further improved methods and means for reducing seed shattering, or delaying seed shattering until after harvest, in plants such as Brassicaceae plants, particularly Brassicaceae plants grown for seed production, while maintaining at the same time an agronomically relevant treshability of the pods. In particular, the present application discloses *Brassica* plants comprising at least two IND genes, in particular *Brassica napus* plants, characterized in that they comprise two partial knock-out mutant IND alleles in their genome or two partial and two full knock-out mutant IND alleles and wherein the pod shatter resistance of the plants is significantly increased compared to the pod shatter resistance of a plant not comprising mutant IND alleles, but wherein the plant preferably maintains an agronomically relevant treshability of the pods. Also provided are methods and means to increase the yield, particularly grain and seed yield. The yield increase phenotype may be separate from the reduced or delayed seed shatter phenotype.

SUMMARY OF THE INVENTION

The inventors found that *Brassica napus* plants with a pod shatter phenotype similar to the *Brassica* plants described in WO09/068313 (claiming priority of European patent application EP 07023052), i.e. which combine an increased pod shatter resistance with an agronomically relevant treshability of the pods, can also be obtained by combining two partial knock-out mutant IND alleles with or without two full knock-out mutant IND alleles instead of combining three full knockout mutant IND alleles.

Thus, in a first aspect, the present invention provides a *Brassica* plant comprising at least two IND genes, or a cell, part, seed or progeny thereof, characterized in that it comprises at least two partial knockout mutant IND alleles in its genome. In one embodiment, the IND genes are IND-A1 or IND-C1 genes. In another embodiment, the IND genes comprise a nucleic acid molecule selected from the group consisting of: a nucleic acid molecule which comprises at least 90% sequence identity to SEQ ID NO: 1, SEQ ID NO: 3 from the nucleotide at position 46 to the nucleotide at position 633, SEQ ID NO: 3, SEQ ID NO: 5, or SEQ ID NO: 7; and a nucleic acid molecule encoding an amino acid sequence comprising at least 90% sequence identity to SEQ ID NO: 2, SEQ ID NO: 4 from the amino acid at position 16 to the amino acid at position 21 or SEQ ID NO: 4. In a further embodiment, the partial knockout mutant IND alleles are mutant IND alleles of the IND-C1 gene. In still a further embodiment, the partial knockout mutant IND alleles are selected from the group consisting of ind-a1-EMS06, ind-a1-EMS09, ind-a1-EMS13, ind-c1-EMS04, ind-c1-EMS08 and ind-c1-EMS09. In yet a further embodiment, the plant further comprises at least one full knockout mutant IND allele in its genome. In still a further embodiment, the full knockout mutant IND allele is a mutant IND allele of the IND-C1 gene. In another embodiment, the full knockout mutant IND allele is selected from the group consisting of ind-a1-EMS01, ind-a1-EMS05, ind-c1-EMS01 and ind-c1-EMS03. In yet another embodiment, the plant is homozygous for the partial and/or for the full knockout mutant IND allele. In still another embodiment, the plant produces a significantly reduced amount of functional IND protein compared to the amount of functional IND protein produced by a corresponding plant not comprising mutant IND alleles. In a further embodiment, the seed shattering of the plant is significantly reduced or delayed compared to the seed shattering of a corresponding plant not comprising mutant IND alleles. In an even further embodiment, the plant maintains an agronomically relevant treshability of the pods. In yet another embodiment, the plant is a plant from a *Brassica* crop species, preferably *Brassica napus*, *Brassica juncea*, *Brassica carinata*, *Brassica rapa* or *Brassica oleracea*. In still another embodiment, the plant is a plant from a *Brassica* oilseed species, preferably *Brassica napus*, *Brassica juncea* or *Brassica rapa*.

In another aspect, the invention provides a plant, or a cell, part, seed or progeny thereof, comprising at least one partial knockout mutant allele of an IND gene in its genome, wherein the IND gene comprises a nucleic acid molecule selected from the group consisting of: a nucleic acid molecule which comprises at least 90% sequence identity to SEQ ID NO: 1, SEQ ID NO: 3 from the nucleotide at position 46 to the nucleotide at position 633, SEQ ID NO: 3, SEQ ID NO: 5, or SEQ ID NO: 7; and a nucleic acid molecule encoding an amino acid sequence comprising at least 90% sequence identity to SEQ ID NO: 2, SEQ ID NO: 4 from the amino acid at position 16 to the amino acid at position 21 or SEQ ID NO: 4. In one embodiment, the partial knockout mutant IND allele is selected from the group consisting of ind-a1-EMS06, ind-a1-EMS09, ind-a1-EMS13, ind-c1-EMS04, ind-c1-EMS08 and ind-c1-EMS09. In another embodiment, the mutant IND allele is derived from a plant of a *Brassica* species. In yet another embodiment, the plant is a plant from a *Brassica* species.

In a further aspect, a seed pod obtainable from the plants of the invention is provided.

In still a further aspect, a partial knockout mutant allele of an IND gene is provided, wherein the IND gene comprises a nucleic acid molecule selected from the group consisting of: a nucleic acid molecule which comprises at least 90% sequence identity to SEQ ID NO: 1, SEQ ID NO: 3 from the nucleotide at position 46 to the nucleotide at position 633, SEQ ID NO: 3, SEQ ID NO: 5, or SEQ ID NO: 7; and a nucleic acid molecule encoding an amino acid sequence comprising at least 90% sequence identity to SEQ ID NO: 2, SEQ ID NO: 4 from the amino acid at position 16 to the amino acid at position 21 or SEQ ID NO: 4. In one embodiment, the mutant allele is selected from the group consisting of ind-a1-EMS06, ind-a1-EMS09, ind-a1-EMS13, ind-c1-EMS04, ind-c1-EMS08 and ind-c1-EMS09. In another embodiment, the mutant allele is derived from a plant of a *Brassica* species, preferably from a *Brassica* crop species or a *Brassica* oilseed species. In yet a further aspect, a mutant IND protein is provided encoded by the mutant IND alleles of the invention.

In even a further aspect, a method for identifying a mutant IND allele according to the invention in a biological sample is provided comprising determining the presence of a mutant IND specific region in a nucleic acid present in the biological sample. In one embodiment, the method further comprises subjecting the biological sample to a polymerase chain reaction assay using a set of at least two primers, said set being selected from the group consisting of: a set of primers, wherein one of said primers specifically recognizes the 5' flanking region of the mutant IND allele and the other of said primers specifically recognizes the 3' flanking region of the mutant IND allele, respectively; a set of primers, wherein one of said primers specifically recognizes the 5' or 3' flanking region of the mutant IND allele and the other of said primers specifically recognizes the mutation region of the mutant IND allele; and a set of primers, wherein one of said primers specifically recognizes the 5' or 3' flanking region of the mutant IND allele and the other of said primers specifically recognizes the joining region between the 3' or 5' flanking region and the mutation region of the mutant IND allele, respectively. In another embodiment, the primer which specifically recognizes the 5' or 3' flanking region of the mutant IND allele consist of a nucleotide sequence of 17 to 200 consecutive nucleotides selected from the 5' or 3' flanking sequence of the mutant IND allele or from the complement thereof, respectively, or the primer which specifically recognizes the mutation region of the mutant IND allele consists of a nucleotide sequence of 17 to 200 consecutive nucleotides selected from the mutation sequence of the mutant IND allele or from the complement thereof, or the primer which specifically recognizes the joining region between the 5' or 3' flanking region and the mutation region of the mutant IND allele consists of a nucleotide sequence of 17 to 200 consecutive nucleotides selected from a sequence spanning the joining region between the 5' or 3' flanking region and the mutation region of the mutant IND allele or from the complement thereof, wherein said 17 to 200 consecutive nucleotides are not derived exclusively from either the mutation or the flanking sequences. In still a further embodiment, the primer which specifically recognizes the 5' or 3' flanking region of the mutant IND allele comprises at its extreme 3' end a nucleotide sequence of at least 17 consecutive nucleotides selected from the 5' or 3' flanking sequence of the mutant IND allele or from the complement thereof, respectively, or the primer which specifically recognizes the mutation region of the mutant IND allele comprises at its extreme 3' end a nucleotide sequence of at least 17 consecutive nucleotides selected from the mutation sequence of the mutant IND allele or from the complement thereof, or the primer which specifically recognizes the joining region between the 5' or 3' flanking region and the mutation region of the mutant IND allele comprises at its extreme 3' end a nucleotide sequence of at least 17 consecutive nucleotides selected from a sequence spanning the joining region between the 5' or 3' flanking region and the mutation region of the mutant IND allele or from the complement thereof, wherein said 3'-located 17 consecutive nucleotides are not derived exclusively from either the mutation or the flanking sequences. In yet a further embodiment, the method further comprises subjecting the biological sample to an hybridization assay using a set of specific probes comprising at least one specific probe, said set being selected from the group consisting of: a set of specific probes, wherein one of said probes specifically recognizes the 5' flanking region of the mutant IND allele, and the other of said probes specifically recognizes the 3' flanking region of the mutant IND allele; a set of specific probes, wherein one of said probes specifically recognizes the 5' or 3' flanking region of the mutant IND allele, and the other of said probes specifically recognizes the mutation region of the mutant IND allele; a set of specific probes, wherein one of said probes specifically recognizes the 5' or 3' flanking region of the mutant IND allele and the other of said probes specifically recognizes the joining region between the 3' or 5' flanking region and the mutation region of the mutant IND allele, respectively; and a specific probe which specifically recognizes the joining region between the 5' or 3' flanking region and the mutation region of the mutant IND allele. In still a further embodiment, the probe which specifically recognizes the 5' or 3' flanking region of the mutant IND allele consists of a nucleotide sequence of 13 to 1000 consecutive nucleotides selected from the 5' or 3' flanking sequence of the mutant IND allele or from the complement thereof, respectively, or a sequence having at least 80% sequence identity therewith, or the probe which specifically recognizes the mutation region of the mutant IND allele consists of a nucleotide sequence of 13 to 1000 consecutive nucleotides selected from the mutation sequence of the mutant IND allele or from the complement thereof, or a sequence having at least 80% sequence identity therewith, or the probe which specifically recognizes the joining region between the 5' or 3' flanking region and the mutation region of the mutant IND allele consists of a nucleotide sequence of 13 to 1000 consecutive nucleotides selected from a sequence spanning the joining region between the 5' or 3' flanking region and the mutation region of the mutant IND allele or from the complement thereof, respectively, wherein said 13 to 1000 consecutive nucleotides are not derived exclusively from either the mutation or the flanking sequences, or a sequence having at least 80% sequence identity therewith. In a particular embodiment, the probe which specifically recognizes the 5' or 3' flanking region of the mutant IND allele comprises a nucleotide sequence of at least 13 consecutive nucleotides selected from the 5' or 3' flanking sequence of the mutant IND allele or from the complement thereof, respectively, or the probe which specifically recognizes the mutation region of the mutant IND allele comprises a nucleotide sequence of at least 13 consecutive nucleotides selected from the mutation sequence of the mutant IND allele or from the complement thereof, or the probe which specifically recognizes the joining region between the 5' or 3' flanking region and the mutation region of the mutant IND allele comprises a nucleotide sequence of at least 13 consecutive nucleotides selected from a sequence spanning the joining region between the 5' or 3' flanking region and the mutation region of the mutant IND allele or from the complement thereof, respectively, wherein said at least 13 consecutive nucleotides are not derived exclusively from either the mutation or the flanking sequences. In another particular embodiment, the 5' or 3' flanking region comprises the nucleotide sequence of SEQ ID NO: 5 from nucleotide 1 to 929 or 931 to 1622 or of the complement thereof, respectively; said mutation region has the nucleotide sequence of nucleotide 930 of SEQ ID NO: 5 or of the complement thereof; and said joining region comprises the nucleotide sequence of SEQ ID NO: 5 from nucleotide 1 to 930 or 930 to 1622 or of the complement thereof, respectively; or the 5' or 3' flanking region comprises the nucleotide sequence of SEQ ID NO: 5 from nucleotide 1 to 995 or 997 to 1622 or of the complement thereof, respectively; said mutation region has the nucleotide sequence of nucleotide 996 of SEQ ID NO: 5 or of the complement thereof; and said joining region comprises the nucleotide sequence of SEQ ID NO: 5 from nucleotide 1 to 996 or 996 to 1622 or of the complement thereof, respectively; or the 5' or 3' flanking region comprises the nucleotide sequence of SEQ ID NO: 5 from nucleotide 1 to 1035 or 1037 to 1622 or of the complement thereof, respectively; said mutation region has the nucleotide sequence of nucleotide 1036 of SEQ ID NO: 5 or of the complement thereof; and said joining region comprises the nucleotide sequence of SEQ ID NO: 5 from nucleotide 1 to 1036 or 1036 to 1622 or of the complement thereof, respectively; or the 5' or 3' flanking region comprises the nucleotide sequence of SEQ ID NO: 7 from nucleotide 1 to 902 or 904 to 1593 or of the complement thereof, respectively; said mutation region has the nucleotide sequence of nucleotide 903 of SEQ ID NO: 7 or of the complement thereof; and said joining region comprises the nucleotide sequence of SEQ ID NO: 7 from nucleotide 1 to 903 or 903 to 1593 or of the complement thereof, respectively; or the 5' or 3' flanking region comprises the nucleotide sequence of SEQ ID NO: 7 from nucleotide 1 to 910 or 912 to 1593 or of the complement thereof, respectively; said mutation region has the nucleotide sequence of nucleotide 911 of SEQ ID NO: 7 or of the complement thereof; and said joining region comprises the nucleotide sequence of SEQ ID NO: 7 from nucleotide 1 to 911 or 911 to 1593 or of the complement thereof, respectively; or the 5' or 3' flanking region comprises the nucleotide sequence of SEQ ID NO: 7 from nucleotide 1 to 919 or 921 to 1593 or of the complement thereof, respectively; said mutation region has the nucleotide sequence of nucleotide 920 of SEQ ID NO: 7 or of the complement thereof; and said joining region comprises the nucleotide sequence of SEQ ID NO: 7 from nucleotide 1 to 920 or 920 to 1593 or of the complement thereof, respectively. In still another particular embodiment, the set of probes is selected from the group consisting of: a set of probes comprising one probe comprising the sequence of SEQ ID NO: 11 and/or one probe comprising the sequence of SEQ ID NO: 12; a set of probes comprising one probe comprising the sequence of SEQ ID NO: 14 and/or one probe comprising the sequence of SEQ ID NO: 15; a set of probes comprising one probe comprising the sequence of SEQ ID NO: 17 and/or one probe comprising the sequence of SEQ ID NO: 18; a set of probes comprising one probe comprising the sequence of SEQ ID NO: 20 and/or one probe comprising the sequence of SEQ ID NO: 21; a set of probes comprising one probe comprising the sequence of SEQ ID NO: 23 and/or one probe comprising the sequence of SEQ ID NO: 24; and a set of probes comprising one probe comprising the sequence of SEQ ID NO: 26 and/or one probe comprising the sequence of SEQ ID NO: 27.

In yet another aspect, a method for determining the zygosity status of a mutant IND allele according to the invention in a plant, or a cell, part, seed or progeny thereof, is provided comprising determining the presence of a mutant and/or a corresponding wild type IND specific region in the genomic DNA of said plant, or a cell, part, seed or progeny thereof. In one embodiment, the method further comprises subjecting the genomic DNA of said plant, or a cell, part, seed or progeny thereof, to a polymerase chain reaction assay using a set of at least two or at least three primers, wherein at least two of said primers specifically recognize the wild type IND allele, said at least two primers being selected from the group consisting of: a first primer which specifically recognizes the 5' or 3' flanking region of the mutant and the wild type IND allele, and a second primer which specifically recognizes the 3' or 5' flanking region of the mutant and the wild type IND allele, respectively; a first primer which specifically recognizes the 5' or 3' flanking region of the mutant and the wild type IND allele, and a second primer which specifically recognizes the mutation region of the wild type IND allele; and a first primer which specifically recognizes the 5' or 3' flanking region of the mutant and the wild type IND allele, and a second primer which specifically recognizes the joining region between the 3' or 5' flanking region and the mutation region of the wild type IND allele, respectively; and wherein at least two of said primers specifically recognize the mutant IND allele, said at least two primers being selected from the group consisting of: the first primer which specifically recognizes the 5' or 3' flanking region of the mutant and the wild type IND allele, and the second primer which specifically recognizes the 3' or 5' flanking region of the mutant and the wild type IND allele, respectively; the first primer which specifically recognizes the 5' or 3' flanking region of the mutant and the wild type IND allele, and a third primer which specifically recognizes the mutation region of the mutant IND allele; and the first primer which specifically recognizes the 5' or 3' flanking region of the mutant and the wild type IND allele, and a third primer which specifically recognizes the joining region between the 3' or 5' flanking region and the mutation region of the mutant IND allele, respectively. In a further embodiment, the primer which specifically recognizes the 5' or 3' flanking region of the mutant and the wild type IND allele consist of a nucleotide sequence of 17 to 200 consecutive nucleotides selected from the 5' or 3' flanking sequence of the mutant and the wild type IND allele or from the complement thereof, respectively; or the primers which specifically recognizes the mutation region of the mutant or the wild type IND allele consists of a nucleotide sequence of 17 to 200 consecutive nucleotides selected from the mutation sequence of the mutant or the wild type IND allele or from the complement thereof, respectively; or the primers which specifically recognizes the joining region between the 5' or 3' flanking region and the mutation region of the mutant or the wild type IND allele, consists of a nucleotide sequence of 17 to 200 consecutive nucleotides selected from a sequence spanning the joining region between the 5' or 3' flanking region and the mutation region of the mutant or the wild type IND allele or from the complement thereof, respectively, wherein said 17 to 200 consecutive nucleotides are not derived exclusively from either the mutation region or from the flanking sequences. In yet a further embodiment, the primer which specifically recognizes the 5' or 3' flanking region of the mutant and the wild type IND allele comprises at its extreme 3' end a nucleotide sequence of 17 consecutive nucleotides selected from the 5' or 3' flanking sequence of the mutant and the wild type IND allele or from the complement thereof, respectively; or the primers which specifically recognizes the mutation region of the mutant or the wild type IND allele comprises at its extreme 3' end a nucleotide sequence of 17 consecutive nucleotides selected from the mutation sequence of the mutant or the wild type IND allele or from the complement thereof, respectively; or the primers which specifically recognizes the joining region between the 5' or 3' flanking region and the mutation region of the mutant or the wild type IND allele comprises at its extreme 3' end a nucleotide sequence of 17 consecutive nucleotides selected from a sequence spanning the joining region between the 5' or 3' flanking region and the mutation region of the mutant or the wild type IND allele or from the complement thereof, respectively, wherein said 3'-located 17 consecutive nucleotides are not derived exclusively from either the mutation site or region or from the flanking sequences. In still a further embodiment, the method further comprises subjecting the genomic DNA of said plant, or a cell, part, seed or progeny thereof, to an hybridization assay using a set of at least two specific probes, wherein at least one of said specific probes specifically recognizes the wild type IND allele, said at least one probe selected from the group consisting of: a first probe which specifically recognizes the 5' or 3' flanking region of the mutant and the wild type IND allele, and a second probe which specifically recognizes the 3' and 5' flanking region of the mutant and the wild type IND allele, respectively; a first probe which specifically recognizes the 5' or 3' flanking region of the mutant and the wild type IND allele, and a second probe which specifically recognizes the mutation region of the wild type IND allele; a first probe which specifically recognizes the 5' or 3' flanking region of the mutant and the wild type IND allele, and a second probe which specifically recognizes the joining region between the 3' or 5' flanking region and the mutation region of the wild type IND allele, respectively; and a probe which specifically recognizes the joining region between the 5' or 3' flanking region and the mutation region of the wild type IND allele; and wherein at least one of said specific probes specifically recognize(s) the mutant IND allele, said at least one probe selected from the group consisting of: the first probe which specifically recognizes the 5' or 3' flanking region of the mutant and the wild type IND allele, and the second probe which specifically recognizes the 3' or 5' flanking region of the mutant and the wild type IND allele, respectively; the first probe which specifically recognizes the 5' or 3' flanking region of the mutant and the wild type IND allele, and a third probe which specifically recognizes the mutation region of the mutant IND allele; the first probe which specifically recognizes the 5' or 3' flanking region of the mutant and the wild type IND allele, and a third probe which specifically recognizes the joining region between the 5' or 3' flanking region and the mutation region of the mutant IND allele; and a probe which specifically recognizes the joining region between the 5' or 3' flanking region and the mutation region of the mutant IND allele. In a particular embodiment, the probe which specifically recognizes the 5' or 3' flanking region of the mutant and the wild type IND allele consists of a nucleotide sequence of 13 to 1000 consecutive nucleotides selected from the 5' or 3' flanking sequence of the mutant or the wild type IND allele or from the complement thereof, respectively, or a sequence having at least 80% sequence identity therewith, or the probe which specifically recognizes the mutation region of the mutant or the wild type IND allele consists of a nucleotide sequence of 13 to 1000 consecutive nucleotides selected from the sequence of the mutation region of the mutant or the wild type IND allele, respectively, or a sequence having at least 80% sequence identity therewith, or the probe which specifically recognizes the joining region between the 5' or 3' flanking region and the mutation region of the mutant or the wild type IND allele consists of a nucleotide sequence of 13 to 1000 consecutive nucleotides selected from a sequence spanning the joining region between the 5' or 3' flanking region and the mutation region of the mutant or the wild type IND allele, respectively, or a sequence having at least 80% sequence identity therewith, wherein said 13 to 1000 consecutive nucleotides are not derived exclusively from either the mutation site or region or from the flanking sequences. In another particular embodiment, the probe which specifically recognizes the 5' or 3' flanking region of the mutant and the wild type IND allele comprises a nucleotide sequence of at least 13 consecutive nucleotides selected from the 5' or 3' flanking sequence of the mutant or the wild type IND allele or from the complement thereof, respectively, or the probe which specifically recognizes the mutation region of the mutant or the wild type IND allele comprises a nucleotide sequence of at least 13 consecutive nucleotides selected from the mutation sequence of the mutant or the wild type IND allele or from the complement thereof, or the probe which specifically recognizes the joining region between the 5' or 3' flanking region and the mutation region of the mutant or the wild type IND allele comprises a nucleotide sequence of at least 13 consecutive nucleotides selected from a sequence spanning the joining region between the 5' or 3' flanking region and the mutation region of the mutant or the wild type IND allele or from the complement thereof, respectively, wherein said at least 13 consecutive nucleotides are not derived exclusively from either the mutation or the flanking sequences. In a further particular embodiment, the 5' or 3' flanking region comprises the nucleotide sequence of SEQ ID NO: 5 from nucleotide 1 to 929 or 931 to 1622 or of the complement thereof, respectively; said mutation region of the wild type IND allele has the nucleotide sequence of nucleotide 930 of SEQ ID NO: 5 or of the complement thereof; said mutation region of the mutant IND allele has the sequence a or the complement thereof; said joining region of the wild type IND allele comprises the nucleotide sequence of SEQ ID NO: 5 from nucleotide 1 to 930 or 930 to 1622 or of the complement thereof, respectively; and said joining region of the mutant IND allele comprises the nucleotide sequence of SEQ ID NO: 5 from nucleotide 1 to 929 followed by a or a followed by the nucleotide sequence SEQ ID NO: 5 from nucleotide 931 to 1622 or of the complement thereof, respectively; or the 5' or 3' flanking region comprises the nucleotide sequence of SEQ ID NO: 5 from nucleotide 1 to 995 or 997 to 1622 or of the complement thereof, respectively; said mutation region of the wild type IND allele has the nucleotide sequence of nucleotide 996 of SEQ ID NO: 5 or of the complement thereof; said mutation region of the mutant IND allele has the sequence a or the complement thereof; said joining region of the wild type IND allele comprises the nucleotide sequence of SEQ ID NO: 5 from nucleotide 1 to 996 or 996 to 1622 or of the complement thereof, respectively; and said joining region of the mutant IND allele comprises the nucleotide sequence of SEQ ID NO: 5 from nucleotide 1 to 995 followed by a or a followed by the nucleotide sequence SEQ ID NO: 5 from nucleotide 997 to 1622 or of the complement thereof, respectively; or the 5' or 3' flanking region comprises the nucleotide sequence of SEQ ID NO: 5 from nucleotide 1 to 1035 or 1037 to 1622 or of the complement thereof, respectively; said mutation region of the wild type IND allele has the nucleotide sequence of nucleotide 1036 of SEQ ID NO: 5 or of the complement thereof; said mutation region of the mutant IND allele has the sequence t or the complement thereof; said joining region of the wild type IND allele comprises the nucleotide sequence of SEQ ID NO: 5 from nucleotide 1 to 1036 or 1036 to 1622 or of the complement thereof, respectively; and said joining region of the mutant IND allele comprises the nucleotide sequence of SEQ ID NO: 5 from nucleotide 1 to 1035 followed by t or t followed by the nucleotide sequence SEQ ID NO: 5 from nucleotide 1037 to 1622 or of the complement thereof, respectively; or the 5' or 3' flanking region comprises the nucleotide sequence of SEQ ID NO: 7 from nucleotide 1 to 902 or 904 to 1593 or of the complement thereof, respectively; said mutation region of the wild type IND allele has the nucleotide sequence of nucleotide 903 of SEQ ID NO: 7 or of the complement thereof; said mutation region of the mutant IND allele has the sequence t or the complement thereof; and said joining region of the wild type IND allele comprises the nucleotide sequence of SEQ ID NO: 7 from nucleotide 1 to 903 or 903 to 1593 or of the complement thereof, respectively; and said joining region of the mutant IND allele comprises the nucleotide sequence of SEQ ID NO: 7 from nucleotide 1 to 902 followed by t or t followed by the nucleotide sequence SEQ ID NO: 7 from nucleotide 904 to 1593 or of the complement thereof, respectively; or the 5' or 3' flanking region comprises the nucleotide sequence of SEQ ID NO: 7 from nucleotide 1 to 910 or 912 to 1593 or of the complement thereof, respectively; said mutation region of the wild type IND allele has the nucleotide sequence of nucleotide 911 of SEQ ID NO: 7 or of the complement thereof; said mutation region of the mutant IND allele has the sequence a or the complement thereof; and said joining region of the wild type IND allele comprises the nucleotide sequence of SEQ ID NO: 7 from nucleotide 1 to 911 or 911 to 1593 or of the complement thereof, respectively; and said joining region of the mutant IND allele comprises the nucleotide sequence of SEQ ID NO: 7 from nucleotide 1 to 910 followed by a or a followed by the nucleotide sequence SEQ ID NO: 7 from nucleotide 912 to 1593 or of the complement thereof, respectively; or the 5' or 3' flanking region comprises the nucleotide sequence of SEQ ID NO: 7 from nucleotide 1 to 919 or 921 to 1593 or of the complement thereof, respectively; said mutation region of the wild type IND allele has the nucleotide sequence of nucleotide 920 of SEQ ID NO: 7 or of the complement thereof; said mutation region of the mutant IND allele has the sequence t or the complement thereof; and said joining region of the wild type IND allele comprises the nucleotide sequence of SEQ ID NO: 7 from nucleotide 1 to 920 or 920 to 1593 or of the complement thereof, respectively; and said joining region of the mutant IND allele comprises the nucleotide sequence of SEQ ID NO: 7 from nucleotide 1 to 919 followed by t or t followed by the nucleotide sequence SEQ ID NO: 7 from nucleotide 921 to 1593 or of the complement thereof, respectively. In a specific embodiment, the set of at least three specific probes is selected from the group consisting of: a set of probes comprising one probe comprising the sequence of SEQ ID NO: 11, one probe comprising the sequence of SEQ ID NO: 12, and/or one probe comprising the sequence of SEQ ID NO: 13; a set of probes comprising one probe comprising the sequence of SEQ ID NO: 14, one probe comprising the sequence of SEQ ID NO: 15, and/or one probe comprising the sequence of SEQ ID NO: 16; a set of probes comprising one probe comprising the sequence of SEQ ID NO: 17, one probe comprising the sequence of SEQ ID NO: 18, and/or one probe comprising the sequence of SEQ ID NO: 19; a set of probes comprising one probe comprising the sequence of SEQ ID NO: 20, one probe comprising the sequence of SEQ ID NO: 21 and/or one probe comprising the sequence of SEQ ID NO: 22; a set of probes comprising one probe comprising the sequence of SEQ ID NO: 23, one probe comprising the sequence of SEQ ID NO: 24 and/or one probe comprising the sequence of SEQ ID NO: 25; and a set of probes comprising one probe comprising the sequence of SEQ ID NO: 26, one probe comprising the sequence of SEQ ID NO: 27 and/or one probe comprising the sequence of SEQ ID NO: 28.

Kits for identifying a mutant IND allele according to the invention in a biological sample, and kits for determining the zygosity status of a mutant IND allele according to the invention in a plant, or a cell, part, seed or progeny thereof comprising the primers or probes as described above are also provided, as are methods for combining the mutant IND alleles according to the invention in one plant, methods for transferring the mutant IND alleles according to the invention from one plant to another plant, and methods for making a (hybrid) plant or seed according to the invention.

In another embodiment of the invention, the mutant IND alleles of the invention are used to increase the yield of harvested seed or grain from *Brassica* plants. The increased yield may be a consequence of reducing or delaying seed shattering, but may also be independent from the reduced or delayed seed shatter. In particular, *Brassica* plants are provided comprising at least two IND genes, or a cell, part, seed or progeny thereof, characterized in that these plants comprise two mutant homozygous IND alleles as herein described in their genome.

GENERAL DEFINITIONS

"Increase of pod shatter resistance" and "reduction of seed shattering", as used herein, refers to a decreased seed shatter tendency and/or a delay in the timing of seed shattering, in particular until after harvest, of *Brassica* plants, the fruits of which normally do not mature synchronously, but sequentially, so that some pods burst open and shatter their seeds before or during harvest. The level of resistance to pod shattering is positively correlated with and can, for example, be measured by determining the force needed to break pods in the 'tensile separation test' (Davies and Bruce, 1997, J Mat Sci 32: 5895-5899; Morgan et al., 1998, Fields Crop Research 58, 153-165), the number of intact pods remaining after e.g. 20 sec ('IP20'; Morgan et al., 1998, supra), 9.7 or 17 sec (Bruce et al., 2002, Biosystems Eng 81(2): 179-184) in a 'random impact test', the pod sample half-life (hereinafter also referred to as 'LD50') in a random impact test, i.e. the treatment time needed to cause the opening of 50% of the pods in tested pod samples, and the 'field score for shattering' (Morgan et al., 1998, supra). Random impact tests (RITs) and algorithms to define the pod sample half-lives in such RITs have been described in Bruce et al., 2002 (supra), Morgan et al., 1998 (supra) and the Examples below. Both publications are hereby incorporated by reference. Briefly, a sample of intact mature pods is placed in a closed drum together with steel balls and the drum is then vigorously agitated for increasing periods of times (e.g. 10 s, 20 s, 40 s, 80 s). After each period, the drum is opened and the number of broken and damaged pods is counted. The most accurate estimation of the level of shattering resistance for each line is calculated by fitting a linear×linear curve to all the available data and estimating the time taken for half of the pods within a sample to be broken ("pod sample half-life" or "LD50"). It is important however that pods open mainly along the dehiscence zone, and are not simply pulverized, as may occur with indehiscent pods.

An "agronomically relevant increase of pod shatter resistance", as used herein, refers to an increase of pod shatter resistance in a plant which results in pod shatter-related yield losses in the field (pre-harvest) below those normally observed for that plant in the field. For oilseed rape, pod shatter-related yield losses in the field are reported to be about 11% for a season with on average good growth conditions and about 25% for a season with on average bad growth conditions. A positive correlation has been found between these levels of seed loss and the level of seed loss at 9.7 s and 17 s treatment time, respectively, in the random impact test as described by Bruce et al., 2002 (Biosystems Eng 81(2): 179-184). Alternatively, to determine whether the level of resistance to pod shattering in a plant is agronomically relevant, the pod sample half-life ('LD50', see above) of the plant can be compared with the pod sample half-life of a plant known to have an average level of pod shatter resistance, such as, for oilseed rape, all currently commercially available oilseed rape varieties.

As used herein, "pod or seed shattering" or "fruit or pod dehiscence" refers to a process that takes place in a fruit after seed maturation, whereby the valves detach from the central septum freeing the seeds. The region that breaks (i.e. the "dehiscence zone") runs the entire length of the fruit between the valves and the replum (external septum). At maturity, the "dehiscence zone" is essentially a non-lignified layer of cells between a region of lignified cells in the valve and the replum. Shattering occurs due to the combination of cell wall loosening in the dehiscence zone and the tensions established by the differential mechanical properties of the drying cells in the silique.

A *Brassica* "fruit", as used herein, refers to an organ of a *Brassica* plant that develops from a gynoecium composed of fused carpels, which, upon fertilization, grows to become a "(seed) pod" or "silique" that contains the developing seeds. A *Brassica* "(seed) pod" or "silique" consists of a fruit wall (carpel) enclosing two locules separated by the septum. The "dehiscence zones" develop at the carpel margins adjacent to the septum and run the length of the silique. The cells of the dehiscence zone eventually begin to degrade and this weakens the contact between the carpel walls or valves and the septum. The loss of cellular cohesion is confined to the cells of the dehiscence zone and results from middle lamella breakdown (Meakin and Roberts, 1990, J Exp Bot 41, 995-1011).

"Dehiscence zones", as used herein, refers to layers of simple, parenchymatous cells, contained in the sutures situated on both sides of the bi-valved pod of plants, in particular *Brassica* plants. The dehiscence zones are situated between the pod valve edge and a central replum that contains the main vascular bundle to the stalk or pedicel. Dissociation of the cells in the dehiscence zone takes place during pod senescence and is complete by the time the pods reach full maturity (Meakin and Roberts, 1990, supra). Valve separation can than take place. The dehiscence zone contains vascular traces, which pass from the pod wall to the pedicel (stalk) and the replum. The process of pod shatter takes place only after external force fractures the delicate vascular threads, allowing the valves to separate and the seeds to fall to the ground. This occurs during disturbance of the canopy, for example by contact with the combine during harvesting. The vascular tissue contains thickened, lignified cells, which form the collenchymatous groups of cells found adjacent to the conductive cells (Meakin and Roberts, 1990, supra). This provides rigidity to the tissue and presumably, some resistance to fracturing.

As used herein, "an agronomically relevant treshability" refers to the resistance of a pod, particularly an oilseed rape pod, to opening along the dehiscence zone of the pod with concurrent release of the seeds, upon application of physical forces that allow complete opening of the pods while preventing damage to the seeds, as they are used e.g. in a combine harvester. A positive correlation has been found between a pod sample half-life ('LD50') in a random impact test and their treshability. Oilseed rape pod sample half-lives, as determined in a RIT performed as described in the Examples, which correspond to agronomically relevant treshability should not exceed 80 seconds. Typical sample half-life values for control lines of commercially available oilseed rape varieties are about 10 seconds. Thus, lines with significantly increased pod shatter resistance with agronomically relevant treshability have a pod sample half-life in RIT between about 10 and about 80 seconds, between about 10 and about 70 seconds, between about 15 and about 70 seconds, between about 10 and about 60 seconds, between about 10 and about 50 seconds, between about 20 and about 60 seconds, between about 20 and about 50 seconds, between about 40 and about 60 seconds, of about 57 seconds.

"Dehiscent seed plant" means a plant that produces a dry dehiscent fruit, which has fruit walls that open to permit escape of the seeds contained therein. Dehiscent fruits commonly contain several seeds and include the fruits known, for example, as legumes, capsules and siliques.

"Crop plant" refers to plant species cultivated as a crop, such as *Brassica napus* (AACC, 2n=38), *Brassica juncea* (AABB, 2n=36), *Brassica carinata* (BBCC, 2n=34), *Brassica rapa* (syn. *B. campestris*) (AA, 2n=20), *Brassica oleracea* (CC, 2n=18) or *Brassica nigra* (BB, 2n=16). The definition does not encompass weeds, such as *Arabidopsis thaliana*.

The term "nucleic acid sequence" (or nucleic acid molecule) refers to a DNA or RNA molecule in single or double stranded form, particularly a DNA encoding a protein or protein fragment according to the invention. An "endogenous nucleic acid sequence" refers to a nucleic acid sequence within a plant cell, e.g. an endogenous allele of an IND gene present within the nuclear genome of a *Brassica* cell. An "isolated nucleic acid sequence" is used to refer to a nucleic acid sequence that is no longer in its natural environment, for example in vitro or in a recombinant bacterial or plant host cell.

The term "gene" means a DNA sequence comprising a region (transcribed region), which is transcribed into an RNA molecule (e.g. into a pre-mRNA, comprising intron sequences, which is then spliced into a mature mRNA, or directly into a mRNA without intron sequences) in a cell, operable linked to regulatory regions (e.g. a promoter). A gene may thus comprise several operably linked sequences, such as a promoter, a 5' leader sequence comprising e.g. sequences involved in translation initiation, a (protein) coding region (cDNA or genomic DNA) and a 3' non-translated sequence comprising e.g. transcription termination sites. "Endogenous gene" is used to differentiate from a "foreign gene", "transgene" or "chimeric gene", and refers to a gene from a plant of a certain plant genus, species or variety, which has not been introduced into that plant by transformation (i.e. it is not a "transgene"), but which is normally present in plants of that genus, species or variety, or which is introduced in that plant from plants of another plant genus, species or variety, in which it is normally present, by normal breeding techniques or by somatic hybridization, e.g., by protoplast fusion. Similarly, an "endogenous allele" of a gene is not introduced into a plant or plant tissue by plant transformation, but is, for example, generated by plant mutagenesis and/or selection or obtained by screening natural populations of plants.

"Expression of a gene" or "gene expression" refers to the process wherein a DNA region, which is operably linked to appropriate regulatory regions, particularly a promoter, is transcribed into an RNA molecule. The RNA molecule is then processed further (by post-transcriptional processes) within the cell, e.g. by RNA splicing and translation initiation and translation into an amino acid chain (protein), and translation termination by translation stop codons. The term "functionally expressed" is used herein to indicate that a functional protein is produced; the term "not functionally expressed" to indicate that a protein with significantly reduced or no functionality (biological activity) is produced or that no protein is produced (see further below).

The term "protein" refers to a molecule consisting of a chain of amino acids, without reference to a specific mode of action, size, 3-dimensional structure or origin. A "fragment" or "portion" of an IND protein may thus still be referred to as a "protein". An "isolated protein" is used to refer to a protein that is no longer in its natural environment, for example in vitro or in a recombinant bacterial or plant host cell. "Amino acids" are the principal building blocks of proteins and enzymes. They are incorporated into proteins by transfer RNA according to the genetic code while messenger RNA is being decoded by ribosomes. During and after the final assembly of a protein, the amino acid content dictates the spatial and biochemical properties of the protein or enzyme. The amino acid backbone determines the primary sequence of a protein, but the nature of the side chains determines the protein's properties. "Similar amino acids", as used herein, refers to amino acids that have similar amino acid side chains, i.e. amino acids that have polar, non-polar or practically neutral side chains. "Non-similar amino acids", as used herein, refers to amino acids that have different amino acid side chains, for example an amino acid with a polar side chain is non-similar to an amino acid with a non-polar side chain. Polar side chains usually tend to be present on the surface of a protein where they can interact with the aqueous environment found in cells ("hydrophilic" amino acids). On the other hand, "non-polar" amino acids tend to reside within the center of the protein where they can interact with similar non-polar neighbors ("hydrophobic" amino acids"). Examples of amino acids that have polar side chains are arginine, asparagine, aspartate, cysteine, glutamine, glutamate, histidine, lysine, serine, and threonine (all hydrophilic, except for cysteine which is hydrophobic). Examples of amino acids that have non-polar side chains are alanine, glycine, isoleucine, leucine, methionine, phenylalanine, proline, and tryptophan (all hydrophobic, except for glycine which is neutral).

The term "transcription factor" is used to refer to a protein consisting of at least two discrete domains—a DNA binding domain and an activation or repression domain—that operate together to modulate the rate of transcriptional initiation from target gene promoters (Ptashne, 1988, Nature 335, 683-689). The term "basic helix-loop-helix (bHLH) domain transcription factor" is used to refer to a transcription factor comprising, apart from the bHLH DNA binding domain (Heim et al., 2003, Mol Biol Evol 20, 735-747; Toledo-Ortiz et al., 2003, Plant Cell 15, 1749-1770), domains which are known to be important for the regulation of gene expression which may be conserved at the amino acid level in related proteins from different species (Quong et al., 1993, Mol Cell Biol 13, 792-800). Transcriptional regulators comprising a bHLH domain bind DNA through residues in the basic region while the helix-loop-helix domain promotes dimerization, allowing family members to form hetero- or homodimers (Murre et al., 1989, Cell 56, 777-783).

The term "IND gene" refers herein to a nucleic acid sequence encoding an INDEHISCENT (IND) protein, which is a basic helix-loop-helix (bHLH) domain transcription factor required for seed dispersal (Liljegren et al., 2004, Cell 116: 843-853).

As used herein, the term "allele(s)" means any of one or more alternative forms of a gene at a particular locus. In a diploid (or amphidiploid) cell of an organism, alleles of a given gene are located at a specific location or locus (loci plural) on a chromosome. One allele is present on each chromosome of the pair of homologous chromosomes.

As used herein, the term "homologous chromosomes" means chromosomes that contain information for the same biological features and contain the same genes at the same loci but possibly different alleles of those genes. Homologous chromosomes are chromosomes that pair during meiosis. "Non-homologous chromosomes", representing all the biological features of an organism, form a set, and the number of sets in a cell is called ploidy. Diploid organisms contain two sets of non-homologous chromosomes, wherein each homologous chromosome is inherited from a different parent. In amphidiploid species, essentially two sets of diploid genomes exist, whereby the chromosomes of the two genomes are referred to as "homeologous chromosomes" (and similarly, the loci or genes of the two genomes are referred to as homeologous loci or genes). A diploid, or amphidiploid, plant species may comprise a large number of different alleles at a particular locus.

As used herein, the term "heterozygous" means a genetic condition existing when two different alleles reside at a specific locus, but are positioned individually on corresponding pairs of homologous chromosomes in the cell. Conversely, as used herein, the term "homozygous" means a genetic condition existing when two identical alleles reside at a specific locus, but are positioned individually on corresponding pairs of homologous chromosomes in the cell.

As used herein, the term "locus" (loci plural) means a specific place or places or a site on a chromosome where for example a gene or genetic marker is found. For example, the "IND-A1 locus" refers to the position on a chromosome of the A genome where the IND-A1 gene (and two IND-A1 alleles) may be found, while the "IND-C1 locus" refers to the position on a chromosome of the C genome where the IND-C1 gene (and two IND-C1 alleles) may be found.

Whenever reference to a "plant" or "plants" according to the invention is made, it is understood that also plant parts (cells, tissues or organs, seed pods, seeds, severed parts such as roots, leaves, flowers, pollen, etc.), progeny of the plants which retain the distinguishing characteristics of the parents (especially the fruit dehiscence properties), such as seed obtained by selfing or crossing, e.g. hybrid seed (obtained by crossing two inbred parental lines), hybrid plants and plant parts derived there from are encompassed herein, unless otherwise indicated.

A "molecular assay" (or test) refers herein to an assay that indicates (directly or indirectly) the presence or absence of one or more particular IND alleles at one or both IND loci (e.g. at one or both of the IND-A1 or IND-C1 loci). In one embodiment it allows one to determine whether a particular (wild type or mutant) IND allele is homozygous or heterozygous at the locus in any individual plant.

"Wild type" (also written "wildtype" or "wild-type"), as used herein, refers to a typical form of a plant or a gene as it most commonly occurs in nature. A "wild type plant" refers to a plant with the most common phenotype of such plant in the natural population. A "wild type allele" refers to an allele of a gene required to produce the wild-type phenotype. By contrast, a "mutant plant" refers to a plant with a different rare phenotype of such plant in the natural population or produced by human intervention, e.g. by mutagenesis, and a "mutant allele" refers to an allele of a gene required to produce the mutant phenotype.

As used herein, the term "wild type IND" (e.g. wild type IND-A1 or IND-C1), means a naturally occurring IND allele found within plants, in particular Brassicacea plants, especially *Brassica* plants, which encodes a functional IND protein (e.g. a functional IND-A1 or IND-C1, respectively). In contrast, the term "mutant IND" (e.g. mutant IND-A1 or IND-C1), as used herein, refers to an IND allele, which does not encode a functional IND protein, i.e. an IND allele encoding a non-functional IND protein (e.g. a non-functional IND-A1 or IND-C1, respectively), which, as used herein, refers to an IND protein having no biological activity or a significantly reduced biological activity as compared to the corresponding wild-type functional IND protein, or encoding no IND protein at all. A "full knock-out" or "null" mutant IND allele, as used herein, refers to a mutant IND allele, which encodes an IND protein having no biological activity as compared to the corresponding wild-type functional IND protein or which encodes no protein at all. Such a "full knock-out mutant IND allele" is, for example, a wild-type IND allele, which comprises one or more mutations in its nucleic acid sequence, for example, one or more non-sense or mis-sense mutations. In particular, such a full knock-out mutant IND allele is a wild-type IND allele, which comprises a mutation that preferably result in the production of an IND protein lacking at least one functional domain, such as the activation domain, the DNA binding domain and/or the dimerization domain, or lacking at least one amino acid critical for its function, such as an amino acid critical for DNA binding, e.g. the arginine at position 127 in SEQ ID NO: 2 or at position 140 in SEQ ID NO: 4 and the like, or the glutamine at position 122 in SEQ ID NO: 2 or at position 135 in SEQ ID NO: 4 and the like, such that the biological activity of the IND protein is completely abolished, or whereby the mutation(s) preferably result in no production of an IND protein. A "partial knock-out" mutant IND allele, as used herein, refers to a mutant IND allele, which encodes an IND protein having a significantly reduced biological activity as compared to the corresponding wild-type functional IND protein. Such a "partial knock-out mutant IND allele" is, for example, a wild-type IND allele, which comprises one or more mutations in its nucleic acid sequence, for example, one or more mis-sense mutations. In particular, such a partial knockout mutant IND allele is a wild-type IND allele, which comprises a mutation that preferably result in the production of an IND protein wherein at least one conserved and/or functional amino acid is substituted for another amino acid, such that the biological activity is significantly reduced but not completely abolished. Such full or partial knock-out mutant IND allele may also encode a dominant negative IND protein, which is capable of adversely affecting the biological activity of other IND proteins within the same cell. Such a dominant negative IND protein can be an IND protein that is still capable of interacting with the same elements as the wild-type IND protein, but that blocks some aspect of its function. Examples of dominant negative IND proteins are IND proteins that lack the activation domain and/or dimerization domain or specific amino acid residues critical for activation and/or dimerization, but still contain the DNA binding domain, such that not only their own biological activity is reduced or abolished, but that they further reduce the total IND activity in the cell by competing with wildtype and/or partial knockout IND proteins present in the cell for DNA binding sites. Other examples of dominant negative IND proteins are IND proteins that lack the activation domain and/or DNA binding domain or specific amino acid residues critical for activation and/or DNA binding but still contain the dimerization domain, such that not only their own biological activity is reduced or abolished, but that they further reduce the total IND activity in the cell by producing protein dimers lacking at least one functional domain. Mutant alleles of the IND protein-encoding nucleic acid sequences are designated as "ind" (e.g. ind-a1 or ind-c1, respectively) herein. Mutant alleles can be either "natural mutant" alleles, which are mutant alleles found in nature (e.g. produced spontaneously without human application of mutagens) or "induced mutant" alleles, which are induced by human intervention, e.g. by mutagenesis.

A "significantly reduced amount of functional IND protein" (e.g. functional IND-A1 or IND-C1 protein) refers to a reduction in the amount of a functional IND protein produced by the cell comprising a mutant IND allele by at least 30%, 40%, 50%, 60%, 70%, 80%, 90%, 95% or 100% (i.e. no functional IND protein is produced by the cell) as compared to the amount of the functional IND protein produced by the cell not comprising the mutant IND allele. This definition encompasses the production of a "non-functional" IND protein (e.g. truncated IND protein) having no biological activity in vivo, the reduction in the absolute amount of the functional IND protein (e.g. no functional IND protein being made due to the mutation in the IND gene), the production of an IND protein with significantly reduced biological activity compared to the activity of a functional wild type IND protein (such as an IND protein in which one or more amino acid residues that are crucial for the biological activity of the encoded IND protein, as exemplified below, are substituted for another amino acid residue) and/or the adverse effect of dominant negative IND proteins on other functional and/or partially functional IND proteins.

The term "mutant IND protein", as used herein, refers to an IND protein encoded by a mutant IND nucleic acid sequence ("ind allele") whereby the mutation results in a significantly reduced and/or no IND activity in vivo, compared to the activity of the IND protein encoded by a non-mutant, wild type IND sequence ("IND allele").

"Mutagenesis", as used herein, refers to the process in which plant cells (e.g., a plurality of Brassica seeds or other parts, such as pollen, etc.) are subjected to a technique which induces mutations in the DNA of the cells, such as contact with a mutagenic agent, such as a chemical substance (such as ethylmethylsulfonate (EMS), ethylnitrosourea (ENU), etc.) or ionizing radiation (neutrons (such as in fast neutron mutagenesis, etc.), alpha rays, gamma rays (such as that supplied by a Cobalt 60 source), X-rays, UV-radiation, etc.), or a combination of two or more of these. Thus, the desired mutagenesis of one or more IND alleles may be accomplished by use of chemical means such as by contact of one or more plant tissues with ethylmethylsulfonate (EMS), ethylnitrosourea, etc., by the use of physical means such as x-ray, etc, or by gamma radiation, such as that supplied by a Cobalt 60 source. While mutations created by irradiation are often large deletions or other gross lesions such as translocations or complex rearrangements, mutations created by chemical mutagens are often more discrete lesions such as point mutations. For example, EMS alkylates guanine bases, which results in base mispairing: an alkylated guanine will pair with a thymine base, resulting primarily in G/C to A/T transitions. Following mutagenesis, Brassica plants are regenerated from the treated cells using known techniques. For instance, the resulting Brassica seeds may be planted in accordance with conventional growing procedures and following self-pollination seed is formed on the plants. Alternatively, doubled haploid plantlets may be extracted to immediately form homozygous plants, for example as described by Coventry et al. (1988, Manual for Microspore Culture Technique for Brassica napus. Dep. Crop Sci. Techn. Bull. OAC Publication 0489. Univ. of Guelph, Guelph, Ontario, Canada). Additional seed that is formed as a result of such self-pollination in the present or a subsequent generation may be harvested and screened for the presence of mutant IND alleles. Several techniques are known to screen for specific mutant alleles, e.g., Delete-agene™ (Delete-a-gene; Li et al., 2001, Plant J 27: 235-242) uses polymerase chain reaction (PCR) assays to screen for deletion mutants generated by fast neutron mutagenesis, TILLING (targeted induced local lesions in genomes; McCallum et al., 2000, Nat Biotechnol 18:455-457) identifies EMS-induced point mutations, etc. Additional techniques to screen for the presence of specific mutant IND alleles are described in the Examples below.

As used herein, the term "non-naturally occurring" or "cultivated" when used in reference to a plant, means a plant with a genome that has been modified by man. A transgenic plant, for example, is a non-naturally occurring plant that contains an exogenous nucleic acid molecule, e.g., a chimeric gene comprising a transcribed region which when transcribed yields a biologically active RNA molecule capable of reducing the expression of an endogenous gene, such as an IND gene, and, therefore, has been genetically modified by man. In addition, a plant that contains a mutation in an endogenous gene, for example, a mutation in an endogenous IND gene, (e.g. in a regulatory element or in the coding sequence) as a result of an exposure to a mutagenic agent is also considered a non-naturally plant, since it has been genetically modified by man. Furthermore, a plant of a particular species, such as Brassica napus, that contains a mutation in an endogenous gene, for example, in an endogenous IND gene, that in nature does not occur in that particular plant species, as a result of, for example, directed breeding processes, such as marker-assisted breeding and selection or introgression, with a plant of the same or another species, such as Brassica juncea or rapa, of that plant is also considered a non-naturally occurring plant. In contrast, a plant containing only spontaneous or naturally occurring mutations, i.e. a plant that has not been genetically modified by man, is not a "non-naturally occurring plant" as defined herein and, therefore, is not encompassed within the invention. One skilled in the art understands that, while a non-naturally occurring plant typically has a nucleotide sequence that is altered as compared to a naturally occurring plant, a non-naturally occurring plant also can be genetically modified by man without altering its nucleotide sequence, for example, by modifying its methylation pattern.

The term "ortholog" of a gene or protein refers herein to the homologous gene or protein found in another species, which has the same function as the gene or protein, but is (usually) diverged in sequence from the time point on when the species harboring the genes diverged (i.e. the genes evolved from a common ancestor by speciation). Orthologs of the Brassica napus IND genes may thus be identified in other plant species (e.g. Brassica juncea, etc.) based on both sequence comparisons (e.g. based on percentages sequence identity over the entire sequence or over specific domains) and/or functional analysis.

A "variety" is used herein in conformity with the UPOV convention and refers to a plant grouping within a single botanical taxon of the lowest known rank, which grouping can be defined by the expression of the characteristics resulting from a given genotype or combination of genotypes, can be distinguished from any other plant grouping by the expression of at least one of the said characteristics and is considered as a unit with regard to its suitability for being propagated unchanged (stable).

The term "comprising" is to be interpreted as specifying the presence of the stated parts, steps or components, but does not exclude the presence of one or more additional parts, steps or components. A plant comprising a certain trait may thus comprise additional traits.

It is understood that when referring to a word in the singular (e.g. plant or root), the plural is also included herein (e.g. a plurality of plants, a plurality of roots). Thus, reference to an element by the indefinite article "a" or "an" does not exclude the possibility that more than one of the element is present, unless the context clearly requires that there be one and only one of the elements. The indefinite article "a" or "an" thus usually means "at least one".

For the purpose of this invention, the "sequence identity" of two related nucleotide or amino acid sequences, expressed as a percentage, refers to the number of positions in the two optimally aligned sequences which have identical residues (×100) divided by the number of positions compared. A gap, i.e., a position in an alignment where a residue is present in one sequence but not in the other, is regarded as a position with non-identical residues. The "optimal alignment" of two sequences is found by aligning the two sequences over the entire length according to the Needleman and Wunsch global alignment algorithm (Needleman and Wunsch, 1970, J Mol Biol 48(3):443-53) in The European Molecular Biology Open Software Suite (EMBOSS, Rice et al., 2000, Trends in Genetics 16(6): 276-277; see e.g. world wide web at ebi.ac.uk/emboss/align/index.html) using default settings (gap opening penalty=10 (for nucleotides)/ 10 (for proteins) and gap extension penalty=0.5 (for nucleotides)/0.5 (for proteins)). For nucleotides the default scoring matrix used is EDNAFULL and for proteins the default scoring matrix is EBLOSUM62.

"Substantially identical" or "essentially similar", as used herein, refers to sequences, which, when optimally aligned as defined above, share at least a certain minimal percentage of sequence identity (as defined further below).

"Stringent hybridization conditions" can be used to identify nucleotide sequences, which are substantially identical to a given nucleotide sequence. Stringent conditions are sequence dependent and will be different in different circumstances. Generally, stringent conditions are selected to be about 5° C. lower than the thermal melting point ($T_m$) for the specific sequences at a defined ionic strength and pH. The $T_m$ is the temperature (under defined ionic strength and pH) at which 50% of the target sequence hybridizes to a perfectly matched probe. Typically stringent conditions will be chosen in which the salt concentration is about 0.02 molar at pH 7 and the temperature is at least 60° C. Lowering the salt concentration and/or increasing the temperature increases stringency. Stringent conditions for RNA-DNA hybridizations (Northern blots using a probe of e.g. 100 nt) are for example those which include at least one wash in 0.2×SSC at 63° C. for 20 min, or equivalent conditions.

"High stringency conditions" can be provided, for example, by hybridization at 65° C. in an aqueous solution containing 6×SSC (20×SSC contains 3.0 M NaCl, 0.3 M Na-citrate, pH 7.0), 5×Denhardt's (100×Denhardt's contains 2% Ficoll, 2% Polyvinyl pyrollidone, 2% Bovine Serum Albumin), 0.5% sodium dodecyl sulphate (SDS), and 20 μg/ml denaturated carrier DNA (single-stranded fish sperm DNA, with an average length of 120-3000 nucleotides) as non-specific competitor. Following hybridization, high stringency washing may be done in several steps, with a final wash (about 30 min) at the hybridization temperature in 0.2-0.1×SSC, 0.1% SDS.

"Moderate stringency conditions" refers to conditions equivalent to hybridization in the above described solution but at about 60-62° C. Moderate stringency washing may be done at the hybridization temperature in 1×SSC, 0.1% SDS.

"Low stringency" refers to conditions equivalent to hybridization in the above described solution at about 50-52° C. Low stringency washing may be done at the hybridization temperature in 2×SSC, 0.1% SDS. See also Sambrook et al. (1989) and Sambrook and Russell (2001).

"Increased harvested yield" or "increased seed or grain yield" refers to the larger amount of seed or grain harvested from a plurality of plants, each comprising mutant IND alleles according to the invention, when compared to the amount of seed or grain harvested from a similar number of isogenic plants without the mutant IND alleles. Yield is typically expressed in volume units of harvested seed per surface units, such as bushels/acre or kg/ha. The yield increase is typically expressed in percentage, whereby the yield of the reference or control plant is referred to as 100% and the yield of the plants according to the inventions is expressed in % relative to the yield of the control plant. Observed yield increases in *Brassica* plants according to the invention ranged from at least 101% to at least 124% and it is expected that higher yield increases are feasible. Yield increase may also range from 104% to 108% or 105% to 110%.

DETAILED DESCRIPTION

As described in WO09/068313 (claiming priority of European patent application EP 07023052), it was found before that *Brassica napus* plants, which are homozygous for a full knockout ind allele in only one of their two IND genes, i.e. in IND-A1 or IND-C1, did not show a significant increase in pod shatter resistance compared to *Brassica napus* plants not comprising mutant IND alleles, while in *Brassica napus* plants, which were homozygous for a full knockout ind allele in both IND genes, pod shatter resistance was significantly increased, but the level of pod shatter resistance was too high to maintain an agronomically relevant treshability. By contrast, pod shatter resistance was significantly increased in *Brassica napus* plants comprising three full knockout ind alleles of the two *Brassica napus* IND genes, to a level whereby the plants maintain an agronomically relevant treshability of the pods.

The inventors surprisingly found that *Brassica napus* plants with a pod shatter phenotype similar to the *Brassica* plants described in WO09/068313 (claiming priority of European patent application EP 07023052), i.e. which combine an increased pod shatter resistance with an agronomically relevant treshability of the pods, can also be obtained by combining two partial knock-out mutant IND alleles with two full knock-out mutant IND alleles instead of combining three full knockout mutant IND alleles. It was further found that mutations in the IND-C1 gene resulted in a stronger increase in pod shatter resistance than mutations in the IND-A1 gene. A stronger increase in pod shatter resistance in *Brassica napus* plants was, for example, observed when the two full knock-out mutant IND alleles were full knockout mutant IND alleles from the IND-C1 gene and the two partial knock-out mutant IND alleles were partial knock-out mutant IND alleles from the IND-A1 gene than when the two full knock-out mutant IND alleles were from the IND-A1 gene and the partial knock-out mutant IND alleles were from the IND-C1 gene. Surprisingly, *Brassica napus* plants which combine an increased pod shatter resistance with an agronomically relevant treshability of the pods could also be obtained by introducing two partial knock-out mutant IND alleles, in particular of the IND-C1 gene, alone.

Thus in one embodiment of the invention, a *Brassica* plant comprising at least two IND genes, in particular a *Brassica napus* plant comprising an IND-A1 and an IND-C1 gene, characterized in that it comprises two partial knock-out mutant IND alleles in its genome, in particular of an IND-A1 and/or an IND-C1 gene, preferably of an IND-C1 gene, is provided herein, whereby the ind alleles result in a significantly reduced amount of functional IND protein of the type encoded by the wild-type equivalent of these mutant alleles and thus an overall significantly reduced amount of the functional IND proteins produced in the plant cells, specifically in the developing seed pods, in vivo.

In another embodiment, the *Brassica* plant further comprises two full knock-out mutant IND alleles in its genome, in particular of an IND-C1 and/or an IND-A1 gene, respectively, preferably of an IND-C1 gene, such as those described in WO09/068313 (claiming priority of European patent application EP 07023052), e.g. ind-a1-ems01, ind-a1-ems05, ind-c1-ems01, or ind-c1-ems03, and the like.

It is thought that by combining sufficient copies of specific partial knock-out mutant IND alleles with sufficient copies of specific full knock-out mutant and/or wild type IND alleles in one plant, in particular a *Brassica* plant, it is possible to fine tune the amount and/or type of functional IND proteins made, which in turn influences the fruit dehiscence properties of the plant. The absolute and relative amount of the IND proteins can thus be tuned in such a way as to provide plants that produce sufficient IND protein(s) to enable an agronomically relevant treshability of the seed pods, while reducing seed shattering before or during harvest.

Thus in another embodiment of the invention, a plant, in particular a *Brassica* plant, is provided comprising at least one partial knock-out mutant IND allele, which encodes a partially functional IND protein, such as those described below, e.g. ind-a1-ems06, ind-a1-ems09, ind-a1-ems13, ind-c1-ems04, ind-c1-ems08, or ind-c1-ems09, and the like, while the remaining alleles may be partial knock-out, full knock-out and/or wild-type IND alleles.

In one aspect of the invention a *Brassica* plant comprising at least two IND genes, in particular a *Brassica napus* plant, comprising two partial knockout ind alleles and n-tuple full knockout ind alleles of the two IND genes in that *Brassica* plant, in particular of the *Brassica napus* IND-A1 and/or IND-C1 genes, preferably the IND-C1 gene, is provided, whereby n≤2 (e.g. n=0, 1, or 2), so that at least one allele produces at least partially functional IND protein.

In a further aspect of the invention an homozygous IND single mutant—(n=2, i.e. homozygous for a partial knockout mutant allele of one IND gene), and/or an homozygous IND double mutant—(n=4, i.e. homozygous for a full and/or a partial knockout mutant allele of two IND genes) plant of a *Brassica* species comprising at least two IND genes, in particular *Brassica napus*, is provided, whereby the mutant alleles are mutant alleles of the two IND genes in that *Brassica* plant, in particular of the IND-A1 and/or IND-C1 genes. Such mutant plants may, according to this invention, be used for breeding purposes.

Thus in one embodiment of the invention, an homozygous IND single partial knockout mutant *Brassica napus* plant is provided herein, wherein the genotype of the plant can be described as ind-a1$^P$/ind-a1$^P$, IND-C1/IND-C1, or IND-A1/IND-A1, ind-c1$^P$/ind-c1$^P$. In another embodiment of the invention, an homozygous IND double partial mutant *Brassica napus* plant is provided herein, wherein the genotype of the plant can be described as ind-a1"/ind-a1", ind-c1$^P$/ind-c1$^P$. In yet a further embodiment of the invention, an homozygous IND double partial and full mutant *Brassica napus* plant is provided herein, wherein the genotype of the plant can be described as or ind-a1$^F$/ind-a1$^F$, ind-c1$^P$/ind-c1$^P$ or ind-a1$^P$/ind-a1$^P$, ind-c1$^F$/ind-c1$^F$.

Further provided herein are novel nucleic acid sequences of partial knockout mutant IND genes/alleles from *Brassica* species, as well as the partial knockout mutant IND proteins. Also provided are methods of generating and combining partial knockout mutant IND alleles in *Brassica* plants, as well as *Brassica* plants and plant parts comprising specific combinations of full and partial knockout mutant IND alleles in their genome, whereby seed shattering is reduced in these plants. The use of these plants for transferring partial knockout mutant IND alleles to other plants is also an embodiment of the invention, as are the plant products of any of the plants described. In addition kits and methods for marker assisted selection (MAS) for combining or detecting IND genes and/or alleles are provided. Each of the embodiments of the invention is described in detail herein below.

The *Brassica* plants described herein which exhibit reduced or delayed seed shattering have an increase in the yield of harvested seed. However, it was observed that not only the harvested seed yield from *Brassica* plants comprising only the ind-c1-09 allele in homozygous state (that show an observable reduced or delayed seed shatter phenotype), but also the harvested seed yield from other *Brassica* plants comprising only two mutant IND alleles in homozygous state, i.e. wherein the genotype of the plant can be described as ind-a1$^P$/ind-a1$^P$, IND-C1/IND-C1, or IND-A1/IND-A1, ind-c1$^P$/ind-c1$^P$ was also significantly increased, when compared to isogenic *Brassica* plants not comprising the mutant IND alleles, despite the absence of an observable reduced or delayed seed shatter phenotype in the *Brassica* plants comprising the mutant IND alleles. The invention thus also provides *Brassica* plants comprising at least two IND genes, wherein at least two alleles produce a functional IND protein, which plants have a higher seed yield. It will be clear that the two mutant alleles at the IND-A locus or at the IND-C locus may be the same mutant allele or a different mutant allele.

Nucleic Acid Sequences According to the Invention

Provided are partial knockout mutant ind nucleic acid sequences encoding partially functional IND proteins, i.e. IND proteins with a significantly reduced biological activity (i.e., IND nucleic acid sequences comprising one or more mutations, which result in a significantly reduced biological activity of the encoded IND protein) of IND genes from Brassicaceae, particularly from *Brassica* species, especially from *Brassica napus*, but also from other *Brassica* crop species. For example, *Brassica* species comprising an A and/or a C genome may comprise alleles of IND-A1 or IND-C1 genes, which are essentially similar to the partial knockout mutant IND alleles of the present invention and which can be identified and combined in a single plant according to the invention. In addition, mutagenesis methods can be used to generate mutations in wild type IND alleles, thereby generating mutant ind alleles essentially similar to the partial knockout mutant IND alleles of the present invention for use according to the invention. Because specific IND alleles are preferably combined in a plant by crossing and selection, in one embodiment the ind nucleic acid sequences are provided within a plant (i.e. endogenously), e.g. a *Brassica* plant, preferably a *Brassica* plant which can be crossed with *Brassica napus* or which can be used to make a "synthetic" *Brassica napus* plant. Hybridization between different *Brassica* species is described in the art, e.g., as referred to in Snowdon (2007, Chromosome research 15: 85-95). Interspecific hybridization can, for example, be used to transfer genes from, e.g., the C genome in *B. napus* (AACC) to the C genome in *B. carinata* (BBCC), or even from, e.g., the C genome in *B. napus* (AACC) to the B genome in *B. juncea* (AABB) (by the sporadic event of illegitimate recombination between their C and B genomes). "Resynthesized" or "synthetic" *Brassica napus* lines can be produced by crossing the original ancestors, *B. oleracea* (CC) and *B. rapa* (AA). Interspecific, and also intergeneric, incompatibility barriers can be successfully overcome in crosses between *Brassica* crop species and their relatives, e.g., by embryo rescue techniques or protoplast fusion (see e.g. Snowdon, above).

However, isolated ind nucleic acid sequences (e.g. isolated from the plant by cloning or made synthetically by DNA synthesis), as well as variants thereof and fragments of any of these are also provided herein, as these can be used to determine which sequence is present endogenously in a plant or plant part, whether the sequence encodes a functional, a partially functional, a non-functional or no protein (e.g. by expression in a recombinant host cell as described below) and for selection and transfer of specific alleles from one plant into another, in order to generate a plant having the desired combination of partial and/or full knockout mutant IND alleles.

Novel partial knockout mutant IND nucleic acid sequences of wild-type IND A1 and IND-C1 have been isolated from *Brassica napus*. The wild type IND sequences as described in WO09/068313 (claiming priority of European patent application EP 07023052) are depicted in SEQ ID NO: 1, SEQ ID NO: 3, SEQ ID NO: 5 and SEQ ID NO: 7 of the sequence listing, while the novel partial knockout mutant ind sequences of these sequences, and of sequences essentially similar to these, are described herein below and in the Examples, with reference to the wild type IND sequences. The genomic IND protein-encoding DNA from *Brassica napus* does not comprise any introns.

"IND-A1 nucleic acid sequences" or "IND-A1 variant nucleic acid sequences" according to the invention are nucleic acid sequences encoding an amino acid sequence having at least 75%, at least 80%, at least 85%, at least 90%, at least 95%, 98%, 99% or 100% sequence identity with SEQ ID NO: 2 or nucleic acid sequences having at least 80%, at least 85%, at least 90%, at least 95%, 96%, 97%, 98%, 99% or 100% sequence identity with SEQ ID NO: 1 or SEQ ID NO: 5. These nucleic acid sequences may also be referred to as being "essentially similar" or "essentially identical" to the IND sequences provided in the sequence listing.

"IND-C1 nucleic acid sequences" or "IND-C1 variant nucleic acid sequences" according to the invention are nucleic acid sequences encoding an amino acid sequence having at least 75%, at least 80%, at least 85%, at least 90%, at least 95%, 98%, 99% or 100% sequence identity with SEQ ID NO: 4 (IND-C1-long) or with SEQ ID NO: 4 from the amino acid at position 16 to the amino acid at position 210 (IND-C1-short) or nucleic acid sequences having at least 80%, at least 85%, at least 90%, at least 95%, 96%, 97%, 98%, 99% or 100% sequence identity with SEQ ID NO: 3 (IND-C1-long), with SEQ ID NO:3 from the nucleotide at position 46 to the nucleotide at position 633 (IND-C1-short) or with SEQ ID NO: 7. These nucleic acid sequences may also be referred to as being "essentially similar" or "essentially identical" to the IND sequences provided in the sequence listing.

Thus the invention provides novel partial knockout mutant nucleic acid sequences of nucleic acid sequences encoding wild type, functional IND-A1 and IND-C1 proteins, including variants and fragments thereof (as defined further below), whereby the mutation in the nucleic acid sequence preferably results in one or more amino acids being inserted, deleted or substituted in comparison to the wild type IND protein, in particular in one or more amino acids being substituted, and whereby the biological activity of the IND protein is significantly reduced. A significant reduction in the biological activity of the IND protein refers herein to a reduction in the DNA binding activity, the dimerization capacity and/or transcriptional regulating activity of the IND protein, such that the pod shatter resistance of a plant expressing the mutant IND protein is increased as compared to a plant expressing the corresponding wild type IND protein.

To determine the functionality of a specific IND allele/protein in plants, particularly in *Brassica* plants, the level of resistance to pod shattering in the plants can be determined by performing macroscopical, microscopical and histological assays on fruits and flowers of the plants comprising the specific IND allele/protein and of corresponding wild type plants analogous to the assays performed on *Arabidopsis* fruits and flowers as described by Liljegren et al. (2004, supra) or as described in the Examples below. Briefly, changes in pod shatter resistance can be evaluated and/or measured, e.g., by macroscopical tests, such as inspection of the seed pods with naked eye to evaluate, e.g., the presence or absence of the valve margins, the length of the beak of the pods, etc.; a Manual Impact Test (MIT) to compare the level of pod shatter resistance between different mutant IND lines and corresponding wild type lines by evaluating the ease of pod opening upon gently twisting the pods; a Random Impact Test (RIT) to compare the treshability of seed pods from plants from different mutant IND lines and corresponding wild type lines, respectively, by measuring the half-life of pod samples of these lines; and/or by microscopic tests to examine, e.g., whether and how cells at the valve margin and the dehiscence zone of seed pods are affected by mutations in IND. Once the dimerization partner of the IND protein (e.g., the IND protein itself in case its functioning depends on the formation of an homodimer or another protein in case its functioning depends on the formation of an heterodimer) and/or the gene(s) the transcription of which is regulated by the IND protein are identified and characterized, the functionality of a specific IND allele/protein can alternatively be evaluated by recombinant DNA techniques as known in the art, e.g., by co-expressing both partners of the dimer in a host cell (e.g. a bacterium, such as *E. coli*) and evaluating if dimers can still be formed, if the dimers can still bind to the bHLH binding site of the regulated gene(s), and/or if the transcription of these gene(s) is still regulated by this binding.

Both endogenous and isolated nucleic acid sequences are provided herein. Also provided are fragments of the mutant IND sequences and mutant IND variant nucleic acid sequences defined above, for use as primers or probes and as components of kits according to another aspect of the invention (see further below). A "fragment" of an ind nucleic acid sequence or variant thereof (as defined) may be of various lengths, such as at least 10, 12, 15, 18, 20, 50, 100, 200, 500, 600 contiguous nucleotides of the IND or ind sequence (or of the variant sequence).

Nucleic Acid Sequences Encoding Functional IND Proteins

The nucleic acid sequences depicted in the sequence listing encode wild type, functional IND proteins from *Brassica napus*. Thus, these sequences are endogenous to the *Brassica napus* plants from which they were isolated. Other *Brassica* crop species, varieties, breeding lines or wild accessions may be screened for other IND alleles, encoding the same IND proteins or variants thereof. For example, nucleic acid hybridization techniques (e.g. Southern blot analysis, using for example stringent hybridization conditions) or PCR-based techniques may be used to identify IND alleles endogenous to other *Brassica* plants, such as various *Brassica napus* varieties, lines or accessions, but also *Brassica juncea* (especially IND alleles on the A-genome), *Brassica carinata* (especially IND alleles on the C-genome) and *Brassica rapa* (A-genome) and *Brassica oleracea* (C-genome) plants, organs and tissues can be screened for other wild type IND alleles. To screen such plants, plant organs or tissues for the presence of IND alleles, the IND nucleic acid sequences provided in the sequence listing, or variants or fragments of any of these, may be used. For example whole sequences or fragments may be used as probes or primers. For example specific or degenerate primers may be used to amplify nucleic acid sequences encoding IND proteins from the genomic DNA of the plant, plant organ or tissue. These IND nucleic acid sequences may be isolated and sequenced using standard molecular biology techniques. Bioinformatics analysis may then be used to characterize the allele(s), for example in order to determine which IND allele the sequence corresponds to and which IND protein or protein variant is encoded by the sequence.

Whether a nucleic acid sequence encodes a functional IND protein can be analyzed by recombinant DNA techniques as known in the art, e.g., by a genetic complementation test using, e.g., an *Arabidopsis* plant, which is homozygous for a full knock-out ind mutant allele or a *Brassica napus* plant, which is homozygous for a full knock-out ind mutant allele of both the IND-A1 and IND-C1 gene.

In addition, it is understood that IND nucleic acid sequences and variants thereof (or fragments of any of these) may be identified in silico, by screening nucleic acid databases for essentially similar sequences. Likewise, a nucleic acid sequence may be synthesized chemically. Fragments of nucleic acid molecules according to the invention are also provided, which are described further below. Fragments include nucleic acid sequences encoding only the bHLH domain, or smaller fragments comprising part of the bHLH domain, such as the basic domain or the HLH domain, etc.

Nucleic Acid Sequences Encoding Mutant IND Proteins

The invention provides nucleic acid sequences comprising one or more nucleotide deletions, insertions or substitutions relative to the wild type IND nucleic acid sequences depicted in SEQ ID NO: 1, 3, 5 and 7 of the sequence listing, wherein the mutation(s) in the nucleic acid sequence result in a significantly reduced biological activity, i.e. a partial knockout of the biological activity, of the encoded IND protein relative to the wild type IND protein, as well as fragments of such mutant nucleic acid molecules. Such mutant nucleic acid sequences (referred to as ind$^P$ sequences) can be generated and/or identified using various known methods, as described further below. Again, such nucleic acid molecules are provided both in endogenous form and in isolated form.

Basically, any mutation in the wild type IND nucleic acid sequences which results in an IND protein comprising at least one amino acid insertion, deletion and/or substitution relative to the wild type IND protein can lead to significantly reduced or no biological activity. It is, however, understood that certain mutations in the IND protein are more likely to result in a complete abolishment of the biological activity of the IND protein, such as mutations whereby significant portions of the functional domains, such as the DNA binding domain ('b'), the dimerization domain ('HLH') and/or transcription regulating domains, are lacking, or whereby certain critical amino acid residues within these domains, such as the Gln (Q), Ala (A) and Arg (R) amino acids at position 5, 9, and 13 or the basic amino acid residues (in particular Arg (R) residues) at positions 10 and 12 of the consensus bHLH domain sequence defined by Heim et al. (2003, Mol Biol Evol 20, 735-747; corresponding to positions 123, 127 and 131, and 128 and 130, respectively, in SEQ ID NO: 10, see Table 1) are lacking or are substituted, preferably by non-similar or non-conservative amino acids, while other mutations in the IND protein are more likely to result in a significant reduction of the biological activity of the IND protein, such as mutations leading to substitutions of specific amino acids, e.g. the conserved amino acids indicated in Table 1, causing a less efficient DNA binding, a less efficient dimerization, and/or a less efficient regulation of transcription without completely abolishing the biological activity of the encoded IND protein. WO09/068313 (claiming priority of European patent application EP 07023052) describes, for example, full knockout mutant IND alleles, in particular ind-a1-ems01, ind-c1-ems01 and ind-c1-ems03, comprising a nonsense mutation resulting in the production of truncated IND proteins lacking the bHLH domain, and full knockout mutant IND alleles, in particular ind-a1-ems05, encoding a mutant IND protein in which the conserved Arg at position 10 of the consensus bHLH domain is substituted for an aromatic His, while the present invention describes partial knockout mutant IND alleles, in particular, e.g., ind-c1-ems09, encoding a mutant IND protein in which the conserved Ala at position 9 of the consensus bHLH domain is substituted for a Thr, and ind-c1-ems04, encoding a mutant IND protein in which the conserved Arg at position 12 of the consensus bHLH domain is substituted for a Cys.

The nucleic acid molecules may comprise one or more mutations, such as:

a "missense mutation", which is a change in the nucleic acid sequence that results in the substitution of an amino acid for another amino acid;

a "nonsense mutation" or "STOP codon mutation", which is a change in the nucleic acid sequence that results in the introduction of a premature STOP codon and thus the termination of translation (resulting in a truncated protein); plant genes contain the translation stop codons "TGA" (UGA in RNA), "TAA" (UAA in RNA) and "TAG" (UAG in RNA); thus any nucleotide substitution, insertion, deletion which results in one of these codons to be in the mature mRNA being translated (in the reading frame) will terminate translation;

an "insertion mutation" of one or more amino acids, due to one or more codons having been added in the coding sequence of the nucleic acid;

a "deletion mutation" of one or more amino acids, due to one or more codons having been deleted in the coding sequence of the nucleic acid;

a "frameshift mutation", resulting in the nucleic acid sequence being translated in a different frame downstream of the mutation. A frameshift mutation can have various causes, such as the insertion, deletion or duplication of one or more nucleotides.

Table 1 indicates the length of the *Arabidopsis* IND protein in SEQ ID NO: 10, of the Arabidopsis IND coding DNA in SEQ ID NO: 9, and of the *Brassica napus* IND-A1 and IND-C1 proteins in SEQ ID NO: 2 and 6 and SEQ ID NO: 4 and 8, respectively; the position of the bHLH domains in the *Brassica napus* IND-A1 and IND-C1 proteins based on the indicated position of pfam domain PF00010, smart domain SM00353, prosite domain PS50888 and superfam domain G3D.4.10.280.10 or SSF47459 of the Arabidopsis IND protein according to The *Arabidopsis* Information Resource (TAIR) database world wide web at arabidopsis.org/; locus At4g00120.1, herein incorporated by reference; SEQ ID NO: 10); the position of the bHLH domains and conserved amino acids in the *Brassica napus* IND-A1 and IND-C1 proteins based on the indicated position of the bHLH domain and conserved amino acids in *Arabidopsis* IND protein according to Heim et al. (2003, Mol Biol Evol 20, 735-747), according to Toledo-Ortiz et al. (2003, Plant Cell 15: 1749-1770), and according to Liljegren et al. (2004, Cell, 116, 843-853), herein incorporated by reference; as further described in WO09/068313 (claiming priority of European patent application EP 07023052), which is herein incorporated by reference.

TABLE 1

IND proteins-amino acids (AA) regions and positions

| | | AtIND1 (SEQ ID NO: 10) | AtIND1 (SEQ ID NO: 9) | BnIND-A1 (SEQ ID NO: 2/6) | BnIND-C1a/b (SEQ ID 4/8 from 16-210/SEQ ID 4/8) |
|---|---|---|---|---|---|
| Coding region | TAIR: | 1-198 (198 AA) | 1-594 | 1-185 (185 AA) | 16-210/1-210 (195/210 AA) |
| | PF00010 | 121-168 | 361-504 | 120-167 | 133-180 |
| | SM00353 | 124-173 | 370-519 | 123-172 | 136-185 |
| | PS50888 | 112-168 | 334-504 | 111-167 | 124-180 |
| | G3D.4.10.280.10 | 114-196 | 340-588 | — | 127-208 |
| | SSF47459 | 114-198 | 340-594 | — | 127-210 |
| | Liljegren et al. | 30-198 (169 AA) | 88-594 | | |
| bHLH: | Heim et al. | 119-174 | 355-523 | 118-173 | 131-186 |
| | Toledo-Ortiz et al. | 115-167 | 343-501 | 114-166 | 127-179 |
| | Liljegren et at | 119-167 | 355-501 | 118-166 | 131-179 |
| b | Heim et al. | 119-131 | 355-393 | 118-132 | 131-145 |
| | Toledo-Ortiz et al. | 115-131 | 343-393 | 114-132 | 127-145 |
| | Liljegren et al. | 119-131 | 355-393 | 118-132 | 131-145 |
| H1 | Heim et al. | 132-146 | 394-438 | 133-145 | 146-158 |
| | Toledo-Ortiz et al. | 132-146 | 394-438 | 133-145 | 146-158 |
| | Liljegren et al. | 132-145 | 394-435 | 133-144 | 146-157 |
| L | Heim et al. | 147-152 | 439-456 | 146-151 | 159-164 |
| | Toledo-Ortiz et al. | 147-152 | 439-456 | 146-151 | 159-164 |
| | Liljegren et al. | 146-152 | 436-456 | 145-151 | 158-164 |
| H2 | Heim et al. | 153-174 | 457-523 | 152-173 | 165-186 |
| | Toledo-Ortiz et al. | 153-167 | 457-501 | 152-166 | 165-179 |
| | Liljegren et al. | 153-167 | 457-501 | 152-166 | 165-179 |

TABLE 1-continued

IND proteins-amino acids (AA) regions and positions

| | | AtIND1 (SEQ ID NO: 10) | AtIND1 (SEQ ID NO: 9) | BnIND-A1 (SEQ ID NO: 2/6) | BnIND-C1a/b (SEQ ID 4/8 from 16-210/SEQ ID 4/8) |
|---|---|---|---|---|---|
| Conserved AA | N (1$^T$) | 115 | 343-345 | 114 | 127 |
| | V (2$^T$) | 116 | 346-348 | 115 | 128 |
| | Q (5$^H$) | 123 | 367-379 | 122 | 135 |
| | A (9$^H$-13$^T$) | 127 | 379-381 | 126 | 139 |
| | R (10$^H$-14$^T$) | 128 | 382-384 | 127 | 140 |
| | R (12$^H$-16$^T$) | 130 | 388-390 | 129 | 142 |
| | R (13$^H$) | 131 | 391-393 | 130 | 143 |
| | I (16$^H$-20$^T$) | 134 | 400-403 | 133 | 146 |
| | S (21$^T$) | 135 | 404-406 | 134 | 147 |
| | I (20$^H$-24$^T$) | 138 | 412-414 | 137 | 150 |
| | L (23$^H$-27$^T$) | 141 | 421-423 | 140 | 153 |
| | K (28$^T$) | 142 | 424-426 | 141 | 154 |
| | V (27$^H$) | 145 | 433-435 | 144 | 157 |
| | K (39$^T$) | 150 | 448-450 | 149 | 162 |
| | T (42$^T$) | 153 | 460-463 | 152 | 165 |
| | A (36$^H$) | 154 | 460-462 | 153 | 166 |
| | M (45$^T$) | 156 | 466-468 | 155 | 168 |
| | L (39$^H$-46$^T$) | 157 | 469-471 | 156 | 169 |
| | A (49$^T$) | 160 | 478-480 | 159 | 172 |
| | I (43$^H$-50$^T$) | 161 | 481-483 | 160 | 173 |
| | Y (52$^T$) | 163 | 487-489 | 162 | 175 |
| | T (53$^T$) | 164 | 490-492 | 163 | 176 |
| | L (49$^H$-56$^T$) | 167 | 499-501 | 166 | 179 |
| | V (53$^H$) | 171 | 511-513 | 170 | 183 |
| | L (56$^H$) | 174 | 580-582 | 173 (A) | 186 |
| At ind | ind-5 (W13 > STOP)$^L$ | 42 | 124-126 | 25 | 41 |
| | ind-2 (A26 > FS)$^L$ | 55 | 163-165 | — | — |
| | ind-6$^W$ | Insertion after 61 | Insertion after 185 | — | — |
| | ind-4 (Q63 > STOP)$^L$ | 92 | 274-276 | 91 | 104 |
| | ind-3 (R99 > H)$^L$ | 128 | 382-384 | 127 | 140 |
| | ind-1 (L112 > F)$^L$ | 141 | 421-423 | 140 | 153 |

Heim et al., $^H$Heim et al., 2003, Mol Biol Evol 20, 735-747;
Toledo-Ortiz et al., $^T$Toledo-Ortiz et al., 2003, Plant Cell 15: 1749-1770;
Liljegren et al., $^L$Liljegren et al., 2004, Cell, 116, 843-853;
$^W$Wu et al., 2006, Planta 224, 971-979.

Optimal alignment of the *Arabidopsis* IND nucleic acid (SEQ ID NO: 9) and amino acid (SEQ ID NO: 10) sequences with IND nucleic acid sequences, in particular the *Brassica* IND nucleic acid (SEQ ID NO: 1 and 3) and amino acid (SEQ ID NO: 2 and 4) sequences of the present invention, allows to determine the positions of the corresponding conserved domains and amino acids in these *Brassica* sequences (see Table 1 for the *Brassica* IND sequences of SEQ ID NO: 1 to 4).

Thus in one embodiment, partial knockout mutant IND nucleic acid sequences comprising one or more of any of the types of mutations described above are provided. In another embodiment, partial knockout ind sequences comprising one or more stop codon (nonsense) mutations, one or more missense mutations and/or one or more frameshift mutations are provided. Any of the above mutant nucleic acid sequences are provided per se (in isolated form), as are plants and plant parts comprising such sequences endogenously. In the tables herein below the most preferred ind alleles are described and seed deposits of *Brassica napus* seeds comprising one or more ind alleles have been deposited as indicated.

A nonsense mutation in an IND allele, as used herein, is a mutation in an IND allele whereby one or more translation stop codons are introduced into the coding DNA and the corresponding mRNA sequence of the corresponding wild type IND allele. Translation stop codons are TGA (UGA in the mRNA), TAA (UAA) and TAG (UAG). Thus, any mutation (deletion, insertion or substitution) that leads to the generation of an in-frame stop codon in the coding sequence will result in termination of translation and truncation of the amino acid chain. In one embodiment, a partial knockout mutant IND allele is provided comprising a nonsense mutation wherein an in-frame stop codon is introduced in the IND codon sequence by a single nucleotide substitution, such as the mutation of CAG to TAG, TGG to TAG, TGG to TGA, or CAA to TAA. In another embodiment, a partial knockout mutant IND allele is provided comprising a nonsense mutation wherein an in-frame stop codon is introduced in the IND codon sequence by double nucleotide substitutions, such as the mutation of CAG to TAA, TGG to TAA, or CGG to TAG or TGA. In yet another embodiment, a partial knockout mutant IND allele is provided comprising a nonsense mutation wherein an in-frame stop codon is introduced in the IND codon sequence by triple nucleotide substitutions, such as the mutation of CGG to TAA. The truncated protein lacks the amino acids encoded by the coding DNA downstream of the mutation (i.e. the C-terminal part of the IND protein) and maintains the amino acids encoded by the coding DNA upstream of the mutation (i.e. the N-terminal part of the IND protein). In one embodiment, a partial knockout mutant IND allele is provided comprising a nonsense mutation present anywhere in front of the conserved Leu residue of the H2 domain (at position 56 in the consensus bHLH domain sequence as described by Heim et al., 2003, see Table 1), so that at least the conserved Leu residue is lacking. The more truncated the mutant IND protein is in comparison to the wild type IND protein, the more the truncation may result in a significantly reduced activity of the IND protein. It is believed that, in order for the mutant IND protein to retain some biological activity, it should at least comprise the DNA binding (b) domain. Thus in another embodiment, a partial knockout mutant IND allele is provided comprising a nonsense mutation which results in a truncated protein of less than about 170 amino acids (lacking the conserved Leu), less than about 150 amino acids (lacking the H2 domain), less than about 145 amino acids (lacking the L and H2 domains), or less than about 130 amino acids (lacking the HLH domain)(see Table 1).

The Tables herein below describe a range of possible nonsense mutations in the *Brassica napus* IND sequences provided herein:

TABLE 2a

Potential STOP codon mutations in IND-A1 ( SEQ ID NO: 1)

| Amino acid position | Nucleotide position | Wild type → mutant codon | Wild type → mutant amino acid |
|---|---|---|---|
| 25 | 74 | tgg → tag | TRP → STOP |
|  | 75 | tgg → tga | TRP → STOP |
|  | 74 + 75 | tgg → taa | TRP → STOP |
| 57 | 169 | cag → tag | GLN → STOP |
|  | 169 + 171 | cag → taa | GLN → STOP |
| 91 | 271 | caa → taa | GLN → STOP |
| 98 | 292 | cag → tag | GLN → STOP |
|  | 292 + 294 | cag → taa | GLN → STOP |
| 122 | 364 | cag → tag | GLN → STOP |
|  | 364 + 366 | cag → taa | GLN → STOP |
| 128 | 382 + 383 | cgg → tag | ARG → STOP |
|  | 382 + 384 | cgg → tga | ARG → STOP |
|  | 382 + 383 + 384 | cgg → taa | ARG → STOP |
| 138 | 412 + 413 | cgg → tag | ARG → STOP |
|  | 412 + 414 | cgg → tga | ARG → STOP |
|  | 412 + 413 + 414 | cgg → taa | ARG → STOP |

TABLE 2a-continued

Potential STOP codon mutations in IND-A1 ( SEQ ID NO: 1)

| Amino acid position | Nucleotide position | Wild type → mutant codon | Wild type → mutant amino acid |
|---|---|---|---|
| 168 | 502 + 503 | cgg → tag | ARG → STOP |
|  | 502 + 504 | cgg → tga | ARG → STOP |
|  | 502 + 503 + 504 | cgg → taa | ARG → STOP |
| 169 | 505 | cag → tag | GLN → STOP |
|  | 505 + 507 | cag → taa | GLN → STOP |
| 181 | 542 | tgg → tag | TRP → STOP |
|  | 543 | tgg → tga | TRP → STOP |
|  | 542 + 543 | tgg → taa | TRP → STOP |

TABLE 2b

Potential STOP codon mutations in IND-C1 (SEQ ID NO: 3)

| Amino acid position | Nucleotide position | Wild type → mutant codon | Wild type → mutant amino acid |
|---|---|---|---|
| 41 | 122 | tgg → tag | TRP → STOP |
|  | 123 | tgg → tga | TRP → STOP |
|  | 122 + 123 | tgg → taa | TRP → STOP |
| 50 | 148 | caa → taa | GLN → STOP |
| 73 | 271 | cag → tag | GLN → STOP |
|  | 271 + 272 | cag → taa | GLN → STOP |
| 104 | 310 | caa → taa | GLN → STOP |
| 111 | 331 | cag → tag | GLN → STOP |
|  | 331 + 333 | cag → taa | GLN → STOP |
| 135 | 403 | cag → tag | GLN → STOP |
|  | 403 + 405 | cag → taa | GLN → STOP |
| 141 | 421 + 422 | cgg → tag | ARG → STOP |
|  | 421 + 423 | cgg → tga | ARG → STOP |
|  | 421 + 422 + 423 | cgg → taa | ARG → STOP |
| 151 | 451 + 452 | cgg → tag | ARG → STOP |
|  | 451 + 453 | cgg → tga | ARG → STOP |
|  | 451 + 452 + 453 | cgg → taa | ARG → STOP |
| 181 | 541 + 542 | cgg → tag | ARG → STOP |
|  | 541 + 543 | cgg → tga | ARG → STOP |
|  | 541 + 542 + 543 | cgg → taa | ARG → STOP |
| 182 | 544 | cag → tag | GLN → STOP |
|  | 544 + 546 | cag → taa | GLN → STOP |
| 187 | 559 | cag → tag | GLN → STOP |
|  | 559 + 561 | cag → taa | GLN → STOP |
| 191 | 571 | cag → tag | GLN → STOP |
|  | 571 + 573 | cag → taa | GLN → STOP |

Obviously, mutations are not limited to the ones shown in the above tables and it is understood that analogous STOP mutations may be present in ind alleles other than those depicted in the sequence listing and referred to in the tables above.

A missense mutation in an IND allele, as used herein, is any mutation (deletion, insertion or substitution) in an IND allele whereby one or more codons are changed into the coding DNA and the corresponding mRNA sequence of the corresponding wild type IND allele, resulting in the substitution of one or more amino acids in the wild type IND protein for one or more other amino acids in the mutant IND protein. In one embodiment, a partial knockout mutant IND allele is provided comprising a missense mutation resulting in a substitution of a valine (Val) residue at position 124 of the IND protein in SEQ ID NO: 2, or a sequence essentially similar thereto, in particular by a methionine (Met) residue, such as the ind-a1-EMS06 allele (Table 3a). In another embodiment, a partial knockout mutant IND allele is provided comprising a missense mutation resulting in a substitution of a glycine (Gly) residue at position 146 of the IND protein in SEQ ID NO: 2, or a sequence essentially similar thereto, in particular by a serine (Ser) residue, such as the ind-a1-EMS09 allele (Table 3a). In yet another embodiment, a partial knockout mutant IND allele is provided comprising a missense mutation resulting in a substitution of an alanine (Ala) residue at position 159 of the IND protein in SEQ ID NO: 2, or a sequence essentially similar thereto, in particular by a valine (Val) residue, such as the ind-a1-EMS 13 allele (Table 3a). In still another embodiment, a partial knockout mutant IND allele is provided comprising a missense mutation resulting in a substitution of a threonine (Thr) residue at position 136 of the IND protein in SEQ ID NO: 4, or a sequence essentially similar thereto, in particular by a methionine (Met) residue, such as the ind-c1-EMS08 allele (Table 3b). In a further embodiment, a partial knockout mutant IND allele is provided comprising a missense mutation resulting in a substitution of an alanine (Ala) residue at position 139 of the IND protein in SEQ ID NO: 4, or a sequence essentially similar thereto, in particular by a threonine (Thr) residue, such as the ind-c1-EMS09 allele (Table 3b). In still a further embodiment, a partial knockout mutant IND allele is provided comprising a missense mutation resulting in a substitution of an arginine (Arg) residue at position 142 of the IND protein in SEQ ID NO: 4, or a sequence essentially similar thereto, in particular by a cysteine (Cys) residue, such as the ind-c1-EMS04 allele (Table 3b). Reference seed comprising ind-a1-EMS06, ind-a1-EMS09, ind-a1-EMS13, ind-c1-EMS08, ind-c1-EMS09, and ind-c1-EMS04 alleles in homozygous state have been deposited at the NCIMB Limited (Ferguson Building, Craibstone Estate, Bucksburn, Aberdeen, Scotland, AB21 9YA, UK) on Jul. 7, 2008, under accession number NCIMB 41570, NCIMB 41571, NCIMB 41572, NCIMB 41573, NCIMB 41574, and NCIMB 41575, respectively.

07023052), some of the conserved amino acids are more critical for the biological activity of the IND protein than others. Thus, for example, missense mutations which result in the substitution of, e.g., the amino acids at position 5, 9 (e.g., ind-c1-EMS09), and 13 or at positions 10 (e.g., ind-a1-EMS05) and 12 (e.g., ind-c1-EMS04) of the consensus bHLH domain sequence defined by Heim et al. (supra) are more likely to result in a significantly reduced activity, due to a reduced ability to bind to the target DNA, of the IND protein. Similarly missense mutations which result in the substitution of, e.g., the amino acids at position 16, 20, 23, 27 in helix1 or at positions 36, 39, 43, 49 (e.g., ind-a1-EMS13), 53, and 56 in helix2 of the consensus bHLH domain sequence defined by Heim et al. (supra) are more likely to result in a significantly reduced activity, due to a reduced dimerization ability, of the IND protein.

In still another embodiment, a partial knockout mutant IND allele comprising a missense mutation which can be used according to the invention is an IND allele comprising a missense mutation corresponding to the missense mutation in the *Arabidopsis* partial knockout ind-1 (Liljegren et al., 2004, supra) alleles (see Table 1).

A frameshift mutation in an IND allele, as used herein, is a mutation (deletion, insertion, duplication, and the like) in an IND allele that results in the nucleic acid sequence being translated in a different frame downstream of the mutation.

Amino Acid Sequences According to the Invention

Provided are partial knockout mutant IND amino acid sequences (i.e., IND amino acid sequences comprising one or more mutations, which result in a significantly reduced biological activity of the IND protein) from Brassicaceae, particularly from *Brassica* species, especially from *Brassica*

TABLE 3a

Missense mutations in IND-A1

| Amino acid position | Nucleotide position | | Wild type → mutant codon | Wild type → mutant amino acid | Allele name | Deposit number |
|---|---|---|---|---|---|---|
| SEQ ID: 2/6 | SEQ ID: 1 | SEQ ID: 5 | | | | |
| 124 | 370 | 930 | gtg → atg | VAL → MET | ind-a1-EMS06 | NCIMB 41570 |
| 146 | 436 | 996 | ggc → agc | GLY → SER | ind-a1-EMS09 | NCIMB 41571 |
| 159* | 476 | 1036 | gcc → gtc | ALA → VAL | ind-a1-EMS13 | NCIMB 41572 |

TABLE 3b

Missense mutations in IND-C1

| Amino acid position | Nucleotide position | | Wild type → mutant codon | Wild type → mutant amino acid | Allele name | Deposit number |
|---|---|---|---|---|---|---|
| SEQ ID: 4/8 | SEQ ID: 3 | SEQ ID: 7 | | | | |
| 136 | 407 | 903 | acg → atg | THR → MET | ind-c1-EMS08 | NCIMB 41573 |
| 139* | 415 | 911 | gct → act | ALA → THR | ind-c1-EMS09 | NCIMB 41574 |
| 142* | 424 | 920 | cgt → tgt | ARG → CYS | ind-c1-EMS04 | NCIMB 41575 |

In another embodiment, a partial knockout mutant IND allele comprising a missense mutation is provided encoding an IND protein wherein one or more of the conserved amino acids indicated above or in Table 1 is/are substituted, such as partial knockout mutant IND alleles ind-a1-EMS13, ind-c1-EMS04 and ind-c1-EMS09 (indicated with * in Table 3). As described in Heim et al. (2003, Mol Biol Evol 20, 735-747), Toledo-Ortiz et al. (2003, Plant Cell 15: 1749-1770), Liljegren et al. (2004, Cell, 116, 843-853), and WO09/068313 (claiming priority of European patent application EP

*napus*, but also from other *Brassica* crop species. For example, *Brassica* species comprising an A and/or a C genome may encode different IND-A1 or IND-C1 amino acids, which are essentially similar to the novel partial knockout mutant IND proteins of the present invention. In addition, mutagenesis methods can be used to generate mutations in wild type IND alleles, thereby generating mutant alleles which can encode further mutant IND proteins, which are essentially similar to the partial knockout mutant IND proteins of the present invention. In one embodiment the mutant IND amino acid sequences are provided within a *Brassica* plant (i.e. endogenously). However, isolated IND amino acid sequences (e.g. isolated from the plant or made synthetically), as well as variants thereof and fragments of any of these are also provided herein.

Amino acid sequences, which are essentially similar to the novel partial knockout mutant IND proteins of the present invention can be obtained by replacing amino acids in the partial knockout IND amino acid sequences of the present invention by other amino acids having similar properties (such as similar hydrophobicity, hydrophilicity, antigenicity, propensity to form or break α-helical structures or β-sheet structures). Conservative substitution tables are well known in the art (see for example Creighton (1984) Proteins. W.H. Freeman and Company and Table 4 of the present patent application).

TABLE 4

Examples of conserved amino acid substitutions

| Residue | Conservative Substitutions |
|---|---|
| Ala | Ser |
| Arg | Lys |
| Asn | Gln, His |
| Asp | Glu |
| Gln | Asn |
| Cys | Ser |
| Glu | Asp |
| Gly | Pro |
| His | Asn, Gln |
| Ile | Leu, Val |
| Leu | Ile, Val |
| Lys | Arg, Gln |
| Met | Leu, Ile |
| Phe | Met, Leu, Tyr |
| Ser | Thr, Gly |
| Thr | Ser, Val |
| Trp | Tyr |
| Tyr | Trp, Phe |
| Val | Ile, Leu |

Novel partial knockout mutant IND amino acid sequences of wild-type IND-A1 and IND-C1 proteins have been isolated from *Brassica napus*. The wild type IND sequences as described in WO09/068313 (claiming priority of European patent application EP 07023052) are depicted in SEQ ID NO: 2 and SEQ ID NO: 4, while the novel partial knockout mutant IND sequences of these sequences, and of sequences essentially similar to these, are described herein below and in the Examples, with reference to the wild type IND sequences. As described above, the wildtype IND proteins of *Brassica napus* are about 185-210 amino acids in length and comprise a number of structural and functional domains.

"IND-A1 amino acid sequences" or "IND-A1 variant amino acid sequences" according to the invention are amino acid sequences having at least 75%, at least 80%, at least 85%, at least 90%, at least 95%, 98%, 99% or 100% sequence identity with SEQ ID NO: 2. These amino acid sequences may also be referred to as being "essentially similar" or "essentially identical" to the IND sequences provided in the sequence listing.

"IND-C1 amino acid sequences" or "IND-C1 variant amino acid sequences" according to the invention are amino acid sequences having at least 75%, at least 80%, at least 85%, at least 90%, at least 95%, 96%, 97%, 98%, 99% or 100% sequence identity with SEQ ID NO: 4 (IND-C1-long) or with SEQ ID NO:4 from the amino acid at position 16 to the amino acid at position 210 (IND-C1-short). These amino acid sequences may also be referred to as being "essentially similar" or "essentially identical" the IND sequences provided in the sequence listing.

Thus, the invention provides novel partial knockout mutant sequences of amino acid sequences of wild type, functional IND-A1 and IND-C1 proteins, including variants and fragments thereof (as defined further below), whereby the mutation in the amino acid sequence preferably results in a significant reduction in the biological activity of the IND protein as compared to the biological activity of the corresponding wild type IND protein. A significant reduction in the biological activity of the IND protein refers herein to a reduction in the DNA binding activity, the dimerization capacity and/or transcriptional regulating activity of the IND protein, such that the pod shatter resistance of a plant expressing the mutant IND protein is increased as compared to a plant expressing the corresponding wild type IND protein compared to the pod shatter resistance of a corresponding wild type plant.

Both endogenous and isolated amino acid sequences are provided herein. Also provided are fragments of the IND amino acid sequences and IND variant amino acid sequences defined above. A "fragment" of a IND amino acid sequence or variant thereof (as defined) may be of various lengths, such as at least 10, 12, 15, 18, 20, 50, 100, 150, 175, 180 contiguous amino acids of the IND sequence (or of the variant sequence).

Amino Acid Sequences of Functional IND Proteins

The amino acid sequences depicted in the sequence listing are wild type, functional IND proteins from *Brassica napus*. Thus, these sequences are endogenous to the *Brassica napus* plants from which they were isolated. Other *Brassica* crop species, varieties, breeding lines or wild accessions may be screened for other functional IND proteins with the same amino acid sequences or variants thereof, as described above.

In addition, it is understood that IND amino acid sequences and variants thereof (or fragments of any of these) may be identified in silico, by screening amino acid databases for essentially similar sequences. Fragments of amino acid molecules according to the invention are also provided. Fragments include amino acid sequences of the bHLH domain, or smaller fragments comprising part of the bHLH domain, such as the basic domain or the HLH domain, etc.

Amino Acid Sequences of Mutant IND Proteins

The invention provides amino acid sequences comprising one or more amino acid deletions, insertions or substitutions relative to the wild type IND amino acid sequences depicted in SEQ ID NO: 2 and 4 of the sequence listing, wherein the mutation(s) in the amino acid sequence result in a significantly reduced biological activity, i.e. a partial knockout of the biological activity, of the encoded IND protein relative to the wild type protein, as well as fragments of such mutant amino acid molecules. Such mutant amino acid sequences can be generated and/or identified using various known methods, as described above. Again, such amino acid molecules are provided both in endogenous form and in isolated form.

As described above, basically, any mutation in the wild type IND amino acid sequences which results in an IND protein comprising at least one amino acid insertion, deletion and/or substitution relative to the wild type IND protein can lead to significantly reduced or no biological activity. It is, however, understood that certain mutations in the IND protein are more likely to result in a complete abolishment of the biological activity of the IND protein, such as mutations leading to truncated proteins, whereby significant portions of the functional domains, such as the DNA binding domain ('b'), the dimerization domain ('HLH') and/or amino acids which are important in the regulation of transcription (See Table 1), are lacking, or mutations whereby certain critical amino acid residues within these domains, such as the Gln (Q), Ala (A) and Arg (R) amino acids at position 5, 9, and 13 or the basic amino acid residues (in particular Arg (R) residues) at positions 10 and 12 of the consensus bHLH domain sequence defined by Heim et al. (supra; corresponding to positions 123, 127 and 131, and 128 and 130, respectively, in SEQ ID NO: 10, see Table 1) are lacking or are substituted, preferably by non-similar or non-conservative amino acids, while other mutations of the protein are more likely to result in a significant reduction of the biological activity of the IND protein, such as mutations leading to substitutions of specific amino acids, e.g. the conserved amino acids indicated in Table 1, causing a less efficient DNA binding, a less efficient dimerization, and/or a less efficient regulation of transcription without completely abolishing the biological activity of the encoded IND protein.

Thus in one embodiment, partial knockout mutant IND proteins are provided comprising one or more deletion or insertion mutations, whereby the deletion(s) or insertion(s) result(s) in a mutant protein which has significantly reduced activity in vivo. Such mutant IND proteins are IND proteins wherein at least 1, at least 2, 3, 4, 5, 10, 20, 30, 50, 100, 100, 150, 175, 180 or more amino acids are deleted or inserted as compared to the wild type IND protein, whereby the deletion(s) or insertion(s) result(s) in a mutant protein which has significantly reduced activity in vivo.

In another embodiment, partial knockout mutant IND proteins are provided which are truncated whereby the truncation results in a mutant protein that has significantly reduced activity in vivo. Such truncated IND proteins are IND proteins which lack functional domains in the C-terminal part of the corresponding wild type IND protein and which maintain the N-terminal part of the corresponding wild type IND protein. Thus in one embodiment, a partial knockout mutant IND protein is provided comprising the N-terminal part of the corresponding wild type IND protein up to but not including the conserved Leu residue of the H2 domain (at position 56 in the consensus bHLH domain sequence as described by Heim et al., 2003, see above) is provided. The more truncated the mutant protein is in comparison to the wild type protein, the more the truncation may result in a significantly reduced activity of the IND protein. It is believed that, in order for the mutant IND protein to retain some biological activity, it should at least comprise the DNA binding (b) domain. Thus in another embodiment, a partial knockout mutant IND protein is provided comprising the N-terminal part of the corresponding wild type IND protein lacking part or all of the second H domain, and/or lacking part or all of the L domain, and/or lacking part or all of the first H domain (see Table 1).

In yet another embodiment, partial knockout mutant IND proteins are provided comprising one or more substitution mutations, whereby the substitution(s) result(s) in a mutant protein that has significantly reduced activity in vivo. In one embodiment, a partial knockout mutant IND protein is provided comprising a substitution mutation resulting in a substitution of a valine (Val) residue at position 124 of the IND protein in SEQ ID NO: 2, or a sequence essentially similar thereto, in particular by a methionine (Met) residue, such as the partial knockout mutant IND protein encoded by the ind-a1-EMS06 allele (Table 3a). In another embodiment, a partial knockout mutant IND protein is provided comprising a substitution mutation resulting in a substitution of a glycine (Gly) residue at position 146 of the IND protein in SEQ ID NO: 2, or a sequence essentially similar thereto, in particular by a serine (Ser) residue, such as the partial knockout mutant IND protein encoded by the ind-a1-EMS09 allele (Table 3a). In yet another embodiment, a partial knockout mutant IND protein is provided comprising a substitution mutation resulting in a substitution of an alanine (Ala) residue at position 159 of the IND protein in SEQ ID NO: 2, or a sequence essentially similar thereto, in particular by a valine (Val) residue, such as the partial knockout mutant IND protein encoded by the ind-a1-EMS13 allele (Table 3a). In still another embodiment, a partial knockout mutant IND protein is provided comprising a substitution mutation resulting in a substitution of a threonine (Thr) residue at position 136 of the IND protein in SEQ ID NO: 4, or a sequence essentially similar thereto, in particular by a methionine (Met) residue, such as the partial knockout mutant IND protein encoded by the ind-c1-EMS08 allele (Table 3b). In a further embodiment, a partial knockout mutant IND protein is provided comprising a substitution mutation resulting in a substitution of an alanine (Ala) residue at position 139 of the IND protein in SEQ ID NO: 4, or a sequence essentially similar thereto, in particular by a threonine (Thr) residue, such as the partial knockout mutant IND protein encoded by the ind-c1-EMS09 allele (Table 3b). In still a further embodiment, a partial knockout mutant IND protein is provided comprising a substitution mutation resulting in a substitution of an arginine (Arg) residue at position 142 of the IND protein in. SEQ ID NO: 4, or a sequence essentially similar thereto, in particular by a cysteine (Cys) residue, such as the partial knockout mutant IND protein encoded by the ind-c1-EMS04 allele (Table 3b).

In another embodiment, a partial knockout mutant IND protein is provided comprising a substitution mutation resulting in the substitution of a conserved amino acid residues as indicated above or in Table 1, such as the partial knockout mutant IND protein encoded by ind-a1-EMS13, ind-c1-EMS04 or ind-c1-EMS09 (indicated with * in Table 3).

Methods According to the Invention

In another aspect of the invention, methods are provided for generating and selecting dehiscent seed plants, and cells, parts, seeds and progeny thereof, containing at least one partial and/or at least one full knock-out ind allele. In particular, methods are provided for generating and selecting Brassica plants comprising at least two IND genes, in particular Brassica napus plants, and cells, parts, seeds and progeny thereof, containing at least one partial and/or at least one full knock-out ind allele at at least one of the at least two different IND loci in the genome, for example at at least one of the two different loci of the Brassica IND-A1 and IND-C1 gene, and to distinguish between the presence of full knockout ind alleles, partial knockout ind alleles and wild type IND alleles in a dehiscent seed plant or plant part. Thus methods are provided (such as mutagenesis and/or marker assisted selection) for generating and/or identifying partial knockout ind alleles and/or full knockout ind alleles or dehiscent seed plants or plant parts comprising such ind alleles and for combining a suitable number of partial knockout ind alleles and/or full knockout ind alleles and/or different types of partial knockout ind alleles and/or full knockout ind alleles in a single dehiscent seed plant to alter the fruit dehiscence properties of the plants, in particular to reduce seed shattering, or delay seed shattering until after harvest, while maintaining at the same time an agronomically relevant treshability of the pods.

Partial and full knockout mutant ind alleles according to the invention may be generated (for example induced by mutagenesis) and/or identified using a range of methods, which are conventional in the art, for example using PCR based methods to amplify part or all of the ind genomic or cDNA.

Following mutagenesis, plants are grown from the treated seeds, or regenerated from the treated cells using known techniques. For instance, mutagenized seeds may be planted in accordance with conventional growing procedures and following self-pollination seed is formed on the plants. Alternatively, doubled haploid plantlets may be extracted from treated microspore or pollen cells to immediately form homozygous plants, for example as described by Coventry et al. (1988, Manual for Microspore Culture Technique for *Brassica napus*. Dep. Crop Sci. Techn. Bull. OAC Publication 0489. Univ. of Guelph, Guelph, Ontario, Canada). Additional seed which is formed as a result of such self-pollination in the present or a subsequent generation may be harvested and screened for the presence of mutant IND alleles, using techniques which are conventional in the art, for example polymerase chain reaction (PCR) based techniques (amplification of the ind alleles) or hybridization based techniques, e.g. Southern blot analysis, BAC library screening, and the like, and/or direct sequencing of ind alleles. To screen for the presence of point mutations (so called Single Nucleotide Polymorphisms or SNPs) in mutant IND alleles, SNP detection methods conventional in the art can be used, for example oligoligation-based techniques, single base extension-based techniques or techniques based on differences in restriction sites, such as TILLING.

As described above, mutagenization (spontaneous as well as induced) of a specific wild-type IND allele results in the presence of one or more deleted, inserted, or substituted nucleotides (hereinafter called "mutation region") in the resulting mutant IND allele. The mutant IND allele can thus be characterized by the location and the configuration of the one or more deleted, inserted, or substituted nucleotides in the wild type IND allele. The site in the wild type IND allele where the one or more nucleotides have been inserted, deleted, or substituted, respectively, is herein also referred to as the "mutation region or sequence". A "5' or 3' flanking region or sequence" as used herein refers to a DNA region or sequence in the mutant (or the corresponding wild type) IND allele of at least 20 bp, preferably at least 50 bp, at least 750 bp, at least 1500 bp, and up to 5000 bp of DNA different from the DNA containing the one or more deleted, inserted, or substituted nucleotides, preferably DNA from the mutant (or the corresponding wild type) IND allele which is located either immediately upstream of and contiguous with (5' flanking region or sequence") or immediately downstream of and contiguous with (3' flanking region or sequence") the mutation region in the mutant IND allele (or in the corresponding wild type IND allele). A "joining region" as used herein refers to a DNA region in the mutant (or the corresponding wild type) IND allele where the mutation region and the 5' or 3' flanking region are linked to each other. A "sequence spanning the joining region between the mutation region and the 5' or 3' flanking region thus comprises a mutation sequence as well as the flanking sequence contiguous therewith.

The tools developed to identify a specific mutant IND allele or the plant or plant material comprising a specific mutant IND allele, or products which comprise plant material comprising a specific mutant IND allele are based on the specific genomic characteristics of the specific mutant IND allele as compared to the genomic characteristics of the corresponding wild type IND allele, such as, a specific restriction map of the genomic region comprising the mutation region, molecular markers or the sequence of the flanking and/or mutation regions.

Once a specific mutant IND allele has been sequenced, primers and probes can be developed which specifically recognize a sequence within the 5' flanking, 3' flanking and/or mutation regions of the mutant IND allele in the nucleic acid (DNA or RNA) of a sample by way of a molecular biological technique. For instance a PCR method can be developed to identify the mutant IND allele in biological samples (such as samples of plants, plant material or products comprising plant material). Such a PCR is based on at least two specific "primers": one recognizing a sequence within the 5' or 3' flanking region of the mutant IND allele and the other recognizing a sequence within the 3' or 5' flanking region of the mutant IND allele, respectively; or one recognizing a sequence within the 5' or 3' flanking region of the mutant IND allele and the other recognizing a sequence within the mutation region of the mutant IND allele; or one recognizing a sequence within the 5' or 3' flanking region of the mutant IND allele and the other recognizing a sequence spanning the joining region between the 3' or 5' flanking region and the mutation region of the specific mutant IND allele (as described further below), respectively.

The primers preferably have a sequence of between 15 and 35 nucleotides which under optimized PCR conditions "specifically recognize" a sequence within the 5' or 3' flanking region, a sequence within the mutation region, or a sequence spanning the joining region between the 3' or 5' flanking and mutation regions of the specific mutant IND allele, so that a specific fragment ("mutant IND specific fragment" or discriminating amplicon) is amplified from a nucleic acid sample comprising the specific mutant IND allele. This means that only the targeted mutant IND allele, and no other sequence in the plant genome, is amplified under optimized PCR conditions.

PCR Primers Suitable for the Invention May be the Following:

oligonucleotides ranging in length from 17 nt to about 200 nt, comprising a nucleotide sequence of at least 17 consecutive nucleotides, preferably 20 consecutive nucleotides selected from the 5' or 3' flanking sequence of a specific mutant IND allele or the complement thereof (i.e., for example, the sequence 5' or 3' flanking the one or more nucleotides deleted, inserted or substituted in the mutant IND alleles of the invention, such as the sequence 5' or 3' flanking the non-sense, missense or frameshift mutations described above or the sequence 5' or 3' flanking the STOP codon mutations indicated in the above Tables or the substitution mutations indicated above or the complement thereof) (primers recognizing 5' flanking sequences); or oligonucleotides ranging in length from 17 nt to about 200 nt, comprising a nucleotide sequence of at least 17 consecutive nucleotides, preferably 20 nucleotides selected from the sequence of the mutation region of a specific mutant IND allele or the complement thereof (i.e., for example, the sequence of nucleotides inserted or substituted in the IND genes of the invention or the complement thereof) (primers recognizing mutation sequences).

The primers may of course be longer than the mentioned 17 consecutive nucleotides, and may e.g. be 18, 19, 20, 21, 30, 35, 50, 75, 100, 150, 200 nt long or even longer. The primers may entirely consist of nucleotide sequence selected from the mentioned nucleotide sequences of flanking and mutation sequences. However, the nucleotide sequence of the primers at their 5' end (i.e. outside of the 3'-located 17 consecutive nucleotides) is less critical. Thus, the 5' sequence of the primers may consist of a nucleotide sequence selected from the flanking or mutation sequences, as appropriate, but may contain several (e.g. 1, 2, 5, 10) mismatches. The 5' sequence of the primers may even entirely consist of a nucleotide sequence unrelated to the flanking or mutation sequences, such as e.g. a nucleotide sequence representing restriction enzyme recognition sites. Such unrelated sequences or flanking DNA sequences with mismatches should preferably be not longer than 100, more preferably not longer than 50 or even 25 nucleotides.

Moreover, suitable primers may comprise or consist of a nucleotide sequence spanning the joining region between flanking and mutation sequences (i.e., for example, the joining region between a sequence 5' or 3' flanking one or more nucleotides deleted, inserted or substituted in the mutant IND alleles of the invention and the sequence of the one or more nucleotides inserted or substituted or the sequence 3' or 5', respectively, flanking the one or more nucleotides deleted, such as the joining region between a sequence 5' or 3' flanking non-sense, missense or frameshift mutations in the IND genes of the invention described above and the sequence of the non-sense, missense or frameshift mutations, or the joining region between a sequence 5' or 3' flanking a potential STOP codon mutation as indicated in the above Tables or the substitution mutations indicated above and the sequence of the potential STOP codon mutation or the substitution mutations, respectively), provided the nucleotide sequence is not derived exclusively from either the mutation region or flanking regions.

It will also be immediately clear to the skilled artisan that properly selected PCR primer pairs should also not comprise sequences complementary to each other.

For the purpose of the invention, the "complement of a nucleotide sequence represented in SEQ ID No: X" is the nucleotide sequence which can be derived from the represented nucleotide sequence by replacing the nucleotides through their complementary nucleotide according to Chargaff's rules (A↔T; G↔C) and reading the sequence in the 5' to 3' direction, i.e. in opposite direction of the represented nucleotide sequence.

Examples of primers suitable to identify specific mutant IND alleles are described in the Examples.

As used herein, "the nucleotide sequence of SEQ ID No. Z from position X to position Y" indicates the nucleotide sequence including both nucleotide endpoints.

Preferably, the amplified fragment has a length of between 50 and 1000 nucleotides, such as a length between 50 and 500 nucleotides, or a length between 100 and 350 nucleotides. The specific primers may have a sequence which is between 80 and 100% identical to a sequence within the 5' or 3' flanking region, to a sequence within the mutation region, or to a sequence spanning the joining region between the 3' or 5' flanking and mutation regions of the specific mutant IND allele, provided the mismatches still allow specific identification of the specific mutant IND allele with these primers under optimized PCR conditions. The range of allowable mismatches however, can easily be determined experimentally and are known to a person skilled in the art.

Detection and/or identification of a "mutant IND specific fragment" can occur in various ways, e.g., via size estimation after gel or capillary electrophoresis or via fluorescence-based detection methods. The mutant IND specific fragments may also be directly sequenced. Other sequence specific methods for detection of amplified DNA fragments are also known in the art.

Standard PCR protocols are described in the art, such as in 'PCR Applications Manual" (Roche Molecular Biochemicals, 2nd Edition, 1999) and other references. The optimal conditions for the PCR, including the sequence of the specific primers, is specified in a "PCR identification protocol" for each specific mutant IND allele. It is however understood that a number of parameters in the PCR identification protocol may need to be adjusted to specific laboratory conditions, and may be modified slightly to obtain similar results. For instance, use of a different method for preparation of DNA may require adjustment of, for instance, the amount of primers, polymerase, $MgCl_2$ concentration or annealing conditions used. Similarly, the selection of other primers may dictate other optimal conditions for the PCR identification protocol. These adjustments will however be apparent to a person skilled in the art, and are furthermore detailed in current PCR application manuals such as the one cited above.

Examples of PCR identification protocols to identify specific mutant IND alleles are described in the Examples.

Alternatively, specific primers can be used to amplify a mutant IND specific fragment that can be used as a "specific probe" for identifying a specific mutant IND allele in biological samples. Contacting nucleic acid of a biological sample, with the probe, under conditions that allow hybridization of the probe with its corresponding fragment in the nucleic acid, results in the formation of a nucleic acid/probe hybrid. The formation of this hybrid can be detected (e.g. labeling of the nucleic acid or probe), whereby the formation of this hybrid indicates the presence of the specific mutant IND allele. Such identification methods based on hybridization with a specific probe (either on a solid phase carrier or in solution) have been described in the art. The specific probe is preferably a sequence that, under optimized conditions, hybridizes specifically to a region within the 5' or 3' flanking region and/or within the mutation region of the specific mutant IND allele (hereinafter referred to as "mutant IND specific region"). Preferably, the specific probe comprises a sequence of between 10 and 1000 bp, 50 and 600 bp, between 100 to 500 bp, between 150 to 350 bp, which is at least 80%, preferably between 80 and 85%, more preferably between 85 and 90%, especially preferably between 90 and 95%, most preferably between 95% and 100% identical (or complementary) to the nucleotide sequence of a specific region. Preferably, the specific probe will comprise a sequence of about 13 to about 100 contiguous nucleotides identical (or complementary) to a specific region of the specific mutant IND allele.

Specific probes suitable for the invention may be the following:

oligonucleotides ranging in length from 13 nt to about 1000 nt, comprising a nucleotide sequence of at least 13 consecutive nucleotides selected from the 5' or 3' flanking sequence of a specific mutant IND allele or the complement thereof (i.e., for example, the sequence 5' or 3' flanking the one or more nucleotides deleted, inserted or substituted in the mutant IND alleles of the invention, such as the sequence 5' or 3' flanking the non-sense, mis-sense or frameshift mutations described above or the sequence 5' or 3' flanking the potential STOP codon mutations indicated in the above Tables or the substitution mutations indicated above), or a sequence having at least 80% sequence identity therewith (probes recognizing 5' flanking sequences); or oligonucleotides ranging in length from 13 nt to about 1000 nt, comprising a nucleotide sequence of at least 13 consecutive nucleotides selected from the mutation sequence of a specific mutant IND allele or the complement thereof (i.e., for example, the sequence of nucleotides inserted or substituted in the IND genes of the invention, or the complement thereof), or a sequence having at least 80% sequence identity therewith (probes recognizing mutation sequences).

The probes may entirely consist of nucleotide sequence selected from the mentioned nucleotide sequences of flanking and mutation sequences. However, the nucleotide sequence of the probes at their 5' or 3' ends is less critical. Thus, the 5' or 3' sequences of the probes may consist of a nucleotide sequence selected from the flanking or mutation sequences, as appropriate, but may consist of a nucleotide sequence unrelated to the flanking or mutation sequences. Such unrelated sequences should preferably be not longer than 50, more preferably not longer than 25 or even not longer than 20 or 15 nucleotides.

Moreover, suitable probes may comprise or consist of a nucleotide sequence spanning the joining region between flanking and mutation sequences (i.e., for example, the joining region between a sequence 5' or 3' flanking one or more nucleotides deleted, inserted or substituted in the mutant IND alleles of the invention and the sequence of the one or more nucleotides inserted or substituted or the sequence 3' or 5', respectively, flanking the one or more nucleotides deleted, such as the joining region between a sequence 5' or 3' flanking non-sense, mis-sense or frameshift mutations in the IND genes of the invention described above and the sequence of the non-sense, mis-sense or frameshift mutations, or the joining region between a sequence 5' or 3' flanking a potential STOP codon mutation as indicated in the above Tables or the substitution mutations indicated above and the sequence of the potential STOP codon or substitution mutation, respectively), provided the mentioned nucleotide sequence is not derived exclusively from either the mutation region or flanking regions.

Examples of specific probes suitable to identify specific mutant IND alleles are described in the Examples.

Detection and/or identification of a "mutant IND specific region" hybridizing to a specific probe can occur in various ways, e.g., via size estimation after gel electrophoresis or via fluorescence-based detection methods. Other sequence specific methods for detection of a "mutant IND specific region" hybridizing to a specific probe are also known in the art.

Alternatively, plants or plant parts comprising one or more mutant ind alleles can be generated and identified using other methods, such as the "Delete-a-gene™" method which uses PCR to screen for deletion mutants generated by fast neutron mutagenesis (reviewed by Li and Zhang, 2002, Funct Integr Genomics 2:254-258), by the TILLING (Targeting Induced Local Lesions IN Genomes) method which identifies EMS-induced point mutations using denaturing high-performance liquid chromatography (DHPLC) to detect base pair changes by heteroduplex analysis (McCallum et al., 2000, Nat Biotech 18:455, and McCallum et al. 2000, Plant Physiol. 123, 439-442), etc. As mentioned, TILLING uses high-throughput screening for mutations (e.g. using Cel 1 cleavage of mutant-wildtype DNA heteroduplexes and detection using a sequencing gel system). Thus, the use of TILLING to identify plants or plant parts comprising one or more mutant ind alleles and methods for generating and identifying such plants, plant organs, tissues and seeds is encompassed herein. Thus in one embodiment, the method according to the invention comprises the steps of mutagenizing plant seeds (e.g. EMS mutagenesis), pooling of plant individuals or DNA, PCR amplification of a region of interest, heteroduplex formation and high-throughput detection, identification of the mutant plant, sequencing of the mutant PCR product. It is understood that other mutagenesis and selection methods may equally be used to generate such mutant plants.

Instead of inducing mutations in IND alleles, natural (spontaneous) mutant alleles may be identified by methods known in the art. For example, ECOTILLING may be used (Henikoff et al. 2004, Plant Physiology 135(2):630-6) to screen a plurality of plants or plant parts for the presence of natural mutant ind alleles. As for the mutagenesis techniques above, preferably *Brassica* species are screened which comprise an A and/or a C genome, so that the identified ind allele can subsequently be introduced into other *Brassica* species, such as *Brassica napus*, by crossing (inter- or intraspecific crosses) and selection. In ECOTILLING natural polymorphisms in breeding lines or related species are screened for by the TILLING methodology described above, in which individual or pools of plants are used for PCR amplification of the ind target, heteroduplex formation and high-throughput analysis. This can be followed by selecting individual plants having a required mutation that can be used subsequently in a breeding program to incorporate the desired mutant allele.

The identified mutant alleles can then be sequenced and the sequence can be compared to the wild type allele to identify the mutation(s). Optionally functionality can be tested as indicated above. Using this approach a plurality of mutant ind alleles (and *Brassica* plants comprising one or more of these) can be identified. The desired mutant alleles can then be combined with the desired wild type alleles by crossing and selection methods as described further below. Finally a single plant comprising the desired number of mutant ind and the desired number of wild type IND alleles is generated.

Oligonucleotides suitable as PCR primers or specific probes for detection of a specific mutant IND allele can also be used to develop methods to determine the zygosity status of the specific mutant IND allele.

To determine the zygosity status of a specific mutant IND allele, a PCR-based assay can be developed to determine the presence of a mutant and/or corresponding wild type IND specific allele:

To determine the zygosity status of a specific mutant IND allele, two primers specifically recognizing the wild-type IND allele can be designed in such a way that they are directed towards each other and have the mutation region located in between the primers. These primers may be primers specifically recognizing the 5' and 3' flanking sequences, respectively. This set of primers allows simultaneous diagnostic PCR amplification of the mutant, as well as of the corresponding wild type IND allele.

Alternatively, to determine the zygosity status of a specific mutant IND allele, two primers specifically recognizing the wild-type IND allele can be designed in such a way that they are directed towards each other and that one of them specifically recognizes the mutation region. These primers may be primers specifically recognizing the sequence of the 5' or 3' flanking region and the mutation region of the wild type IND allele, respectively. This set of primers, together with a third primer which specifically recognizes the sequence of the mutation region in the mutant IND allele, allow simultaneous diagnostic PCR amplification of the mutant IND gene, as well as of the wild type IND gene.

Alternatively, to determine the zygosity status of a specific mutant IND allele, two primers specifically recognizing the wild-type IND allele can be designed in such a way that they are directed towards each other and that one of them specifically recognizes the joining region between the 5' or 3' flanking region and the mutation region. These primers may be primers specifically recognizing the 5' or 3' flanking sequence and the joining region between the mutation region and the 3' or 5' flanking region of the wild type IND allele, respectively. This set of primers, together with a third primer which specifically recognizes the joining region between the mutation region and the 3' or 5' flanking region of the mutant IND allele, respectively, allow simultaneous diagnostic PCR amplification of the mutant IND gene, as well as of the wild type IND gene.

Alternatively, the zygosity status of a specific mutant IND allele can be determined by using alternative primer sets that specifically recognize mutant and wild type IND alleles.

If the plant is homozygous for the mutant IND gene or the corresponding wild type IND gene, the diagnostic PCR assays described above will give rise to a single PCR product typical, preferably typical in length, for either the mutant or wild type IND allele. If the plant is heterozygous for the mutant IND allele, two specific PCR products will appear, reflecting both the amplification of the mutant and the wild type IND allele.

Identification of the wild type and mutant IND specific PCR products can occur e.g. by size estimation after gel or capillary electrophoresis (e.g. for mutant IND alleles comprising a number of inserted or deleted nucleotides which results in a size difference between the fragments amplified from the wild type and the mutant IND allele, such that said fragments can be visibly separated on a gel); by evaluating the presence or absence of the two different fragments after gel or capillary electrophoresis, whereby the diagnostic PCR amplification of the mutant IND allele can, optionally, be performed separately from the diagnostic PCR amplification of the wild type IND allele; by direct sequencing of the amplified fragments; or by fluorescence-based detection methods.

Examples of primers suitable to determine the zygosity of specific mutant IND alleles are described in the Examples.

Alternatively, to determine the zygosity status of a specific mutant IND allele, a hybridization-based assay can be developed to determine the presence of a mutant and/or corresponding wild type IND specific allele:

To determine the zygosity status of a specific mutant IND allele, two specific probes recognizing the wild-type IND allele can be designed in such a way that each probe specifically recognizes a sequence within the IND wild type allele and that the mutation region is located in between the sequences recognized by the probes. These probes may be probes specifically recognizing the 5' and 3' flanking sequences, respectively. The use of one or, preferably, both of these probes allows simultaneous diagnostic hybridization of the mutant, as well as of the corresponding wild type IND allele.

Alternatively, to determine the zygosity status of a specific mutant IND allele, two specific probes recognizing the wild-type IND allele can be designed in such a way that one of them specifically recognizes a sequence within the IND wild type allele upstream or downstream of the mutation region, preferably upstream of the mutation region, and that one of them specifically recognizes the mutation region. These probes may be probes specifically recognizing the sequence of the 5' or 3' flanking region, preferably the 5' flanking region, and the mutation region of the wild type IND allele, respectively. The use of one or, preferably, both of these probes, optionally, together with a third probe which specifically recognizes the sequence of the mutation region in the mutant IND allele, allow diagnostic hybridization of the mutant and of the wild type IND gene.

Alternatively, to determine the zygosity status of a specific mutant IND allele, a specific probe recognizing the wild-type IND allele can be designed in such a way that the probe specifically recognizes the joining region between the 5' or 3' flanking region, preferably the 5' flanking region, and the mutation region of the wild type IND allele. This probe, optionally, together with a second probe that specifically recognizes the joining region between the 5' or 3' flanking region, preferably the 5' flanking region, and the mutation region of the mutant IND allele, allows diagnostic hybridization of the mutant and of the wild type IND gene.

Alternatively, the zygosity status of a specific mutant IND allele can be determined by using alternative sets of probes that specifically recognize mutant and wild type IND alleles.

If the plant is homozygous for the mutant IND gene or the corresponding wild type IND gene, the diagnostic hybridization assays described above will give rise to a single specific hybridization product, such as one or more hybridizing DNA (restriction) fragments, typical, preferably typical in length, for either the mutant or wild type IND allele. If the plant is heterozygous for the mutant IND allele, two specific hybridization products will appear, reflecting both the hybridization of the mutant and the wild type IND allele.

Identification of the wild type and mutant IND specific hybridization products can occur e.g. by size estimation after gel or capillary electrophoresis (e.g. for mutant IND alleles comprising a number of inserted or deleted nucleotides which results in a size difference between the hybridizing DNA (restriction) fragments from the wild type and the mutant IND allele, such that said fragments can be visibly separated on a gel); by evaluating the presence or absence of the two different specific hybridization products after gel or capillary electrophoresis, whereby the diagnostic hybridization of the mutant IND allele can, optionally, be performed separately from the diagnostic hybridization of the wild type IND allele; by direct sequencing of the hybridizing DNA (restriction) fragments; or by fluorescence-based detection methods.

Examples of probes suitable to determine the zygosity of specific mutant IND alleles are described in the Examples.

Furthermore, detection methods specific for a specific mutant IND allele that differ from PCR- or hybridization-based amplification methods can also be developed using the specific mutant IND allele specific sequence information provided herein. Such alternative detection methods include linear signal amplification detection methods based on invasive cleavage of particular nucleic acid structures, also known as Invader™ technology, (as described e.g. in U.S. Pat. No. 5,985,557 "Invasive Cleavage of Nucleic Acids", U.S. Pat. No. 6,001,567 "Detection of Nucleic Acid sequences by Invader Directed Cleavage, incorporated herein by reference), RT-PCR-based detection methods, such as Taqman, or other detection methods, such as SNPlex, Single Base Extension (SBE), and the like. Briefly, in the Invader™ technology, the target mutation sequence may e.g. be hybridized with a labeled first nucleic acid oligonucleotide comprising the nucleotide sequence of the mutation sequence or a sequence spanning the joining region between the 5' flanking region and the mutation region and with a second nucleic acid oligonucleotide comprising the 3' flanking sequence immediately downstream and adjacent to the mutation sequence, wherein the first and second oligonucleotide overlap by at least one nucleotide. The duplex or triplex structure that is produced by this hybridization allows selective probe cleavage with an enzyme (Cleavase®) leaving the target sequence intact. The cleaved labeled probe is subsequently detected, potentially via an intermediate step resulting in further signal amplification.

A "kit", as used herein, refers to a set of reagents for the purpose of performing the method of the invention, more particularly, the identification of a specific mutant IND allele in biological samples or the determination of the zygosity status of plant material comprising a specific mutant IND allele. More particularly, a preferred embodiment of the kit of the invention comprises at least two specific primers, as described above, for identification of a specific mutant IND allele, or at least two or three specific primers for the determination of the zygosity status. Optionally, the kit can further comprise any other reagent described herein in the PCR identification protocol. Alternatively, according to another embodiment of this invention, the kit can comprise at least one specific probe, which specifically hybridizes with nucleic acid of biological samples to identify the presence of a specific mutant IND allele therein, as described above, for identification of a specific mutant IND allele, or at least two or three specific probes for the determination of the zygosity status. Optionally, the kit can further comprise any other reagent (such as but not limited to hybridizing buffer, label) for identification of a specific mutant IND allele in biological samples, using the specific probe.

The kit of the invention can be used, and its components can be specifically adjusted, for purposes of quality control (e.g., purity of seed lots), detection of the presence or absence of a specific mutant IND allele in plant material or material comprising or derived from plant material, such as but not limited to food or feed products.

The term "primer" as used herein encompasses any nucleic acid that is capable of priming the synthesis of a nascent nucleic acid in a template-dependent process, such as PCR. Typically, primers are oligonucleotides from 10 to 30 nucleotides, but longer sequences can be employed. Primers may be provided in double-stranded form, though the single-stranded form is preferred. Probes can be used as primers, but are designed to bind to the target DNA or RNA and need not be used in an amplification process.

The term "recognizing" as used herein when referring to specific primers, refers to the fact that the specific primers specifically hybridize to a nucleic acid sequence in a specific mutant IND allele under the conditions set forth in the method (such as the conditions of the PCR identification protocol), whereby the specificity is determined by the presence of positive and negative controls.

The term "hybridizing", as used herein when referring to specific probes, refers to the fact that the probe binds to a specific region in the nucleic acid sequence of a specific mutant IND allele under standard stringency conditions. Standard stringency conditions as used herein refers to the conditions for hybridization described herein or to the conventional hybridizing conditions as described by Sambrook et al., 1989 (Molecular Cloning: A Laboratory Manual, Second Edition, Cold Spring Harbour Laboratory Press, NY) which for instance can comprise the following steps: 1) immobilizing plant genomic DNA fragments or BAC library DNA on a filter, 2) prehybridizing the filter for 1 to 2 hours at 65° C. in 6×SSC, 5×Denhardt's reagent, 0.5% SDS and 20 µg/ml denatured carrier DNA, 3) adding the hybridization probe which has been labeled, 4) incubating for 16 to 24 hours, 5) washing the filter once for 30 min. at 68° C. in 6×SSC, 0.1% SDS, 6) washing the filter three times (two times for 30 min. in 30 ml and once for 10 min in 500 ml) at 68° C. in 2×SSC, 0.1% SDS, and 7) exposing the filter for 4 to 48 hours to X-ray film at −70° C.

As used in herein, a "biological sample" is a sample of a plant, plant material or product comprising plant material. The term "plant" is intended to encompass plant tissues, at any stage of maturity, as well as any cells, tissues, or organs taken from or derived from any such plant, including without limitation, any seeds, leaves, stems, flowers, roots, single cells, gametes, cell cultures, tissue cultures or protoplasts. "Plant material", as used herein refers to material that is obtained or derived from a plant. Products comprising plant material relate to food, feed or other products that are produced using plant material or can be contaminated by plant material. It is understood that, in the context of the present invention, such biological samples are tested for the presence of nucleic acids specific for a specific mutant IND allele, implying the presence of nucleic acids in the samples. Thus the methods referred to herein for identifying a specific mutant IND allele in biological samples, relate to the identification in biological samples of nucleic acids that comprise the specific mutant IND allele.

The present invention also relates to the combination of specific IND alleles in one plant, to the transfer of one or more specific mutant IND allele(s) from one plant to another plant, to the plants comprising one or more specific mutant IND allele(s), the progeny obtained from these plants and to plant cells, plant parts, and plant seeds derived from these plants.

In one embodiment, a method is provided for combining a suitable number of partial knockout ind alleles and/or full knockout ind alleles and/or different types of partial knockout ind alleles and/or full knockout ind alleles in a single dehiscent seed plant to alter the fruit dehiscence properties of the plant, in particular to reduce seed shattering, or delay seed shattering until after harvest, while maintaining at the same time an agronomically relevant treshability of the pods.

In one aspect, a method is provided for altering the fruit dehiscence properties, in particular for reducing seed shattering, or delaying seed shattering until after harvest, while maintaining at the same time an agronomically relevant treshability of the pods, of a *Brassica* plant comprising at least two IND genes, comprising the steps of:
  generating and/or selecting a *Brassica* plant comprising at least two IND genes, wherein at least two alleles of the at least two IND genes are partial knockout ind alleles, as described above,
  selecting a plant with altered fruit dehiscence properties, in particular a plant wherein seed shattering is reduced or delayed until after harvest, while the pods maintain at the same time an agronomically relevant treshability.

In one embodiment of this aspect, the *Brassica* plant comprising at least two IND genes is a *Brassica napus* plant comprising an IND-A1 and an IND-C1 gene. In a particular aspect of this embodiment, the at least two partial knockout ind alleles are partial knockout ind alleles of the IND-C1 gene.

In another aspect, the method further comprises the step of generating and/or selecting a *Brassica* plant comprising at least two IND genes, wherein at least two further alleles of the at least two IND genes are full knockout ind alleles, as described above. In one embodiment, the *Brassica* plant comprising at least two IND genes is a *Brassica napus* plant comprising an IND-A1 and an IND-C1 gene. In a particular aspect of this embodiment, the at least two partial knockout ind alleles are partial knockout ind alleles of the IND-A1 gene and the at least two full knockout ind alleles are full knockout ind alleles of the IND-C1 gene.

In another embodiment of the invention, a method for making a hybrid Brassica crop plant or seed comprising at least two IND genes, in particular a hybrid Brassica napus plant or seed, wherein the fruit dehiscence properties of the plant or of the plant grown from the seed are altered, in particular wherein seed shattering is reduced or delayed until after harvest, while the pods maintain at the same time an agronomically relevant treshability, comprising the steps of:
generating and/or identifying a first plant comprising a first partial knockout ind allele in homozygous state and a second plant comprising a second partial knockout ind allele in homozygous state, as described above,
crossing the first and the second plant and collecting F1 hybrid seeds from the cross comprising two partial knockout ind alleles of the at least two IND genes.

In a further embodiment of the invention, the first plant additionally comprises a first full knockout ind allele in homozygous state and the second plant additionally comprises a second full knockout ind allele in homozygous state, as described above, and F1 hybrid seeds comprising two partial knockout ind alleles and two full knockout ind alleles of the at least two IND genes are collected.

The possibility of using parent plants comprising a partial and/or a full knockout ind allele in homozygous state to produce hybrid seed from which plants can be grown that show reduced or delayed seed shattering, while maintaining at the same time an agronomically relevant treshability of the pods, provides an advantages over the use of one parent plant comprising two full knockout ind alleles in homozygous state and one parent plant comprising one full knockout ind allele state as described in WO09/068313 (claiming priority of European patent application EP 07023052), as both parent plants produce pods showing an agronomically relevant treshability, while the pods of the parent plant comprising two full knockout ind alleles in homozygous state produces tube-like pods from which it is difficult to harvest the seeds.

In one aspect of the invention, the first and the second partial knockout ind alleles are the same, such that the F1 hybrid seeds are homozygous for a partial knockout ind allele. In another aspect of the invention, the first and the second full knockout ind alleles are the same, such that the F1 hybrid seeds are homozygous for a full knockout ind allele.

Full knockout ind alleles (i.e., IND alleles the functional expression of which is completely abolished), such as those described in WO09/068313 (claiming priority of European patent application EP 07023052), and/or partial knockout ind alleles (i.e., IND alleles the functional expression of which is partially abolished) according to the invention can be combined according to standard breeding techniques.

Partial and/or full knockout ind alleles can, for example, be combined in a single dehiscent seed plant by
(a) generating and/or identifying two or more plants each comprising one or more selected partial and/or full knockout ind alleles, as described above for the partial and in WO09/068313 (claiming priority of European patent application EP 07023052), for the full knockout ind alleles,
(b) crossing a first plant comprising one or more selected partial and/or full knockout ind alleles with a second plant comprising one or more other selected partial and/or full knockout ind alleles, collecting F1 seeds from the cross, and, optionally, identifying an F1 plant comprising one or more selected partial and/or full knockout ind alleles from the first plant with one or more selected partial and/or full knockout indalleles from the second plant, as described above,
(c) optionally, repeating step (b) until an F1 plant comprising all selected partial and/or full knockout ind alleles is obtained,
(d) optionally,
identifying an F1 plant, which is homozygous or heterozygous for a selected partial and/or full knockout ind allele by determining the zygosity status of the mutant IND alleles, as described above for the partial and in WO09/068313 (claiming priority of European patent application EP 07023052), for the full knockout ind alleles, or
generating plants which are homozygous for one or more of the selected partial and/or full knockout ind alleles by performing one of the following steps:
extracting doubled haploid plants from treated microspore or pollen cells of F1 plants comprising the one or more selected partial and/or full knockout ind alleles, as described above,
selfing the F1 plants comprising the one or more selected partial and/or full knockout ind allele(s) for one or more generations (y), collecting F1 Sy seeds from the selfings, and identifying F1 Sy plants, which are homozygous for the one or more partial and/or full knockout ind allele, as described above.

Partial and/or full knockout ind alleles can, for example, be transferred from one dehiscent seed plant to another by
(a) generating and/or identifying a first plant comprising one or more selected partial and/or full knockout ind alleles, as described above, or generating the first plant by combining the one or more selected partial and/or full knockout ind alleles in one plant, as described above (wherein the first plant is homozygous or heterozygous for the one or more partial and/or full knockout ind alleles)
(b) crossing the first plant comprising the one or more partial and/or full knockout ind alleles with a second plant not comprising the one or more partial and/or full knockout ind alleles, collecting F1 seeds from the cross (wherein the seeds are heterozygous for a partial and/or full knockout ind allele if the first plant was homozygous for that partial and/or full knockout ind allele, and wherein half of the seeds are heterozygous and half of the seeds are azygous for, i.e. do not comprise, a partial and/or full knockout ind allele if the first plant was heterozygous for that partial and/or full knockout ind allele), and, optionally, identifying F1 plants comprising one or more selected partial and/or full knockout ind alleles, as described above,
(c) backcrossing F1 plants comprising one or more selected partial and/or full knockout ind alleles with the second plant not comprising the one or more selected partial and/or full knockout ind alleles for one or more generations (x), collecting BCx seeds from the crosses, and identifying in every generation BCx plants comprising the one or more selected partial and/or full knockout ind alleles, as described above,
(d) optionally, generating BCx plants which are homozygous for the one or more selected partial and/or full knockout ind alleles by performing one of the following steps:
extracting doubled haploid plants from treated microspore or pollen cells of BCx plants comprising the one or more desired partial and/or full knockout ind allele(s), as described above, selfing the BCx plants comprising the one or more desired partial and/or full knockout ind allele(s) for one or more generations (y), collecting BCx Sy seeds from the selfings, and identifying BCx Sy plants, which are homozygous for the one or more desired partial and/or full knockout ind allele, as described above.

The first and the second dehiscent seed plant can be Brassicaceae plants, particularly *Brassica* plants, especially *Brassica napus* plants or plants from another *Brassica* crop species. Alternatively, the first plant can be a Brassicaceae plant, particularly a *Brassica* plant, especially a *Brassica napus* plant or a plant from another *Brassica* crop species, and the second plant can be a plant from a Brassicaceae breeding line, particularly from a *Brassica* breeding line, especially from a *Brassica napus* breeding line or from a breeding line from another *Brassica* crop species. "Breeding line", as used herein, is a preferably homozygous plant line distinguishable from other plant lines by a preferred genotype and/or phenotype that is used to produce hybrid offspring.

Sequences

SEQ ID NO: 1: Coding DNA of the IND-A1 gene encoding a wild-type IND-A1 protein from *Brassica napus*.
SEQ ID NO: 2: wild type IND-A1 protein encoded by SEQ ID NO: 1.
SEQ ID NO: 3: Coding DNA of the IND-C1 gene encoding a wild-type IND-C1 protein from *Brassica napus*.
SEQ ID NO: 4: wild type IND-C1 protein encoded by SEQ ID NO: 3.
SEQ ID NO: 5: Genomic DNA of the IND-A1 gene encoding a wild-type IND-A1 protein from *Brassica napus*.
SEQ ID NO: 6: wild type IND-A1 protein encoded by SEQ ID NO: 5.
SEQ ID NO: 7: Genomic DNA of the IND-C1 gene encoding a wild-type IND-C1 protein from *Brassica napus*.
SEQ ID NO: 8: wild type IND-C1 protein encoded by SEQ ID NO: 7.
SEQ ID NO: 9: Coding DNA of the *Arabidopsis* IND1 gene.
SEQ ID NO: 10: *Arabidopsis* IND1 protein encoded by SEQ ID NO: 9.
SEQ ID NO: 11: Oligonucleotide for detection of IND-A1-EMS06 and -WT
SEQ ID NO: 12: Oligonucleotide for detection of IND-A1-EMS06
SEQ ID NO: 13: Oligonucleotide for detection of IND-A1-WT
SEQ ID NO: 14: Oligonucleotide for detection of IND-A1-EMS09 and -WT
SEQ ID NO: 15: Oligonucleotide for detection of IND-A1-EMS09
SEQ ID NO: 16: Oligonucleotide for detection of IND-A1-WT
SEQ ID NO: 17: Oligonucleotide for detection of IND-A1-EMS13 and -WT
SEQ ID NO: 18: Oligonucleotide for detection of IND-A1-EMS13
SEQ ID NO: 19: Oligonucleotide for detection of IND-A1-WT
SEQ ID NO: 20: Oligonucleotide for detection of IND-C1-EMS04 and -WT
SEQ ID NO: 21: Oligonucleotide for detection of IND-C1-EMS04
SEQ ID NO: 22: Oligonucleotide for detection of IND-C1-WT
SEQ ID NO: 23: Oligonucleotide for detection of IND-C1-EMS08 and -WT
SEQ ID NO: 24: Oligonucleotide for detection of IND-C1-EMS08
SEQ ID NO: 25: Oligonucleotide for detection of IND-C1-WT
SEQ ID NO: 26: Oligonucleotide for detection of IND-C1-EMS09 and -WT
SEQ ID NO: 27: Oligonucleotide for detection of IND-C1-EMS09
SEQ ID NO: 28: Oligonucleotide for detection of IND-C1-WT Unless stated otherwise in the Examples, all recombinant DNA techniques are carried out according to standard molecular biological techniques as described in Sambrook and Russell (2001) *Molecular Cloning: A Laboratory Manual*, Third Edition, Cold Spring Harbor Laboratory Press, NY, in Volumes 1 and 2 of Ausubel et al. (1994) *Current Protocols in Molecular Biology, Current Protocols*, USA and in Volumes I and II of Brown (1998) *Molecular Biology LabFax*, Second Edition, Academic Press (UK). Standard materials and methods for plant molecular work are described in *Plant Molecular Biology Labfax* (1993) by R. D. D. Croy, jointly published by BIOS Scientific Publications Ltd (UK) and Blackwell Scientific Publications, UK. Standard materials and methods for polymerase chain reactions can be found in Dieffenbach and Dveksler (1995) *PCR Primer: A Laboratory Manual*, Cold Spring Harbor Laboratory Press, and in McPherson at al. (2000) *PCR-Basics: From Background to Bench*, First Edition, Springer Verlag, Germany. Standard procedures for AFLP analysis are described in Vos et al. (1995, NAR 23:4407-4414) and in published EP patent application EP 534858.

EXAMPLES

Example 1

Generation and Isolation of Partial Knockout Mutant IND Alleles (Ind)

Mutations in the IND genes depicted in SEQ ID NO: 1 or 3 and 5 or 7 of the sequence listing were generated and identified as follows:

30,000 seeds from an elite spring oilseed rape breeding line (M0 seeds) were preimbibed for two hours on wet filter paper in deionized or distilled water. Half of the seeds were exposed to 0.8% EMS and half to 1% EMS (Sigma: M0880) and incubated for 4 hours.

The mutagenized seeds (M1 seeds) were rinsed 3 times and dried in a fume hood overnight. 30,000 M1 plants were grown in soil and selfed to generate M2 seeds. M2 seeds were harvested for each individual M1 plant.

Two times 4800 M2 plants, derived from different M1 plants, were grown and DNA samples were prepared from leaf samples of each individual M2 plant according to the CTAB method (Doyle and Doyle, 1987, Phytochemistry Bulletin 19:11-15).

The DNA samples were screened for the presence of point mutations in the IND genes causing the substitution of amino acids in the IND proteins, particularly in the bHLH domain of the IND proteins, by direct sequencing by standard sequencing techniques (Agowa) and analyzing the sequences for the presence of the point mutations using the NovoSNP software (VIB Antwerp).

The partial knockout mutant IND alleles (ind) indicated in Table 3a and b above were thus identified.

In conclusion, the above examples show how partial knockout mutant IND alleles can be generated and isolated. Also, plant material comprising such mutant alleles can be used to combine selected mutant IND alleles in a plant, as described in the following examples.

Example 2

Identification of a *Brassica* Plant Comprising a Partial Knockout Mutant *Brassica* IND Allele

*Brassica* plants comprising the mutations in the IND genes identified in Example 1 were identified as follows:
For each mutant IND gene identified in the DNA sample of an M2 plant, at least 50 M2 plants derived from the same M1 plant as the M2 plant comprising the IND mutation were grown and DNA samples were prepared from leaf samples of each individual M2 plant.
The DNA samples were screened for the presence of the identified point IND mutation as described above in Example 1.
Heterozygous and homozygous (as determined based on the electropherograms) M2 plants comprising the same mutation were selfed and M3 seeds were harvested.

Example 3

Analysis of the Fruit Dehiscence Properties of *Brassica* Plants Comprising a Partial and/or Full Knockout Mutant *Brassica* IND Gene To determine the correlation between the presence of partial and/or full knockout mutant IND genes in *Brassica* plants and the fruit dehiscence properties of the *Brassica* plants, the fruit dehiscence properties of *Brassica napus* plants comprising a partial knockout mutant IND gene in homozygous state alone or both a partial and a full knockout mutant IND gene in homozygous state were analyzed in the glass house and in the field and compared with the fruit dehiscence properties of *Brassica napus* plants comprising 2 to 4 full knockout ind alleles as described in WO09/068313 (claiming priority of European patent application EP 07023052) as follows:
To examine whether and how the fruit valve margins and the dehiscence properties of seed pods were affected by the presence of partial and/or full knockout mutant IND genes, ind fruit was compared to wild-type fruit using the following macroscopic tests:
(a) Inspection of the seed pods and plants in general with naked eye to determine differences in the phenotype of the pods and plants caused by the presence of different partial and/or full knockout mutant IND genes. Determination of the phenotype of the pods: When the pods were fully grown and filled, just prior to yellowing, the degree of sharpness of the zone that delineates the valve and beak at the zone where both valves are not touching anymore (at distal end of pod) of 5 random pods (from different plants if multiple plants per line are available) was assessed and attributed a score from 0 to 10 or from 1 to 5:0 or 1, respectively, for a clear indentation and fine sharp zone that separates valve and beak; 1-3 or 2, respectively, for some indentation and clear, though more fuzzy, zone that separates valve from beak; 4-6 or 3, respectively, for valves and beak that are still well observable as two different tissues but with a very smooth transition between them; 7-9 or 4, respectively, for valves and beak that are barely observable as different tissues; 10 or 5, respectively, for a completely smoothened transition between valves and beak without any clear differentiation between both tissue types, i.e. the less indentation between the valve and the beak at the distal end of the pods the higher the score. A score of 0 or 1, respectively, (sharp indentation between the valve and the beak) corresponds to a wildtype phenotype of the pods, more specifically a pod shatter sensitive phenotype of the pods; a score of 1 to 9 or 2 to 4, respectively, (more gradual transition between the valve and the beak) corresponds to a pod shatter resistant phenotype of the pods, wherein seed shattering is significantly reduced or delayed while an agronomically relevant treshability of the pods is maintained, such that the pods may still be opened along the dehiscence zone by applying limited physical forces; and a score of 10 or 5, respectively, (no indentation between the valve and the beak) corresponds to a pod shatter resistant phenotype of the pods, wherein seed shattering is reduced or delayed to a degree which does not allow an agronomically relevant treshability of the pods anymore, such that the pods cannot be opened along the dehiscence zone by applying limited physical forces.
(b) Manual Impact Test (MIT) to determine the increase in pod shatter resistance caused by the presence of different partial and/or full knockout mutant IND genes: The level of pod shatter resistance of *Brassica napus* lines comprising a partial knockout mutant IND gene in homozygous state alone or both a partial and a full knockout mutant IND gene in homozygous state and of *Brassica* lines comprising the corresponding wild type IND alleles was compared in a semi-quantitative way by determining the physical forces needed to open closed mature pods by manually applying torsion on the pods. The podshatter resistance of the pods was attributed a score from 1 to 5 based on this physical force: 1 for pods which completely open along the dehiscence zone at the slightest torsion, 2-4 for pods which open only at the base of the dehiscence zone and need stronger torsion to open completely and 5 for pods which can only be crushed and do not open along the dehiscence zone.
(c) Random Impact Test (RIT) to determine the increase in pod shatter resistance caused by the presence of different partial and/or full knockout mutant IND genes: The level of pod shatter resistance of *Brassica napus* lines comprising a partial knockout mutant IND gene in homozygous state alone or both a partial and a full knockout mutant IND gene in homozygous state and of *Brassica* lines comprising the corresponding wild type IND alleles was compared in a quantitative way by determining the half life of samples of pods from both lines according to Bruce et al. (2002, supra). More specifically, two replicate samples of 20 intact mature pods from each line were subjected to a RIT. 20 pods were placed together with six steel balls of 12.5 mm diameter in a cylindrical container of diameter 20 cm with its axis vertical. The container was then subjected to simple harmonic motion of frequency 4.98 Hz and of stroke 51 mm in the horizontal plane. The pods, checked for soundness before the test, were shaken for cumulative times of 10, 20, 40, and, if more than 50% of pods remained intact, 80 s. The drum was opened after each period and the number of closed pods counted. The pods were examined and classed as "closed" if the dehiscence zone of both valves was still closed. Thus the pods were classed as "opened" if one or both of the valves was detached, so that the seed had been released. If the majority of the pods was broken or damaged without opening of the dehiscence zone, the sample was marked "uncountable" (indicated with * in Table 5b). To give each point equal weighing, the data were made evenly spaced in the independent variable, time, by adding 1 and taking $\log_{10}$. The percentage of pods opened p was transformed by the logit transformation, i.e. logit $p=\log_e(p/100-p)$. A linear model was then fitted to the transformed time and percentage data and used to estimate the half-life.

(d) Field tests to determine the relationship between pod shatter resistance, treshability and yield and the presence of certain mutant IND alleles in plants: The level of pod shatter resistance, treshability and yield of *Brassica* lines comprising the mutant IND alleles and *Brassica* lines comprising the corresponding wild type IND alleles was compared in a semi-quantitative way by determining and comparing the level of seed shattering (SHAT), combiner harvest ability (CHA1) and treshing ability (CHA2) and in a quantitative way by determining and comparing seed yield per plot after combining (YLDP) and seed yield after treshing of straw (YLDS) in the field between plots with ind plants and plots with wild-type plants. The plots were attributed a score of 1-9 to indicate the level of seed shattering on the plot before harvest: a score of 1 to indicate that practically all plants on the plot were shattering before harvest to a score of 9 to indicate that practically no plants on the plot were shattering before harvest. The plots were attributed a score of 1-5 to indicate the level of combiner harvest ability on the plot: a score of 1, to 3 or to 5 to indicate that it was difficult, to feasible, or to easy, respectively, to harvest the plot with a combiner. The plots were attributed a score of 1-5 to indicate the level of treshing ability of the plot: a score of 1, to 3 or to 5 to indicate that it was difficult, to feasible, or to easy, respectively, to manually harvest the seed remaining in the straw after combiner harvest. The seed yield per plot after combining (YLDP; expressed in grams per plot) was determined by harvesting the seeds per plot with a combine harvester and weighing the seeds and the seed yield after treshing of straw (YLDS; expressed in weight % of the straw) was determined by manually harvesting the seeds remaining in the straw after seed harvest with the combine harvester.

To examine more closely whether and how cells at the valve margin of seed pods are affected by the presence of partial and/or full knockout mutant IND genes, sections of ind fruit were compared to sections of wild-type fruit by microscopic evaluation of the seed pods:

Explants: Explants of about 3 mm taken from the center and the distal ends of pods of similar developmental stage (about 35 days after anthesis (DAA), a stage of development which closely corresponds to the onset of visible pericarp yellowing) and size were harvested from plants grown in a greenhouse (three pods for each genotype). One dehiscence zone was dissected from the pods.

Fixation: Fixation was done in 100 mM K-phosphate buffer pH7 with 10% formalin and 0.25% glutaraldehyde for a total of 4 hours. Vacuum infiltration was done after 1 and 2 hours for 15 minutes. The fixative was renewed after each vacuum infiltration.

Dehydration: The specimen was rinsed 2 times 30 minutes with 100 mM K-phosphate buffer pH7. Dehydration was done with technical ethanol diluted with 0.85% NaCl in water: 60 minutes (') in 50% ethanol, 90' in 70% ethanol, 90' in 80% ethanol, 90' in 90% ethanol, 90' in 95% ethanol, 90' in 100% ethanol at room temperature Embedding: Embedding was done with The Leica 7022-31731 Historesin or the Kulzer Histo-Technik 7100 (Heraeus) embedding kits, which are three component resin (a basic resin, an activator and a hardener) kits. The three components were used in the proportions as advised by the manufacturer as follows: the specimen were incubated for 4 hours in 50% ethanol/50% basic resin, overnight in 30% ethanol/70% basic resin (optional: at 4° C.), for 2 to 4 hours in 100% basic resin, for one day in 100% basic resin after renewing the basic resin and vacuum infiltration for 20' (optionally at 4° C.), for one day in basic resin+activator (1%) ("infiltration medium") after vacuum infiltration in this medium for 20 minutes. The specimen was washed with basic resin+activator (1%)+hardener (1 ml in 15 ml) ("embedding medium"). The embedding was done in flat embedding moulds (AGAR flat embedding moulds G3531 with cavities of about 300 µl: 14 mm long×6 mm wide×4 mm deep): 100-125 µl of embedding medium/cavity was added, the embedding medium was polymerized at 55° C. for about one hour, the tissue was put on the polymerized embedding medium (1 explant/cavity), the cavities ware filed with embedding medium, the embedding medium was polymerized for 3 to 5 hours at 55° C., the moulds were could down, the plastic blocks were removed from the moulds and stored at room temperature in a sealed container (e.g. eppendorf tube).

Sectioning: The plastic blocks were glued with the flat side on a 1 cm³ perpex block and trimmed squarely around the specimen. 4 µm sections (3 to 4 explants per genotype, about 25 sections per explant) were cut with a ralph glass knife (made on −1 position of the histoknifemaker of Reichert-Jung using 6 mm thick glass rods under a cutting angle of about 6°) on the microtome. The sections were attached on glass slides treated with Vectabond (Vector laboratories).

Demonstration of lignin: unstained sections mounted in Eukitt were examined using a microscope equipped for fluorescence (with Zeiss filter set 02). Lignin fluoresces clear bluish Evaluation of histology: unstained sections were visualized by using DIC-Normaski or autofluorescence (with Zeiss filter set 18—Excitation BP390-420; Emission LP450).

Plant Material:

Progeny of a plant line comprising a full knockout mutation in the IND A1 gene (indicated as ind-a1$^F$), in particular the ind-a1-EMS01 allele described in WO09/068313 (claiming priority of European patent application EP 07023052) (indicated as ind-a1-01 in Table 5), and a partial knockout mutation in the IND-C1 gene (indicated as ind-c1$^P$), in particular the ind-c1-EMS04, -EMS08 and -EMS09 alleles indicated in Table 3b (indicated as ind-c1-04, -08, and -09 in Table 5), with genotype ind-a1$^F$/ind-a1$^F$, ind-c1$^P$/ind-c1$^P$ (i.e., homozygous double mutant plants), IND-A1/IND-A1, ind-c1$^P$/ind-c1$^P$ (i.e., homozygous single mutant plants), and IND-A1/IND-A1, IND-C1/IND-C1 (i.e., wildtype plants).

Progeny of a plant line comprising a partial knockout mutation in the IND-A1 gene (indicated as ind-a1$^P$), in particular the ind-a1-EMS06, -EMS09 and -EMS13 alleles indicated in Table 3a (indicated as ind-a1-06, -09, and -13 in Table 5), and a full knockout mutation in the IND-C1 gene (indicated as ind-c1$^F$), in particular the ind-c1-EMS01 allele and the ind-c1-EMS03 allele described in WO09/068313 (claiming priority of European patent application EP 07023052) (indicated as ind-c1-01 and -03 in Table 5), with genotype ind-a1$^P$/ind-a1$^P$, ind-c1$^F$/ind-c1$^F$ (i.e., homozygous double mutant plants), IND-A1/IND-A1, ind-c1$^F$/ind-c1$^F$ (i.e., homozygous single mutant plants), and IND-A1/IND-A1, IND-C1/IND-C1 (i.e., wildtype plants).

Macroscopical Evaluation:

a) Inspection of the Seed Pods and Plants with Naked Eye.

The pods from homozygous double mutant IND sibling plants with genotype ind-a1$^F$/ind-a1$^F$, ind-c1$^P$/ind-c1$^P$ or ind-a1$^P$/ind-a1$^P$, ind-c1$^F$/ind-c1$^F$ showed a phenotype similar to the pods from plants comprising one full knockout ind allele in homozygous state and one full knockout ind allele in heterozygous state described in WO09/068313 (claiming priority of European patent application EP 07023052) (genotype: ind-a1$^F$/ind-a1$^F$, IND-C1/ind-c1$^F$ or IND-A1/ind-a1$^F$, ind-c1$^P$/ind-c1$^P$, wherein ind-a1$^F$ is a full knockout ind-a1 allele, in particular the ind-a1-EMS01 or ind-a1-EMS05 allele described in WO09/068313 (claiming priority of European patent application EP 07023052), and wherein ind-c1$^F$ is a full knockout ind-c1 allele, in particular the ind-c1-EMS01 or ind-c1-EMS03 allele described in WO09/068313 (claiming priority of European patent application EP 07023052)). More specifically, the valve margins of the pods of these mutant IND sibling plants were in general better defined than in the homozygous double full knockout mutant IND sibling plants described in WO09/068313 (claiming priority of European patent application EP 07023052) (which showed a lack of proper valve margin definition, particularly apparent at both the proximal and distal end of the fruit, as compared to the pods from wild-type IND sibling plants), but the sharp indentation between the valve and the beak at the distal end of the pods in the wild-type sibling plants was still largely absent in these mutant plants as in the homozygous double full knockout ind sibling plants, which also showed a more gradual transition between valve and beak tissue (see also visual score in Table 5a for glasshouse grown plants and in Table 5b for field grown plants).

The pods from homozygous single mutant IND sibling plants (genotype: IND-A1/IND-A1, ind-c1$^P$/ind-c1$^P$ or ind-a1$^P$/ind-a1$^P$, IND-C1/IND-C1) showed a pod morphology similar to pods from wild-type IND sibling plants, except for pods from homozygous single mutant IND sibling plants with genotype IND-A1-EMS01/IND-A1-EMS01, ind-c1-EMS09/ind-c1-EMS09, which showed an altered pod morphology similar to pods from the homozygous double mutant IND sibling plants with genotype ind-a1$^F$/ind-a1$^F$, ind-c1$^P$/ind-c1$^P$ or ind-a1$^P$/ind-a1$^P$, ind-c1$^F$/ind-c1$^F$ (see also visual score in Table 5a for glasshouse grown plants and in Table 5b for field grown plants). It was further observed that the presence of the ind-c1-EMS09 allele in heterozygous state in plants (genotype: IND-A1/IND-A1, IND-C1/ind-c1-EMS09) was sufficient to cause an altered pod morphology similar to pods from the homozygous double mutant IND sibling plants with genotype ind-a1$^F$/ind-a1$^P$, ind-c1$^P$/ind-c1$^P$ or ind-a1$^P$/ind-a1$^P$, ind-c1$^F$/ind-c1$^F$. It is thought that the ind-c1-EMS09 allele, which comprises a substitution mutation in a conserved amino acid of the basic DNA binding domain, might produce a dominant negative IND protein that is still capable of dimer formation, but not capable of binding to the bHLH binding site of the regulated gene(s).

b) Random Impact Test:

Table 5 shows that the LD50 value was in general higher for pods from plants comprising a full knockout ind-c1 allele in homozygous state and a partial knockout ind-a1 allele in homozygous state than for pods from plants comprising a full knockout ind-a1 allele in homozygous state and a partial knockout ind-c1 allele in homozygous state indicating that the mutations in the IND-C1 allele could have a stronger effect on pod shatter resistance than the mutations in the IND-A1 allele.

TABLE 5a

| Genotype | Visual pod Score (0-10) | LD50 (sec) | Corrected Lower 95% | Corrected Upper 95% |
| --- | --- | --- | --- | --- |
| IND-A1-06/IND-A1-06, IND-C1-01/IND-C1-01 | 0 | 8.06 | 3.1 | 1.78 |
| ind-a1-06/ind-a1-06, IND-C1-01/IND-C1-01 | 0 | 9.05 | 2.83 | 2.15 |
| ind-a1-06/ind-a1-06, ind-c1-01/ind-c1-01 | 7 | 26.31 | 4.83 | 7.64 |
| IND-A1-06/IND-A1-06, IND-C1-03/IND-C1-03 | 0 | 8.86 | * | * |
| ind-a1-06/ind-a1-06, IND-C1-03/IND-C1-03 | 0 | 5.74 | 4.2 | 2.06 |
| ind-a1-06/ind-a1-06, ind-c1-03/ind-c1-03 | 7 | 29.38 | 3.8 | 5.18 |
| IND-A1-09/IND-A1-09, IND-C1-01/IND-C1-01 | 0 | 9.36 | 2.6 | 1.7 |
| ind-a1-09/ind-a1-09, IND-C1-01/IND-C1-01 | 1 | 9.05 | 2.83 | 2.15 |
| ind-a1-09/ind-a1-09, ind-c1-01/ind-c1-01 | 8 | 52.03 | 8.96 | 14.03 |
| IND-A1-09/IND-A1-09, IND-C1-03/IND-C1-03 | 0 | 8.44 | 2.74 | 2.26 |
| ind-a1-09/ind-a1-09, IND-C1-03/IND-C1-03 | 0 | 9.05 | 2.83 | 2.15 |
| ind-a1-09/ind-a1-09, ind-c1-03/ind-c1-03 | 8.5 | 85.57 | 23.34 | 64.64 |
| IND-A1-13/IND-A1-13, IND-C1-01/IND-C1-01 | 3 | 12.91 | 2.4 | 2.46 |
| ind-a1-13/ind-a1-13, IND-C1-01/IND-C1-01 | 2 | 14.2 | 2.2 | 2.59 |
| ind-a1-13/ind-a1-13, ind-c1-01/ind-c1-01 | 7 | 61.21 | 9.6 | 15.18 |
| IND-A1-13/IND-A1-13, IND-C1-03/IND-C1-03 | 0 | 8.86 | * | * |
| ind-a1-13/ind-a1-13, IND-C1-03/IND-C1-03 | 0 | 7.74 | 3.98 | 1.54 |

TABLE 5a-continued

| Genotype | Visual pod Score (0-10) | LD50 (sec) | Corrected Lower 95% | Corrected Upper 95% |
|---|---|---|---|---|
| ind-a1-13/ind-a1-13, ind-c1-03/ind-c1-03 | 9 | 56.68 | 8.9 | 13.6 |
| IND-A1-01/IND-A1-01, IND-C1-04/IND-C1-04 | 0 | 7.89 | 2.88 | 2 |
| IND-A1-01/IND-A1-01, ind-c1-04/ind-c1-04 | 0 | 10.91 | 2.5 | 2 |
| ind-a1-01/ind-a1-01, ind-c1-04/ind-c1-04 | 9 | 37.8 | 5.77 | 8.4 |
| IND-A1-01/IND-A1-01, IND-C1-08/IND-C1-08 | 0 | 8.94 | 2.78 | 2.38 |
| IND-A1-01/IND-A1-01, ind-c1-08/ind-c1-08 | 0 | 9.8 | 2.8 | 2.1 |
| ind-a1-01/ind-a1-01, ind-c1-08/ind-c1-08 | 8.5 | 31.81 | 6.66 | 10.45 |
| IND-A1-01/IND-A1-01, IND-C1-09/IND-C1-09 | 0 | 7.22 | 3.56 | 1.82 |
| IND-A1-01/IND-A1-01, ind-c1-09/ind-c1-09 | 8.5 | 46.6 | 7.82 | 11.48 |
| ind-a1-01/ind-a1-01, ind-c1-09/ind-c1-09 | 9 | 90.11 | * | * |

TABLE 5b

| Genotype | Visual pod score (1-5) | Score based on physical force needed to open closed mature pods (1-5) | LD50 (sec) field 1 | LD50 (sec) field 2 |
|---|---|---|---|---|
| IND-A1-06/IND-A1-06, IND-C1-01/IND-C1-01 | 1 | 1 | 9.7 | 7.2 |
| ind-a1-06/ind-a1-06, IND-C1-01/IND-C1-01 | 1 | 1 | 6.2 | 8.3 |
| ind-a1-06/ind-a1-06, ind-c1-01/ind-c1-01 | 2 | 2 | 17.0 | 16.6 |
| IND-A1-06/IND-A1-06, IND-C1-03/IND-C1-03 | 1 | 1 | 6.5 | 6.6 |
| ind-a1-06/ind-a1-06, IND-C1-03/IND-C1-03 | 1 | 1 | 7.4 | 5.3 |
| ind-a1-06/ind-a1-06, ind-c1-03/ind-c1-03 | 3 | 2 | 15.3 | 12.4 |
| IND-A1-09/IND-A1-09, IND-C1-01/IND-C1-01 | 1 | 1 | 7.5 | 6.9 |
| ind-a1-09/ind-a1-09, IND-C1-01/IND-C1-01 | 1 | 1 | 5.4 | 7.2 |
| ind-a1-09/ind-a1-09, ind-c1-01/ind-c1-01 | 3 | 4 | 60.1 | 77.0 |
| IND-A1-09/IND-A1-09, IND-C1-03/IND-C1-03 | 1 | 1 | 6.6 | 6.2 |
| ind-a1-09/ind-a1-09, IND-C1-03/IND-C1-03 | 1 | 1 | 7.7 | 7.0 |
| ind-a1-09/ind-a1-09, ind-c1-03/ind-c1-03 | 3 | 4 | 49.8 | 63.0 |
| IND-A1-13/IND-A1-13, IND-C1-01/IND-C1-01 | 1 | 1 | 11.7 | 10.7 |
| ind-a1-13/ind-a1-13, IND-C1-01/IND-C1-01 | 1 | 1 | 10.7 | 7.9 |
| ind-a1-13/ind-a1-13, ind-c1-01/ind-c1-01 | 3 | 3 | 19.1 | 22.9 |
| IND-A1-13/IND-A1-13, IND-C1-03/IND-C1-03 | 1 | 1 | 5.4 | 5.7 |
| ind-a1-13/ind-a1-13, IND-C1-03/IND-C1-03 | 1 | 1 | 9.2 | 8.3 |
| ind-a1-13/ind-a1-13, ind-c1-03/ind-c1-03 | 3 | 3 | 10.2 | 38.6 |
| IND-A1-01/IND-A1-01, IND-C1-04/IND-C1-04 | 1 | 1 | 6.5 | 7.4 |
| IND-A1-01/IND-A1-01, ind-c1-04/ind-c1-04 | 1 | 2 | 9.5 | 7.2 |
| ind-a1-01/ind-a1-01, ind-c1-04/ind-c1-04 | 3 | 5 | 87.7 | 126.6 |
| IND-A1-01/IND-A1-01, IND-C1-08/IND-C1-08 | 1 | 1 | 9.7 | 8.3 |
| IND-A1-01/IND-A1-01, ind-c1-08/ind-c1-08 | 1 | 1 | 4.9 | 9.0 |
| ind-a1-01/ind-a1-01, ind-c1-08/ind-c1-08 | 3 | 3 | 14.9 | 23.7 |
| IND-A1-01/IND-A1-01, IND-C1-09/IND-C1-09 | 1 | 1 | 9.1 | 8.3 |
| IND-A1-01/IND-A1-01, ind-c1-09/ind-c1-09 | 3 | 2 | 7.9 | 8.3 |
| ind-a1-01/ind-a1-01, ind-c1-09/ind-c1-09 | 5 | 5 | * | * |

*: uncountable c) Field Tests

Table 5c shows the level of seed shattering (SHAT), combiner harvest ability (CHA1), treshing ability (CHA2), seed yield per plot after combining (YLDP) and seed yield after treshing of straw (YLDS) determined as described above for field plots with ind plants and wild-type plants as indicated. The YieldWTSeg % value represents the YLDP as a percentage of the wildtype segregant within one segregating population.

TABLE 5c

| Genotype | SHAT (1-9) | CHA1 (1-5) | CHA2 (1-5) | YLDP (in grams per plot) | Yield WTSeg % | YLDS (in wt % of straw) |
|---|---|---|---|---|---|---|
| IND-A1-06/IND-A1-06, IND-C1-01/IND-C1-01 | 8.3 | 5.0 | 5.0 | 2263.3 | 100 | 0.4 |
| ind-a1-06/ind-a1-06, IND-C1-01/IND-C1-01 | 8.4 | 4.6 | 5.0 | 2274.9 | 101 | 0.3 |
| ind-a1-06/ind-a1-06, ind-c1-01/ind-c1-01 | 8.7 | 4.4 | 4.9 | 2525.1 | 112 | 1.1 |
| IND-A1-06/IND-A1-06, IND-C1-03/IND-C1-03 | 8.6 | 4.6 | 4.9 | 2102.0 | 100 | 0.5 |
| ind-a1-06/ind-a1-06, IND-C1-03/IND-C1-03 | 8.7 | 4.8 | 5.0 | 2292.7 | 109 | 0.4 |
| ind-a1-06/ind-a1-06, ind-c1-03/ind-c1-03 | 8.8 | 4.1 | 4.6 | 2276.2 | 108 | 1.3 |

TABLE 5c-continued

| Genotype | SHAT (1-9) | CHA1 (1-5) | CHA2 (1-5) | YLDP (in grams per plot) | Yield WTSeg % | YLDS (in wt % of straw) |
|---|---|---|---|---|---|---|
| IND-A1-09/IND-A1-09, IND-C1-01/IND-C1-01 | 8.3 | 5.0 | 4.9 | 1964.2 | 100 | 0.3 |
| ind-a1-09/ind-a1-09, IND-C1-01/IND-C1-01 | 8.0 | 4.7 | 5.0 | 1872.0 | 95 | 0.4 |
| ind-a1-09/ind-a1-09, ind-c1-01/ind-c1-01 | 9.0 | 2.7 | 3.8 | 2323.3 | 118 | 5.7 |
| IND-A1-09/IND-A1-09, IND-C1-03/IND-C1-03 | 8.6 | 4.8 | 5.0 | 2168.9 | 100 | 0.5 |
| ind-a1-09/ind-a1-09, IND-C1-03/IND-C1-03 | 8.3 | 4.7 | 5.0 | 1985.6 | 92 | 0.4 |
| ind-a1-09/ind-a1-09, ind-c1-03/ind-c1-03 | 9.0 | 1.9 | 3.6 | 1726.7 | 80 | 13.6 |
| IND-A1-13/IND-A1-13, IND-C1-01/IND-C1-01 | 8.3 | 4.8 | 5.0 | 1977.1 | 100 | 0.4 |
| ind-a1-13/ind-a1-13, IND-C1-01/IND-C1-01 | 8.4 | 4.2 | 4.9 | 1929.3 | 98 | 0.5 |
| ind-a1-13/ind-a1-13, ind-c1-01/ind-c1-01 | 8.9 | 3.6 | 4.7 | 2445.6 | 124 | 2.0 |
| IND-A1-13/IND-A1-13, IND-C1-03/IND-C1-03 | 8.3 | 4.2 | 5.0 | 1885.1 | 100 | 0.4 |
| ind-a1-13/ind-a1-13, IND-C1-03/IND-C1-03 | 8.3 | 4.8 | 5.0 | 2137.8 | 113 | 0.6 |
| ind-a1-13/ind-a1-13, ind-c1-03/ind-c1-03 | 8.9 | 2.8 | 3.9 | 2120.9 | 113 | 4.8 |
| IND-A1-01/IND-A1-01, IND-C1-04/IND-C1-04 | 8.8 | 4.9 | 4.8 | 2120.4 | 100 | 0.6 |
| IND-A1-01/IND-A1-01, ind-c1-04/ind-c1-04 | 8.6 | 4.8 | 5.0 | 2136.4 | 101 | 0.6 |
| ind-a1-01/ind-a1-01, ind-c1-04/ind-c1-04 | 9.0 | 1.8 | 2.8 | 1437.0 | 68 | 19.1 |
| IND-A1-01/IND-A1-01, IND-C1-08/IND-C1-08 | 8.0 | 4.8 | 5.0 | 2250.4 | 100 | 0.6 |
| IND-A1-01/IND-A1-01, ind-c1-08/ind-c1-08 | 8.3 | 4.3 | 4.9 | 2131.3 | 95 | 0.5 |
| ind-a1-01/ind-a1-01, ind-c1-08/ind-c1-08 | 8.9 | 3.0 | 4.1 | 2385.1 | 106 | 2.5 |
| IND-A1-01/IND-A1-01, IND-C1-09/IND-C1-09 | 8.7 | 4.9 | 5.0 | 2080.0 | 100 | 0.4 |
| IND-A1-01/IND-A1-01, ind-c1-09/ind-c1-09 | 8.7 | 4.6 | 4.6 | 2447.8 | 118 | 1.0 |
| ind-a1-01/ind-a1-01, ind-c1-09/ind-c1-09 | 9.0 | 1.1 | 1.8 | 589.6 | 28 | 28.4 |

Microscopical Evaluation:

The pods from homozygous double mutant IND sibling plants with genotype ind-a1$^F$/ind-a1$^F$, ind-c1$^F$/ind-c1$^F$ or ind-a1$^F$/ind-a1$^F$, ind-c1$^F$/ind-c1$^F$ and the pods from homozygous single mutant IND sibling plants with genotype IND-A1-EMS01/IND-A1-EMS01, ind-c1-EMS09/ind-c1-EMS09, grown under greenhouse conditions, showed at their distal ends lignification throughout the complete dehiscence zone and a poor differentiation of cells belonging to the dehiscence zone from neighboring cell types, such as the vascular tissue cells and the lignified layer of cells normally found at the inner pod wall (i.e. the enb cells). At the center of the pods, lignification did not occur throughout the complete dehiscence zone but the pods displayed only a few extra layers of lignified cells instead where the inner pod wall is attached to the septum.

The pods from homozygous double mutant IND sibling plants with genotype ind-a1-EMS01/ind-aA1-EMS01, ind-c1-EMS09/ind-c1-EMS09 showed both at their distal ends and at the center of the pods lignification throughout the complete dehiscence zone and a poor differentiation of cells belonging to the dehiscence zone from neighboring cell types, such as the vascular tissue cells and the lignified layer of cells normally found at the inner pod wall (i.e. the enb cells).

Example 4

Detection and/or Transfer of Mutant IND Genes into (Elite) Brassica Lines

The mutant IND genes are transferred into (elite) Brassica breeding lines by the following method: A plant containing a mutant IND gene (donor plant), is crossed with an (elite) Brassica line (elite parent/recurrent parent) or variety lacking the mutant IND gene. The following introgression scheme is used (the mutant IND gene is abbreviated to ind while the wild type is depicted as IND):

Initial cross: ind/ind (donor plant)×IND/IND (elite parent)
F1 plant: IND/ind
BC1 cross: IND/ind×IND/IND (recurrent parent)
BC1 plants: 50% IND/ind and 50% IND/IND
The 50% IND/ind are selected using molecular markers (e.g. AFLP, PCR, Invader™, and the like; see also below) for the mutant IND allele (ind).
BC2 cross: IND/ind (BC1 plant)×IND/IND (recurrent parent)
BC2 plants: 50% IND/ind and 50% IND/IND
The 50% IND/ind are selected using molecular markers for the mutant IND allele (ind).
Backcrossing is repeated until BC3 to BC6
BC3-6 plants: 50% IND/ind and 50% IND/IND
The 50% IND/ind are selected using molecular markers for the mutant IND allele (ind). To reduce the number of backcrossings (e.g. until BC3 in stead of BC6), molecular markers can be used specific for the genetic background of the elite parent.
BC3-6 S1 cross: IND/ind×IND/ind
BC3-6 S1 plants: 25% IND/IND and 50% IND/ind and 25% ind/ind
Plants containing ind are selected using molecular markers for the mutant IND allele (ind). Individual BC3-6 S1 plants that are homozygous for the mutant IND allele (ind/ind) are selected using molecular markers for the mutant and the wild-type IND alleles. These plants are then used for seed production.

To select for plants comprising a point mutation in an IND allele, direct sequencing by standard sequencing techniques known in the art, such as those described in Example 1, can be used.

Alternatively, PCR assays can be developed to discriminate plants comprising a specific point mutation in an IND allele from plants not comprising that specific point mutation. The following discriminating PCR assays can thus be developed to detect the presence or absence and the zygosity status of the mutant alleles identified in Example 1 (see Table 3a and 3b):

Template DNA:
  Genomic DNA isolated from leaf material of homozygous or heterozygous mutant Brassica plants (comprising a mutant IND allele, called hereinafter "IND-Xx-EMSXX").

Wild type DNA control: Genomic DNA isolated from leaf material of wild type *Brassica* plants (comprising the wild type equivalent of the mutant IND allele, called hereinafter "IND-Xx-WT").

Positive DNA control: Genomic DNA isolated from leaf material of homozygous mutant *Brassica* plants known to comprise IND-Xx-EMSXX.

Generally, each primer set consists of one primer specific for both the mutant and the wild type target gene (e.g. primer specific for both the IND-A1-EMS06 and the IND-A1-WT allele) and one primer specific for the nucleotide difference (e.g. primer specific for either the IND-A1-EMS06 allele or the IND-A1-WT allele). Usually, the last nucleotide of the latter primer matches with the nucleotide difference, but one (or more) additional target specific nucleotide(s) may be added to improve the annealing between the primer and its target sequence.

PCR mix: 2.5 µl 10×PCR buffer (15 mM MgCl2), 0.25 µl dNTP's (20 mM), 1 µl forward primer (10 µM), 1 µl reverse primer (10 µM), 0.25 µl Taq-polymerase (5 U/µl), 19.5 µl Milli-Q H$_2$O, 0.5 µl DNA (20-50 ng/µl)= Total volume of 25 µl;

Thermocycling profile: 4 min at 95° C.; 30×[1 min at 95° C. (denaturation) and 1 min at annealing temperature and 2 min at 72° C. (elongation)]; 5 min at 72° C.; cool down to 4° C. The optimal annealing temperature can be determined by temperature gradient PCR wherein the annealing temperature can be varied e.g. between 57° C. to 70° C. on a MJ Research thermocycler PTC-200 (Biozym). The optimal annealing temperature for the wild type IND specific primers is that temperature at which a clear PCR fragment of the expected size can be detected (as described below) for the DNA sample from the wild type *Brassica* plant and not for the DNA sample from the mutant *Brassica* plant. The optimal annealing temperature for the mutant IND specific primers is that temperature at which a clear PCR fragment of the expected size can be detected (as described below) for the DNA sample from the mutant *Brassica* plant and not for the DNA sample from the wild type *Brassica* plant.

After amplification, 5 µl loading dye (orange dye) is added to 15 µl of the PCR samples and the samples are loaded on a 1.5% agarose gel.

The banding patterns obtained after amplification of genomic DNA of mutant *Brassica* plants are evaluated as follows:

Data from DNA samples isolated from leaf material of the mutant *Brassica* plants within a single PCR run and a single PCR mix should not be accepted unless:

the wild-type DNA control shows the PCR fragment of the expected size for the IND-Xx-WT specific PCR assay and no PCR fragment of the expected size for the IND-Xx-EMSXX specific PCR assay the positive DNA control shows the PCR fragment of the expected size for the IND-Xx-EMSXX specific PCR assay and no PCR fragment of the expected size for the IND-Xx-WT specific PCR assay Lanes showing no PCR product of the expected size for the IND-Xx-WT specific PCR assay and the PCR fragment of the expected size for the IND-Xx-EMSXX specific PCR assay, indicate that the corresponding plant from which the genomic template DNA was prepared, is a homozygous mutant for IND-Xx-EMSXX.

Lanes showing the PCR fragment of the expected size for the IND-Xx-WT specific PCR assay and the IND-Xx-EMSXX specific PCR assay, indicate that the corresponding plant from which the genomic template DNA was prepared, is a heterozygous mutant for IND-Xx-EMSXX.

Lanes showing the PCR fragment of the expected size for the IND-Xx-WT specific PCR assay and no PCR product of the expected size for the IND-Xx-EMSXX specific PCR assay, indicate that the corresponding plant from which the genomic template DNA was prepared, is a wild type plant.

Alternatively, Invader™ technology (Third Wave Agbio) can be used to discriminate plants comprising a specific point mutation in an IND allele from plants not comprising that specific point mutation. The following discriminating Invader™ probes were thus developed to detect the presence or absence and the zygosity status of the mutant alleles identified in Example 4 (see Table 6:

Probes specific for the mutant or corresponding wild-type target IND gene (indicated as "5' flap1-x" and "5' flap2-x", respectively) and "invading" probes which can be used in combination with them are indicated in Table 6. Generally, each probe set consists of one probe specific for the mutant or the wild type target gene of which the first nucleotide after the 5' flap sequence matches with the nucleotide difference (underlined nucleotide in Table 6) (the so-called "primary probe"; e.g. the probe with SEQ ID NO: 12 is specific for IND-A1-EMS06 and the probe with SEQ ID NO: 13 is specific for IND-A1-WT) and one probe specific for the nucleotides upstream of the nucleotide difference (the so-called "Invader® oligo"; e.g. the probe with SEQ ID NO: 11 is specific for the nucleotides upstream of the nucleotide difference between IND-A1-EMS06 and IND-A1-WT). The last nucleotide of the latter primer may match with the nucleotide difference in the mutant (as indicated by the bold nucleotides in Table 6), but other nucleotides may be used as well for this last nucleotide as long as the primary probe and the Invader® oligo are still able to form a single base overlap when hybridized to the target DNA to generate the specific invasive structure recognized by the Cleavase® enzymes (Third Wave Agbio).

The Invader™ assay procedure and interpretation of the data are performed as prescribed by the manufacturer (Third Wave Agbio). Briefly, the nucleotide sequences indicated as "flap 1" and "flap2" in Table 6 represent the sequences of the 5' "flaps" which are cleaved from the primary probes in the primary phase of the Invader™ assay and which are complementary to sequences in FRET™ cassette 1 and 2, respectively, and not complementary to the target mutant or wild type sequences. If the primary probes are cleaved in the primary phase and the flap1-probe and/or flap2-probe hybridise to FRET™ cassette 1 and 2, respectively, in the secondary phase, a signal is generated indicative of the presence in the sample of the mutant or corresponding wild-type target IND gene, respectively.

TABLE 6

| Allele No. | Probes | |
|---|---|---|
| IND-A1-EMS06 | 5' CGTAAGGGTAAGCGACGACCCTCAGACGT 3' | (SEQ ID NO: 11) |
| | 5' flap1-<u>A</u>TGGTGGCTCGTCG 3' | (SEQ ID NO: 12) |
| IND-A1-WT | 5' CGTAAGGGTAAGCGACGACCCTCAGACGT 3' | (SEQ ID NO: 11) |
| | 5' flap2-<u>G</u>TGGTGGCTCGTC 3' | (SEQ ID NO: 13) |
| IND-A1-EMS09 | 5' GGAGGCAGTGTCCATCTTTGCACCGCA 3' | (SEQ ID NO: 14) |
| | 5' flap1-<u>T</u>TGGCACCATCCTCT 3' | (SEQ ID NO: 15) |
| IND-A1-WT | 5' GGAGGCAGTGTCCATCTTTGCACCGCA 3' | (SEQ ID NO: 14) |
| | 5' flap2-<u>C</u>TGGCACCATCCTCT 3' | (SEQ ID NO: 16) |
| IND-A1-EMS13 | 5' CCTGCCGTTTCAAGAACTTGGTGTAGCGGATGT 3' | (SEQ ID NO: 17) |
| | 5' flap1-<u>A</u>CTTCGTCGAGCATG 3' | (SEQ ID NO: 18) |
| IND-A1-WT | 5' GGAGGCAGTGTCCATCTTTGCACCGCA 3' | (SEQ ID NO: 17) |
| | 5' flap2-<u>G</u>CTTCGTCGAGCATG 3' | (SEQ ID NO: 19) |
| IND-C1-EMS04 | 5' CATCCTCTTCAATATCCGGATCTTCTCGCTTATCCTTTCTCTACT 3' | (SEQ ID NO: 20) |
| | 5' flap1-<u>A</u>CCGACGAGCCAC 3' | (SEQ ID NO: 21) |
| IND-C1-WT | 5' CATCCTCTTCAATATCCGGATCTTCTCGCTTATCCTTTCTCTACT 3' | (SEQ ID NO: 20) |
| | 5' flap2-<u>G</u>CCGACGAGCCAC 3' | (SEQ ID NO: 22) |
| IND-C1-EMS08 | 5' CGTAAGGGTAAGCGAGGACCCCCAGA 3' | (SEQ ID NO: 23) |
| | 5' flap1-<u>T</u>GGTGGTGGCTCG 3' | (SEQ ID NO: 24) |
| IND-C1-WT | 5' CGTAAGGGTAAGCGAGGACCCCCAGA 3' | (SEQ ID NO: 23) |
| | 5' flap2-<u>C</u>GGTGGTGGCTCG 3' | (SEQ ID NO: 25) |
| IND-C1-EMS09 | 5' CGAGGACCCCCAGACGGTGGTGT 3' | (SEQ ID NO: 26) |
| | 5' flap1-<u>A</u>CTCGTCGGCGTAG 3' | (SEQ ID NO: 27) |
| IND-C1-WT | 5' CGAGGACCCCCAGACGGTGGTGT 3' | (SEQ ID NO: 26) |
| | 5' flap2-<u>G</u>CTCGTCGGCGT 3' | (SEQ ID NO: 28) |

The invention claimed is:

1. A *Brassica* plant, a cell, part, seed or progeny thereof, wherein the plant, cell, part, seed or progeny comprises at least two partial knockout mutant INDEHISCENT (IND) alleles in its genome,
wherein each of said two partial knockout mutant IND alleles encodes an IND protein wherein:
a Valine in the basic helix-loop-helix (bHLH) domain corresponding to residue 125 of SEQ ID NO: 10 is substituted by a Methionine,
a Glycine in the bHLH domain corresponding to residue 147 of SEQ ID NO: 10 is substituted by a Serine,
an Alanine in the bHLH domain corresponding to residue 160 of SEQ ID NO: 10 is substituted by a Valine,
a Threonine in the bHLH domain corresponding to residue 124 of SEQ ID NO: 10 is substituted by a Methionine, or
an Arginine in the bHLH domain corresponding to residue 130 of SEQ ID NO: 10 is substituted by a Cysteine, and
wherein the two partial knockout mutant IND alleles are partial knockout alleles of IND genes comprising:
(a) a nucleic acid molecule which comprises at least 90% sequence identity to SEQ ID NO: 1, to SEQ ID NO: 3 from the nucleotide at position 46 to the nucleotide at position 633, to SEQ ID NO: 3, to SEQ ID NO: 5, or to SEQ ID NO: 7; or
(b) a nucleic acid molecule encoding an amino acid sequence comprising at least 90% sequence identity to SEQ ID NO: 2, to SEQ ID NO: 4 from the amino acid at position 16 to the amino acid at position 210 or to SEQ ID NO: 4.

2. The plant, cell, part, seed or progeny according to claim 1, wherein each of the two partial knockout mutant IND alleles comprises
the nucleic acid of SEQ ID NO: 1 wherein the G at position 370 is substituted by A, a nucleic acid of SEQ ID NO: 5 wherein the G at position 930 is substituted by A, or a nucleic acid encoding the protein of SEQ ID NO: 2 wherein Valine at position 124 is substituted by Methionine;
the nucleic acid of SEQ ID NO: 1 wherein the G at position 436 is substituted by A, a nucleic acid of SEQ ID NO: 5 wherein the G at position 996 is substituted by A, or a nucleic acid encoding the protein of SEQ ID NO: 2 wherein Glycine at position 146 is substituted by Serine;
the nucleic acid of SEQ ID NO: 1 wherein the C at position 476 is substituted by T, a nucleic acid of SEQ ID NO: 5 wherein the C at position 1036 is substituted by T, or a nucleic acid encoding the protein of SEQ ID NO: 2 wherein Alanine at position 159 is substituted by Valine;
the nucleic acid of SEQ ID NO: 3 wherein the C at position 424 is substituted by T, a nucleic acid of SEQ ID NO: 7 wherein the C at position 920 is substituted by T, or a nucleic acid encoding the protein of SEQ ID NO: 4 wherein Arginine at position 142 is substituted by Cysteine; or
the nucleic acid of SEQ ID NO: 3 wherein the C at position 407 is substituted by T, a nucleic acid of SEQ ID NO: 7 wherein the C at position 903 is substituted by T, or a nucleic acid encoding the protein of SEQ ID NO: 4 wherein Threonine at position 136 is substituted by Methionine.

3. The plant according to claim 1, which further comprises at least one full knockout mutant IND allele in its genome.

4. The plant according to claim 3, wherein the full knockout mutant IND allele is
an IND allele having the sequence of SEQ ID NO: 1 wherein the C at position 364 is substituted with T;
an IND allele having the sequence of SEQ ID NO: 1, wherein the G at positions 307 and 380 are substituted with A;
an IND allele having the sequence of SEQ ID NO: 3 wherein the C at position 148 is substituted with T; or
an IND allele having the sequence of SEQ ID NO: 3 wherein the C at position 403 is substituted with T.

5. The plant according to claim 3, which is homozygous for the partial and/or for the full knockout mutant IND allele.

6. The plant according to claim 1, wherein the plant is *Brassica napus*, *Brassica juncea*, *Brassica carinata*, *Brassica rapa* or *Brassica oleracea*.

7. A plant, or a cell, part, seed or progeny thereof, wherein the plant, cell, part, seed or progeny comprises at least one partial knockout mutant allele of an IND gene in its genome,
wherein said partial knockout mutant IND allele encodes an IND protein wherein:
a Valine in the bHLH domain corresponding to residue 125 of SEQ ID NO: 10 is substituted by a Methionine,
a Glycine in the bHLH domain corresponding to residue 147 of SEQ ID NO: 10 is substituted by a Serine,
an Alanine in the bHLH domain corresponding to residue 160 of SEQ ID NO: 10 is substituted by a Valine,
a Threonine in the bHLH domain corresponding to residue 124 of SEQ ID NO: 10 is substituted by a Methionine, or
an Arginine in the bHLH domain corresponding to residue 130 of SEQ ID NO: 10 is substituted by a Cysteine, and wherein the IND gene comprises:
(a) a nucleic acid molecule which comprises at least 90% sequence identity to SEQ ID NO: 1, to SEQ ID NO: 3 from the nucleotide at position 46 to the nucleotide at position 633, to SEQ ID NO: 3, to SEQ ID NO: 5, or to SEQ ID NO: 7; or
(b) a nucleic acid molecule encoding an amino acid sequence comprising at least 90% sequence identity to SEQ ID NO: 2, to SEQ ID NO: 4 from the amino acid at position 16 to the amino acid at position 210 or to SEQ ID NO: 4.

8. The plant, or cell, part, seed, or progeny thereof according to claim 7, wherein the partial knockout mutant IND allele is
the nucleic acid of SEQ ID NO: 1 wherein the G at position 370 is substituted by A, a nucleic acid of SEQ ID NO: 5 wherein the G at position 930 is substituted by A, or a nucleic acid encoding the protein of SEQ ID NO: 2 wherein Valine at position 124 is substituted by Methionine;
the nucleic acid of SEQ ID NO: 1 wherein the G at position 436 is substituted by A, a nucleic acid of SEQ ID NO: 5 wherein the G at position 996 is substituted by A, or a nucleic acid encoding the protein of SEQ ID NO: 2 wherein Glycine at position 146 is substituted by Serine;
the nucleic acid of SEQ ID NO: 1 wherein the C at position 476 is substituted by T, a nucleic acid of SEQ ID NO: 5 wherein the C at position 1036 is substituted by T, or a nucleic acid encoding the protein of SEQ ID NO: 2 wherein Alanine at position 159 is substituted by Valine;
the nucleic acid of SEQ ID NO: 3 wherein the C at position 424 is substituted by T, a nucleic acid of SEQ ID NO: 7 wherein the C at position 920 is substituted by T, or a nucleic acid encoding the protein of SEQ ID NO: 4 wherein Arginine at position 142 is substituted by Cysteine; or
the nucleic acid of SEQ ID NO: 3 wherein the C at position 407 is substituted by T, a nucleic acid of SEQ ID NO: 7 wherein the C at position 903 is substituted by T, or a nucleic acid encoding the protein of SEQ ID NO: 4 wherein Threonine at position 136 is substituted by Methionine.

9. A seed pod from the plant according to claim 1.

10. A partial knockout mutant allele of an IND gene, wherein said partial knockout mutant IND allele encodes an IND protein wherein:
a Valine in the bHLH domain corresponding to residue 125 of SEQ ID NO: 10 is substituted by a Methionine,
a Glycine in the bHLH domain corresponding to residue 147 of SEQ ID NO: 10 is substituted by a Serine,
an Alanine in the bHLH domain corresponding to residue 160 of SEQ ID NO: 10 is substituted by a Valine,
a Threonine in the bHLH domain corresponding to residue 124 of SEQ ID NO: 10 is substituted by a Methionine, or
an Arginine in the bHLH domain corresponding to residue 130 of SEQ ID NO: 10 is substituted by a Cysteine, and
wherein the IND gene comprises:
(a) a nucleic acid molecule which comprises at least 90% sequence identity to SEQ ID NO: 1, to SEQ ID NO: 3 from the nucleotide at position 46 to the nucleotide at position 633, to SEQ ID NO: 3, to SEQ ID NO: 5, or to SEQ ID NO: 7; or
(b) a nucleic acid molecule encoding an amino acid sequence comprising at least 90% sequence identity to SEQ ID NO: 2, to SEQ ID NO: 4 from the amino acid at position 16 to the amino acid at position 210 or to SEQ ID NO: 4.

11. The mutant allele according to claim 10, which is
the nucleic acid of SEQ ID NO: 1 wherein the G at position 370 is substituted by A, a nucleic acid of SEQ ID NO: 5 wherein the G at position 930 is substituted by A, or a nucleic acid encoding the protein of SEQ ID NO: 2 wherein Valine at position 124 is substituted by Methionine;
the nucleic acid of SEQ ID NO: 1 wherein the G at position 436 is substituted by A, a nucleic acid of SEQ ID NO: 5 wherein the G at position 996 is substituted by A, or a nucleic acid encoding the protein of SEQ ID NO: 2 wherein Glycine at position 146 is substituted by Serine;
the nucleic acid of SEQ ID NO: 1 wherein the C at position 476 is substituted by T, a nucleic acid of SEQ ID NO: 5 wherein the C at position 1036 is substituted by T, or a nucleic acid encoding the protein of SEQ ID NO: 2 wherein Alanine at position 159 is substituted by Valine;
the nucleic acid of SEQ ID NO: 3 wherein the C at position 424 is substituted by T, a nucleic acid of SEQ ID NO: 7 wherein the C at position 920 is substituted by T, or a nucleic acid encoding the protein of SEQ ID NO: 4 wherein Arginine at position 142 is substituted by Cysteine; or
the nucleic acid of SEQ ID NO: 3 wherein the C at position 407 is substituted by T, a nucleic acid of SEQ ID NO: 7 wherein the C at position 903 is substituted by T, or a nucleic acid encoding the protein of SEQ ID NO: 4 wherein Threonine at position 136 is substituted by Methionine.

12. A mutant IND protein encoded by the mutant allele according to claim 10.

13. A plant, or a cell, part, seed or progeny thereof, wherein the plant, cell, part, seed or progeny comprises a partial knockout mutant IND allele,
wherein said allele comprises the nucleic acid of SEQ ID NO: 1 wherein the G at position 370 is substituted by A, a nucleic acid of SEQ ID NO: 5 wherein the G at position 930 is substituted by A, or a nucleic acid encoding the protein of SEQ ID NO: 2 wherein Valine at position 124 is substituted by Methionine, and wherein said plant, cell, part, seed or progeny thereof is produced from a seed comprising said allele; reference seed comprising said allele having been deposited at the NCIMB under accession number NCIMB 41570;
wherein said allele comprises the nucleic acid of SEQ ID NO: 1 wherein the G at position 436 is substituted by A, a nucleic acid of SEQ ID NO: 5 wherein the G at position 996 is substituted by A, or a nucleic acid encoding the protein of SEQ ID NO: 2 wherein Glycine at position 146 is substituted by Serine; and wherein said plant, cell, part, seed or progeny thereof is produced from a seed comprising said allele; reference seed comprising said allele having been deposited at the NCIMB under accession number NCIMB 41571;
wherein said allele comprises the nucleic acid of SEQ ID NO: 1 wherein the C at position 476 is substituted by T, a nucleic acid of SEQ ID NO: 5 wherein the C at position 1036 is substituted by T, or a nucleic acid encoding the protein of SEQ ID NO: 2 wherein Alanine at position 159 is substituted by Valine; and wherein said plant, cell, part, seed or progeny thereof is produced from a seed comprising said allele; reference seed comprising said allele having been deposited at the NCIMB under accession number NCIMB 41572; wherein said allele comprises the nucleic acid of SEQ ID NO: 3 wherein the C at position 424 is substituted by T, a nucleic acid of SEQ ID NO: 7 wherein the C at position 920 is substituted by T, or a nucleic acid encoding the protein of SEQ ID NO: 4 wherein Arginine at position 142 is substituted by Cysteine; and wherein said plant, cell, part, seed or progeny thereof is produced from a seed comprising said allele; reference seed comprising said allele having been deposited at the NCIMB under accession number NCIMB 41575, or wherein said allele comprises the nucleic acid of SEQ ID NO: 3 wherein the C at position 407 is substituted by T, a nucleic acid of SEQ ID NO: 7 wherein the C at position 903 is substituted by T, or a nucleic acid encoding the protein of SEQ ID NO: 4 wherein Threonine at position 136 is substituted by Methionine, and wherein said plant, cell, part, seed or progeny thereof is produced from a seed comprising said allele; reference seed comprising said allele having been deposited at the NCIMB under accession number NCIMB 41573.

14. A method of increasing seed yield in a *Brassica* plant comprising introducing the mutant IND allele according to claim 10 into the *Brassica* plant.

15. A method of increasing shatter resistance in a *Brassica* plant comprising introducing the mutant IND allele according to claim 10 into the *Brassica* plant.

16. The plant according to claim 1, comprising two partial knockout mutant IND alleles as set forth in claim 1 which are different from one another.

17. The plant according to claim 1, comprising two partial knockout mutant IND alleles as set forth in claim 1 which are different from one another and which are partial knockout mutant IND alleles of the same IND gene.

18. The plant according to claim 1, comprising two partial knockout mutant IND alleles as set forth in claim 1, wherein the plant is homozygous for said two partial knockout mutant IND alleles.

* * * * *

SEQUENCE LISTING

<160> NUMBER OF SEQ ID NOS: 28

<210> SEQ ID NO 1
<211> LENGTH: 558
<212> TYPE: DNA
<213> ORGANISM: Brassica napus
<220> FEATURE:
<221> NAME/KEY: CDS
<222> LOCATION: (1)..(555)

<400> SEQUENCE: 1

```
atg tct ggc tca aaa gca gat gca gcc ata gcc cca ata gtc atg atg        48
Met Ser Gly Ser Lys Ala Asp Ala Ala Ile Ala Pro Ile Val Met Met
1               5                   10                  15 gag cat cat cat ctc ctt atg aat tgg aac aaa cct att gat ctc att        96
Glu His His His Leu Leu Met Asn Trp Asn Lys Pro Ile Asp Leu Ile
            20                  25                  30 aca gaa gaa aac tct ttt aac cac aat cct cat ttc ata gta gat cca       144
Thr Glu Glu Asn Ser Phe Asn His Asn Pro His Phe Ile Val Asp Pro
        35                  40                  45 cct tcc gaa acc cta agc cac ttc cag ccc ccg ccg aca atc ttc tcc       192
Pro Ser Glu Thr Leu Ser His Phe Gln Pro Pro Pro Thr Ile Phe Ser
    50                  55                  60 gat cac gga gga gga gag gaa gca gaa gaa gaa gaa gaa gaa gaa gga       240
Asp His Gly Gly Gly Glu Glu Ala Glu Glu Glu Glu Glu Glu Glu Gly
65                  70                  75                  80 gag gaa gag atg gat ccg atg aag aag atg caa tac gcg att gct gcc       288
Glu Glu Glu Met Asp Pro Met Lys Lys Met Gln Tyr Ala Ile Ala Ala
```

```
Glu Glu Glu Met Asp Pro Met Lys Lys Met Gln Tyr Ala Ile Ala Ala
                85                  90                  95 atg cag ccc gta gac ctc gat cca gcc acc gtt cct aag ccg aac cgc      336
Met Gln Pro Val Asp Leu Asp Pro Ala Thr Val Pro Lys Pro Asn Arg
            100                 105                 110 cgt aac gta agg gta agc gac gac cct cag acg gtg gtg gct cgt cgg      384
Arg Asn Val Arg Val Ser Asp Asp Pro Gln Thr Val Val Ala Arg Arg
        115                 120                 125 cgt aga gaa agg ata agc gag aag atc cgg ata ttg aag agg atg gtg      432
Arg Arg Glu Arg Ile Ser Glu Lys Ile Arg Ile Leu Lys Arg Met Val
    130                 135                 140 cca ggt gca aag atg gac act gcc tcc atg ctc gac gaa gcc atc          480
Pro Gly Gly Ala Lys Met Asp Thr Ala Ser Met Leu Asp Glu Ala Ile
145                 150                 155                 160 cgc tac acc aag ttc ttg aaa cgg cag gtg agg cta gct tct tca gcc      528
Arg Tyr Thr Lys Phe Leu Lys Arg Gln Val Arg Leu Ala Ser Ser Ala
                165                 170                 175 tca cac tca gct tgg agc tcc tat gtc tga                              558
Ser His Ser Ala Trp Ser Ser Tyr Val
            180                 185
```

<210> SEQ ID NO 2
<211> LENGTH: 185
<212> TYPE: PRT
<213> ORGANISM: Brassica napus

<400> SEQUENCE: 2

```
Met Ser Gly Ser Lys Ala Asp Ala Ala Ile Ala Pro Ile Val Met Met
1               5                   10                  15

Glu His His Leu Leu Met Asn Trp Asn Lys Pro Ile Asp Leu Ile
            20                  25                  30

Thr Glu Asn Ser Phe Asn His Asn Pro His Phe Ile Val Asp Pro
        35                  40                  45

Pro Ser Glu Thr Leu Ser His Phe Gln Pro Pro Thr Ile Phe Ser
    50                  55                  60

Asp His Gly Gly Gly Glu Ala Glu Glu Glu Glu Glu Glu Gly
65                  70                  75                  80

Glu Glu Glu Met Asp Pro Met Lys Lys Met Gln Tyr Ala Ile Ala Ala
                85                  90                  95

Met Gln Pro Val Asp Leu Asp Pro Ala Thr Val Pro Lys Pro Asn Arg
            100                 105                 110

Arg Asn Val Arg Val Ser Asp Asp Pro Gln Thr Val Val Ala Arg Arg
        115                 120                 125

Arg Arg Glu Arg Ile Ser Glu Lys Ile Arg Ile Leu Lys Arg Met Val
    130                 135                 140

Pro Gly Gly Ala Lys Met Asp Thr Ala Ser Met Leu Asp Glu Ala Ile
145                 150                 155                 160

Arg Tyr Thr Lys Phe Leu Lys Arg Gln Val Arg Leu Ala Ser Ser Ala
                165                 170                 175

Ser His Ser Ala Trp Ser Ser Tyr Val
            180                 185
```

<210> SEQ ID NO 3
<211> LENGTH: 633
<212> TYPE: DNA
<213> ORGANISM: Brassica napus
<220> FEATURE:
<221> NAME/KEY: CDS
<222> LOCATION: (1)..(630)

```
<400> SEQUENCE: 3 atg tat aaa aga aag gtc tat gcg tct cta gtc caa aaa ctc tat atg    48
Met Tyr Lys Arg Lys Val Tyr Ala Ser Leu Val Gln Lys Leu Tyr Met
1               5                   10                  15 tct ggt tca aaa gca gat gca gca gcc ata gcc cca ata gtc atg atg    96
Ser Gly Ser Lys Ala Asp Ala Ala Ala Ile Ala Pro Ile Val Met Met
            20                  25                  30 gag cct cat cat ctc ctt atg aac tgg aac aaa cct att gat ctc att   144
Glu Pro His His Leu Leu Met Asn Trp Asn Lys Pro Ile Asp Leu Ile
        35                  40                  45 aca caa gaa aac tct ttt aac cac aat cct cat ttc atg gta gat cca   192
Thr Gln Glu Asn Ser Phe Asn His Asn Pro His Phe Met Val Asp Pro
    50                  55                  60 cct tcc gaa acc cta agc cac ttc cag ccc ccg ccg aca gtc ttc tcc   240
Pro Ser Glu Thr Leu Ser His Phe Gln Pro Pro Pro Thr Val Phe Ser
65                  70                  75                  80 gat ccc gga gga gga gag gaa gca gaa gac gaa gaa gga gag gaa gag   288
Asp Pro Gly Gly Gly Glu Glu Ala Glu Asp Glu Glu Gly Glu Glu Glu
                85                  90                  95 ata gat gag atg aag gag atg caa tac gcg att gct gcc atg cag ccc   336
Ile Asp Glu Met Lys Glu Met Gln Tyr Ala Ile Ala Ala Met Gln Pro
            100                 105                 110 gta gac atc gat cca gcc acc gtt cct aag ccg aac cgc cgt aac gta   384
Val Asp Ile Asp Pro Ala Thr Val Pro Lys Pro Asn Arg Arg Asn Val
        115                 120                 125 agg gta agc gag gac ccc cag acg gtg gtg gct cgt cgg cgt aga gaa   432
Arg Val Ser Glu Asp Pro Gln Thr Val Val Ala Arg Arg Arg Arg Glu
    130                 135                 140 agg ata agc gag aag atc cgg ata ttg aag agg atg gtg cca ggc ggt   480
Arg Ile Ser Glu Lys Ile Arg Ile Leu Lys Arg Met Val Pro Gly Gly
145                 150                 155                 160 gca aag atg gac act gcc tcc atg ctt gac gaa gcc atc cgc tac acc   528
Ala Lys Met Asp Thr Ala Ser Met Leu Asp Glu Ala Ile Arg Tyr Thr
                165                 170                 175 aag ttc ttg aaa cgg cag gtg agg ctt ctt cag cct cac act cag ctt   576
Lys Phe Leu Lys Arg Gln Val Arg Leu Leu Gln Pro His Thr Gln Leu
            180                 185                 190 ggg gct cct atg tct gac cct tct cgc ctt tgt tat tac cac aac tcg   624
Gly Ala Pro Met Ser Asp Pro Ser Arg Leu Cys Tyr Tyr His Asn Ser
        195                 200                 205 gat acc taa                                                        633
Asp Thr
    210

<210> SEQ ID NO 4
<211> LENGTH: 210
<212> TYPE: PRT
<213> ORGANISM: Brassica napus

<400> SEQUENCE: 4

Met Tyr Lys Arg Lys Val Tyr Ala Ser Leu Val Gln Lys Leu Tyr Met
1               5                   10                  15

Ser Gly Ser Lys Ala Asp Ala Ala Ala Ile Ala Pro Ile Val Met Met
            20                  25                  30

Glu Pro His His Leu Leu Met Asn Trp Asn Lys Pro Ile Asp Leu Ile
        35                  40                  45

Thr Gln Glu Asn Ser Phe Asn His Asn Pro His Phe Met Val Asp Pro
    50                  55                  60
```

```
Pro Ser Glu Thr Leu Ser His Phe Gln Pro Pro Thr Val Phe Ser
 65                  70                  75                  80

Asp Pro Gly Gly Gly Glu Glu Ala Glu Asp Glu Glu Gly Glu Glu
                 85                  90                  95

Ile Asp Glu Met Lys Glu Met Gln Tyr Ala Ile Ala Ala Met Gln Pro
            100                 105                 110

Val Asp Ile Asp Pro Ala Thr Val Pro Lys Pro Asn Arg Arg Asn Val
        115                 120                 125

Arg Val Ser Glu Asp Pro Gln Thr Val Val Ala Arg Arg Arg Glu
    130                 135                 140

Arg Ile Ser Glu Lys Ile Arg Ile Leu Lys Arg Met Val Pro Gly Gly
145                 150                 155                 160

Ala Lys Met Asp Thr Ala Ser Met Leu Asp Glu Ala Ile Arg Tyr Thr
                165                 170                 175

Lys Phe Leu Lys Arg Gln Val Arg Leu Leu Gln Pro His Thr Gln Leu
            180                 185                 190

Gly Ala Pro Met Ser Asp Pro Ser Arg Leu Cys Tyr Tyr His Asn Ser
        195                 200                 205

Asp Thr
    210
```

<210> SEQ ID NO 5
<211> LENGTH: 1622
<212> TYPE: DNA
<213> ORGANISM: Brassica napus
<220> FEATURE:
<221> NAME/KEY: CDS
<222> LOCATION: (561)..(1118)

<400> SEQUENCE: 5

```
tttgacaatc tacatacata accaacaaaa agtagaatac cttgaaaatc taaaacccaa        60
aatatgatgt aaaactcaag cttggtccag agcataaaaa aattaaagcc atcgctttgg       120
tatcacatat ttaaacgtca gttttttttt tttttttggg ggggggggg ggggtaatat        180 aaaaatataa ttaacaaaaa aaaattatga acaattagc atgtaaaaca ctaatctttt        240
ggttgtgaca aaacgttttc acaaatgttc tataaataaa ttcaagtgca ttttatctgc       300
aaaatatata ctttcactca taaaataaga gcgtttaaaa cattcataca cgcactacat       360
tgacatgaca aaagaaatcc gcaaatacac atgatgtatg tcgaaaaaaa caaaaaatac       420
acatgatgta tatatagaga ggatagtatc taggaaataa gactatatta tatatataaa       480
gaaaatagag aaaagataaa aatataaatt ggtatgtata aagagaaggt ctatgcgtct       540
ctagtccaaa aactctatat atg tct ggc tca aaa gca gat gca gcc ata gcc       593
                        Met Ser Gly Ser Lys Ala Asp Ala Ala Ile Ala
                         1               5                  10 cca ata gtc atg atg gag cat cat cat ctc ctt atg aat tgg aac aaa       641
Pro Ile Val Met Met Glu His His His Leu Leu Met Asn Trp Asn Lys
             15                  20                  25 cct att gat ctc att aca gaa gaa aac tct ttt aac cac aat cct cat       689
Pro Ile Asp Leu Ile Thr Glu Glu Asn Ser Phe Asn His Asn Pro His
         30                  35                  40 ttc ata gta gat cca cct tcc gaa acc cta agc cac ttc cag ccc ccg       737
Phe Ile Val Asp Pro Pro Ser Glu Thr Leu Ser His Phe Gln Pro Pro
     45                  50                  55 ccg aca atc ttc tcc gat cac gga gga gga gag gaa gca gaa gaa gaa       785
Pro Thr Ile Phe Ser Asp His Gly Gly Gly Glu Glu Ala Glu Glu Glu
 60                  65                  70                  75
```

| | | | | | | | | | | | | | | | | |
|---|---|---|---|---|---|---|---|---|---|---|---|---|---|---|---|---|
| gaa | gaa | gaa | gaa | gga | gag | gaa | gag | atg | gat | ccg | atg | aag | aag | atg | caa | 833 |
| Glu | Glu | Glu | Glu | Gly | Glu | Glu | Glu | Met | Asp | Pro | Met | Lys | Lys | Met | Gln | |
| | | | 80 | | | | | 85 | | | | | 90 | | | |
| tac | gcg | att | gct | gcc | atg | cag | ccc | gta | gac | ctc | gat | cca | gcc | acc | gtt | 881 |
| Tyr | Ala | Ile | Ala | Ala | Met | Gln | Pro | Val | Asp | Leu | Asp | Pro | Ala | Thr | Val | |
| | | 95 | | | | | 100 | | | | | 105 | | | | |
| cct | aag | ccg | aac | cgc | cgt | aac | gta | agg | gta | agc | gac | gac | cct | cag | acg | 929 |
| Pro | Lys | Pro | Asn | Arg | Arg | Asn | Val | Arg | Val | Ser | Asp | Asp | Pro | Gln | Thr | |
| | 110 | | | | | 115 | | | | | 120 | | | | | |
| gtg | gtg | gct | cgt | cgg | cgt | aga | gaa | agg | ata | agc | gag | aag | atc | cgg | ata | 977 |
| Val | Val | Ala | Arg | Arg | Arg | Arg | Glu | Arg | Ile | Ser | Glu | Lys | Ile | Arg | Ile | |
| 125 | | | | | 130 | | | | | 135 | | | | | | |
| ttg | aag | agg | atg | gtg | cca | ggc | ggt | gca | aag | atg | gac | act | gcc | tcc | atg | 1025 |
| Leu | Lys | Arg | Met | Val | Pro | Gly | Gly | Ala | Lys | Met | Asp | Thr | Ala | Ser | Met | |
| 140 | | | | 145 | | | | | 150 | | | | | 155 | | |
| ctc | gac | gaa | gcc | atc | cgc | tac | acc | aag | ttc | ttg | aaa | cgg | cag | gtg | agg | 1073 |
| Leu | Asp | Glu | Ala | Ile | Arg | Tyr | Thr | Lys | Phe | Leu | Lys | Arg | Gln | Val | Arg | |
| | | | | 160 | | | | | 165 | | | | | 170 | | |
| cta | gct | tct | tca | gcc | tca | cac | tca | gct | tgg | agc | tcc | tat | gtc | tga | | 1118 |
| Leu | Ala | Ser | Ser | Ala | Ser | His | Ser | Ala | Trp | Ser | Ser | Tyr | Val | | | |
| | | 175 | | | | | 180 | | | | | 185 | | | | |

| | | |
|---|---|---|
| cccttcttgc ctttgttatt accacaactc ggatacctaa ttataattct atcacgcgtt | | 1178 |
| tcatgttgat atatatagat aaatggtcga ataaggattt cgatcgaaga ttgtatgtac | | 1238 |
| aataaatgat gtgtgtattt caattaatgt atgatatata tatatatatg tatgcagtat | | 1298 |
| gcatttatat tctattctct ataaggaggc aacattgccg gattagggct tgatcttat | | 1358 |
| gcaagttttc cgaccaaaaa tatgaaatac ttgtttggat ataacatatg aatcggataa | | 1418 |
| gtgttactag ttatataact ggaaaacaaa tgtctggaat aagaattccc gggagaacca | | 1478 |
| agcctttctc taatccctaa gattatagct actgaaacaa tgaaacaatg aagaatcagt | | 1538 |
| tgggcattag taaaaaaaaa agaatcagtt gggttgctta taaaattttg ttataaaatt | | 1598 |
| tatgtcgtat gtgtgttagc cgta | | 1622 |

<210> SEQ ID NO 6
<211> LENGTH: 185
<212> TYPE: PRT
<213> ORGANISM: Brassica napus

<400> SEQUENCE: 6

Met Ser Gly Ser Lys Ala Asp Ala Ala Ile Ala Pro Ile Val Met Met
1               5                   10                  15

Glu His His His Leu Leu Met Asn Trp Asn Lys Pro Ile Asp Leu Ile
                20                  25                  30

Thr Glu Glu Asn Ser Phe Asn His Asn Pro His Phe Ile Val Asp Pro
            35                  40                  45

Pro Ser Glu Thr Leu Ser His Phe Gln Pro Pro Thr Ile Phe Ser
        50                  55                  60

Asp His Gly Gly Gly Glu Glu Ala Glu Glu Glu Glu Glu Glu Glu Gly
65                  70                  75                  80

Glu Glu Glu Met Asp Pro Met Lys Lys Met Gln Tyr Ala Ile Ala Ala
                85                  90                  95

Met Gln Pro Val Asp Leu Asp Pro Ala Thr Val Pro Lys Pro Asn Arg
            100                 105                 110

Arg Asn Val Arg Val Ser Asp Asp Pro Gln Thr Val Val Ala Arg Arg
        115                 120                 125

Arg Arg Glu Arg Ile Ser Glu Lys Ile Arg Ile Leu Lys Arg Met Val

```
                      130                 135                 140
Pro Gly Gly Ala Lys Met Asp Thr Ala Ser Met Leu Asp Glu Ala Ile
145                 150                 155                 160

Arg Tyr Thr Lys Phe Leu Lys Arg Gln Val Arg Leu Ala Ser Ser Ala
                165                 170                 175

Ser His Ser Ala Trp Ser Ser Tyr Val
            180                 185

<210> SEQ ID NO 7
<211> LENGTH: 1593
<212> TYPE: DNA
<213> ORGANISM: Brassica napus
<220> FEATURE:
<221> NAME/KEY: CDS
<222> LOCATION: (497)..(1126)

<400> SEQUENCE: 7
tgccatacat aaccacggat catagtcgac acctcaacgt gaagcaaatt tgacaatcta      60
catacataac caacaaaaag tagaataccg tgaaaaccta aacccaaaat atgatgtaaa     120
actcaagctt ggtccagagc ataaaaaaat taaagccatc gctttggtat cacatattta     180
aacgtcagtt ttttttttggg gaagtaatat aaaaatataa ttaacaagaa aatttatgaa    240
ataattagca tgtaaaacac tagtcttttg gttgtgacaa aacgttttca caaatgttct     300
ataaataaat tcaagcacat tttatctgca aaatatatac tttcactcat aaaataagag     360
cgtttaaaac attcatatac gcactacatt gacatgacaa agaaatccg caaatacaaa      420 catatttagt tcggatatat ctaggaaata agactatatt atatatataa agaaattaga     480 aaaaagaaa attggt atg tat aaa aga aag gtc tat gcg tct cta gtc caa    532
                 Met Tyr Lys Arg Lys Val Tyr Ala Ser Leu Val Gln
                  1               5                   10 aaa ctc tat atg tct ggt tca aaa gca gat gca gca gcc ata gcc cca    580
Lys Leu Tyr Met Ser Gly Ser Lys Ala Asp Ala Ala Ala Ile Ala Pro
        15                  20                  25 ata gtc atg atg gag cct cat cat ctc ctt atg aac tgg aac aaa cct    628
Ile Val Met Met Glu Pro His His Leu Leu Met Asn Trp Asn Lys Pro
 30                  35                  40 att gat ctc att aca caa gaa aac tct ttt aac cac aat cct cat ttc    676
Ile Asp Leu Ile Thr Gln Glu Asn Ser Phe Asn His Asn Pro His Phe
 45                  50                  55                  60 atg gta gat cca cct tcc gaa acc cta agc cac ttc cag ccc ccg ccg    724
Met Val Asp Pro Pro Ser Glu Thr Leu Ser His Phe Gln Pro Pro Pro
                 65                  70                  75 aca gtc ttc tcc gat ccc gga gga gga gag gaa gca gaa gac gaa gaa    772
Thr Val Phe Ser Asp Pro Gly Gly Gly Glu Glu Ala Glu Asp Glu Glu
         80                  85                  90 gga gag gaa gag ata gat gag atg aag gag atg caa tac gcg att gct    820
Gly Glu Glu Glu Ile Asp Glu Met Lys Glu Met Gln Tyr Ala Ile Ala
             95                 100                 105 gcc atg cag ccc gta gac atc gat cca gcc acc gtt cct aag ccg aac    868
Ala Met Gln Pro Val Asp Ile Asp Pro Ala Thr Val Pro Lys Pro Asn
110                 115                 120 cgc cgt aac gta agg gta agc gag gac ccc cag acg gtg gtg gct cgt    916
Arg Arg Asn Val Arg Val Ser Glu Asp Pro Gln Thr Val Val Ala Arg
125                 130                 135                 140 cgg cgt aga gaa agg ata agc gag aag atc cgg ata ttg aag agg atg    964
Arg Arg Arg Glu Arg Ile Ser Glu Lys Ile Arg Ile Leu Lys Arg Met
                145                 150                 155 gtg cca ggc ggt gca aag atg gac act gcc tcc atg ctt gac gaa gcc   1012
```

```
Val Pro Gly Gly Ala Lys Met Asp Thr Ala Ser Met Leu Asp Glu Ala
            160                 165                 170 atc cgc tac acc aag ttc ttg aaa cgg cag gtg agg ctt ctt cag cct    1060
Ile Arg Tyr Thr Lys Phe Leu Lys Arg Gln Val Arg Leu Leu Gln Pro
        175                 180                 185 cac act cag ctt ggg gct cct atg tct gac cct tct cgc ctt tgt tat    1108
His Thr Gln Leu Gly Ala Pro Met Ser Asp Pro Ser Arg Leu Cys Tyr
190                 195                 200 tac cac aac tcg gat acc taattataat tctatcacgc gtttcatgtt           1156
Tyr His Asn Ser Asp Thr
205                 210 gatatatata gataaatggt tgaataagga tttcgatcga agattgtatg gctattgatt  1216
acattatata ttgtacaata aatgatgtgt gtatttctat taatgtatat atgatatata  1276
tctgtttgca gtatgcattt atattctatt ctttataggg aggcaacatg ccggattagg  1336
gctttgatcg tatgcaagtt ttccgaccaa aaatatgaaa tacttgtttg gatataacat  1396
atgaatcgga taagtgttac tagttatata actggaaaaa attgtttggt ataagaattc  1456
ccgggagaac caagcctttc tctaatccct aagatcatag ctactgaaat aatgaaaaaa  1516
aacaaaaaaa aaacaatgaa gaatcagttg ggcattagtc caaaaaaaaa aaagaatcag  1576
ttggattgct tataaaa                                                 1593

<210> SEQ ID NO 8
<211> LENGTH: 210
<212> TYPE: PRT
<213> ORGANISM: Brassica napus

<400> SEQUENCE: 8

Met Tyr Lys Arg Lys Val Tyr Ala Ser Leu Val Gln Lys Leu Tyr Met
1               5                   10                  15

Ser Gly Ser Lys Ala Asp Ala Ala Ile Ala Pro Ile Val Met Met
            20                  25                  30

Glu Pro His His Leu Leu Met Asn Trp Asn Lys Pro Ile Asp Leu Ile
        35                  40                  45

Thr Gln Glu Asn Ser Phe Asn His Asn Pro His Phe Met Val Asp Pro
    50                  55                  60

Pro Ser Glu Thr Leu Ser His Phe Gln Pro Pro Thr Val Phe Ser
65              70                  75                  80

Asp Pro Gly Gly Gly Glu Ala Glu Asp Glu Gly Glu Glu
            85                  90                  95

Ile Asp Glu Met Lys Glu Met Gln Tyr Ala Ile Ala Ala Met Gln Pro
        100                 105                 110

Val Asp Ile Asp Pro Ala Thr Val Pro Lys Pro Asn Arg Arg Asn Val
    115                 120                 125

Arg Val Ser Glu Asp Pro Gln Thr Val Val Ala Arg Arg Arg Glu
130                 135                 140

Arg Ile Ser Glu Lys Ile Arg Ile Leu Lys Arg Met Val Pro Gly Gly
145                 150                 155                 160

Ala Lys Met Asp Thr Ala Ser Met Leu Asp Glu Ala Ile Arg Tyr Thr
                165                 170                 175

Lys Phe Leu Lys Arg Gln Val Arg Leu Leu Gln Pro His Thr Gln Leu
            180                 185                 190

Gly Ala Pro Met Ser Asp Pro Ser Arg Leu Cys Tyr Tyr His Asn Ser
        195                 200                 205

Asp Thr
```

<210> SEQ ID NO 9
<211> LENGTH: 597
<212> TYPE: DNA
<213> ORGANISM: Arabidopsis thaliana
<220> FEATURE:
<221> NAME/KEY: CDS
<222> LOCATION: (1)..(594)

<400> SEQUENCE: 9

| | | | | | | | | | | | | | | | | |
|---|---|---|---|---|---|---|---|---|---|---|---|---|---|---|---|---|
| atg | aat | ggt | atg | tat | aaa | aag | aaa | gga | gtg | tgc | gac | tct | tgt | gtc | | 48 |
| Met | Glu | Asn | Gly | Met | Tyr | Lys | Lys | Lys | Gly | Val | Cys | Asp | Ser | Cys | Val | |
| 1 | | | | 5 | | | | | 10 | | | | | 15 | | |
| tcg | tcc | aaa | agc | aga | tcc | aac | cac | agc | ccc | aaa | aga | agc | atg | atg | gag | 96 |
| Ser | Ser | Lys | Ser | Arg | Ser | Asn | His | Ser | Pro | Lys | Arg | Ser | Met | Met | Glu | |
| | | | 20 | | | | | 25 | | | | | 30 | | | |
| cct | cag | cct | cac | cat | ctc | ctc | atg | gat | tgg | aac | aaa | gct | aat | gat | ctt | 144 |
| Pro | Gln | Pro | His | His | Leu | Leu | Met | Asp | Trp | Asn | Lys | Ala | Asn | Asp | Leu | |
| | | 35 | | | | | 40 | | | | | 45 | | | | |
| ctc | aca | caa | gaa | cac | gca | gct | ttt | ctc | aat | gat | cct | cac | cat | ctc | atg | 192 |
| Leu | Thr | Gln | Glu | His | Ala | Ala | Phe | Leu | Asn | Asp | Pro | His | His | Leu | Met | |
| 50 | | | | | 55 | | | | | 60 | | | | | | |
| tta | gat | cca | cct | ccc | gaa | acc | cta | att | cac | ttg | gac | gaa | gac | gaa | gag | 240 |
| Leu | Asp | Pro | Pro | Pro | Glu | Thr | Leu | Ile | His | Leu | Asp | Glu | Asp | Glu | Glu | |
| 65 | | | | | 70 | | | | | 75 | | | | | 80 | |
| tac | gat | gaa | gac | atg | gat | gcg | atg | aag | gag | atg | cag | tac | atg | atc | gcc | 288 |
| Tyr | Asp | Glu | Asp | Met | Asp | Ala | Met | Lys | Glu | Met | Gln | Tyr | Met | Ile | Ala | |
| | | | | 85 | | | | | 90 | | | | | 95 | | |
| gtc | atg | cag | ccc | gta | gac | atc | gac | cct | gcc | acg | gtc | cct | aag | ccg | aac | 336 |
| Val | Met | Gln | Pro | Val | Asp | Ile | Asp | Pro | Ala | Thr | Val | Pro | Lys | Pro | Asn | |
| | | | 100 | | | | | 105 | | | | | 110 | | | |
| cgc | cgt | aac | gta | agg | ata | agc | gac | gat | cct | cag | acg | gtg | gtt | gct | cgt | 384 |
| Arg | Arg | Asn | Val | Arg | Ile | Ser | Asp | Asp | Pro | Gln | Thr | Val | Val | Ala | Arg | |
| | | 115 | | | | | 120 | | | | | 125 | | | | |
| cgg | cgt | cgg | gaa | agg | atc | agc | gag | aag | atc | cga | att | ctc | aag | agg | atc | 432 |
| Arg | Arg | Arg | Glu | Arg | Ile | Ser | Glu | Lys | Ile | Arg | Ile | Leu | Lys | Arg | Ile | |
| 130 | | | | | 135 | | | | | 140 | | | | | | |
| gtg | cct | ggt | ggt | gcg | aag | atg | gac | aca | gct | tcc | atg | ctc | gac | gaa | gcc | 480 |
| Val | Pro | Gly | Gly | Ala | Lys | Met | Asp | Thr | Ala | Ser | Met | Leu | Asp | Glu | Ala | |
| 145 | | | | | 150 | | | | | 155 | | | | | 160 | |
| ata | cgt | tac | acc | aag | ttc | ttg | aaa | cgg | cag | gtg | agg | att | ctt | cag | cct | 528 |
| Ile | Arg | Tyr | Thr | Lys | Phe | Leu | Lys | Arg | Gln | Val | Arg | Ile | Leu | Gln | Pro | |
| | | | | 165 | | | | | 170 | | | | | 175 | | |
| cac | tct | cag | att | gga | gct | cct | atg | gct | aac | ccc | tct | tac | ctt | tgt | tat | 576 |
| His | Ser | Gln | Ile | Gly | Ala | Pro | Met | Ala | Asn | Pro | Ser | Tyr | Leu | Cys | Tyr | |
| | | | 180 | | | | | 185 | | | | | 190 | | | |
| tac | cac | aac | tcc | caa | ccc | tga | | | | | | | | | | 597 |
| Tyr | His | Asn | Ser | Gln | Pro | | | | | | | | | | | |
| | | | | 195 | | | | | | | | | | | | |

<210> SEQ ID NO 10
<211> LENGTH: 198
<212> TYPE: PRT
<213> ORGANISM: Arabidopsis thaliana

<400> SEQUENCE: 10

| | | | | | | | | | | | | | | | |
|---|---|---|---|---|---|---|---|---|---|---|---|---|---|---|---|
| Met | Glu | Asn | Gly | Met | Tyr | Lys | Lys | Lys | Gly | Val | Cys | Asp | Ser | Cys | Val |
| 1 | | | | 5 | | | | | 10 | | | | | 15 | |
| Ser | Ser | Lys | Ser | Arg | Ser | Asn | His | Ser | Pro | Lys | Arg | Ser | Met | Met | Glu |
| | | | 20 | | | | | 25 | | | | | 30 | | |

```
Pro Gln Pro His His Leu Leu Met Asp Trp Asn Lys Ala Asn Asp Leu
         35                  40                  45

Leu Thr Gln Glu His Ala Ala Phe Leu Asn Asp Pro His His Leu Met
 50                  55                  60

Leu Asp Pro Pro Pro Glu Thr Leu Ile His Leu Asp Glu Asp Glu Glu
 65                  70                  75                  80

Tyr Asp Glu Asp Met Asp Ala Met Lys Glu Met Gln Tyr Met Ile Ala
                 85                  90                  95

Val Met Gln Pro Val Asp Ile Asp Pro Ala Thr Val Pro Lys Pro Asn
             100                 105                 110

Arg Arg Asn Val Arg Ile Ser Asp Asp Pro Gln Thr Val Val Ala Arg
             115                 120                 125

Arg Arg Arg Glu Arg Ile Ser Glu Lys Ile Arg Ile Leu Lys Arg Ile
 130                 135                 140

Val Pro Gly Gly Ala Lys Met Asp Thr Ala Ser Met Leu Asp Glu Ala
 145                 150                 155                 160

Ile Arg Tyr Thr Lys Phe Leu Lys Arg Gln Val Arg Ile Leu Gln Pro
                 165                 170                 175

His Ser Gln Ile Gly Ala Pro Met Ala Asn Pro Ser Tyr Leu Cys Tyr
             180                 185                 190

Tyr His Asn Ser Gln Pro
             195
```

```
<210> SEQ ID NO 11
<211> LENGTH: 29
<212> TYPE: DNA
<213> ORGANISM: Artificial
<220> FEATURE:
<223> OTHER INFORMATION: oligonucleotide for detection of IND-A1-EMS06
      and -WT

<400> SEQUENCE: 11
cgtaagggta agcgacgacc ctcagacgt                                        29

<210> SEQ ID NO 12
<211> LENGTH: 14
<212> TYPE: DNA
<213> ORGANISM: Artificial
<220> FEATURE:
<223> OTHER INFORMATION: oligonucleotide for detection of IND-A1-EMS06

<400> SEQUENCE: 12
atggtggctc gtcg                                                        14

<210> SEQ ID NO 13
<211> LENGTH: 13
<212> TYPE: DNA
<213> ORGANISM: Artificial
<220> FEATURE:
<223> OTHER INFORMATION: oligonucleotide for detection of IND-A1-WT

<400> SEQUENCE: 13
gtggtggctc gtc                                                         13

<210> SEQ ID NO 14
<211> LENGTH: 27
<212> TYPE: DNA
<213> ORGANISM: Artificial
<220> FEATURE:
<223> OTHER INFORMATION: oligonucleotide for detection of IND-A1-EMS09
      and -WT
```

<400> SEQUENCE: 14
ggaggcagtg tccatctttg caccgca        27

<210> SEQ ID NO 15
<211> LENGTH: 15
<212> TYPE: DNA
<213> ORGANISM: Artificial
<220> FEATURE:
<223> OTHER INFORMATION: oligonucleotide for detection of IND-A1-EMS09

<400> SEQUENCE: 15
ttggcaccat cctct        15

<210> SEQ ID NO 16
<211> LENGTH: 15
<212> TYPE: DNA
<213> ORGANISM: Artificial
<220> FEATURE:
<223> OTHER INFORMATION: oligonucleotide for detection of IND-A1-WT

<400> SEQUENCE: 16
ctggcaccat cctct        15

<210> SEQ ID NO 17
<211> LENGTH: 33
<212> TYPE: DNA
<213> ORGANISM: Artificial
<220> FEATURE:
<223> OTHER INFORMATION: oligonucleotide for detection of IND-A1-EMS13
      and -WT

<400> SEQUENCE: 17
cctgccgttt caagaacttg gtgtagcgga tgt        33

<210> SEQ ID NO 18
<211> LENGTH: 15
<212> TYPE: DNA
<213> ORGANISM: Artificial
<220> FEATURE:
<223> OTHER INFORMATION: oligonucleotide for detection of IND-A1-EMS13

<400> SEQUENCE: 18
acttcgtcga gcatg        15

<210> SEQ ID NO 19
<211> LENGTH: 15
<212> TYPE: DNA
<213> ORGANISM: Artificial
<220> FEATURE:
<223> OTHER INFORMATION: oligonucleotide for detection of IND-A1-WT

<400> SEQUENCE: 19
gcttcgtcga gcatg        15

<210> SEQ ID NO 20
<211> LENGTH: 45
<212> TYPE: DNA
<213> ORGANISM: Artificial
<220> FEATURE:
<223> OTHER INFORMATION: oligonucleotide for detection of IND-C1-EMS04
      and -WT

<400> SEQUENCE: 20
catcctcttc aatatccgga tcttctcgct tatcctttct ctact        45

```
<210> SEQ ID NO 21
<211> LENGTH: 13
<212> TYPE: DNA
<213> ORGANISM: Artificial
<220> FEATURE:
<223> OTHER INFORMATION: oligonucleotide for detection of IND-C1-EMS04

<400> SEQUENCE: 21
accgacgagc cac                                                             13

<210> SEQ ID NO 22
<211> LENGTH: 13
<212> TYPE: DNA
<213> ORGANISM: Artificial
<220> FEATURE:
<223> OTHER INFORMATION: oligonucleotide for detection of IND-C1-WT

<400> SEQUENCE: 22
gccgacgagc cac                                                             13

<210> SEQ ID NO 23
<211> LENGTH: 26
<212> TYPE: DNA
<213> ORGANISM: Artificial
<220> FEATURE:
<223> OTHER INFORMATION: oligonucleotide for detection of IND-C1-EMS08
      and -WT

<400> SEQUENCE: 23
cgtaagggta agcgaggacc cccaga                                               26

<210> SEQ ID NO 24
<211> LENGTH: 13
<212> TYPE: DNA
<213> ORGANISM: Artificial
<220> FEATURE:
<223> OTHER INFORMATION: oligonucleotide for detection of IND-C1-EMS08

<400> SEQUENCE: 24
tggtggtggc tcg                                                             13

<210> SEQ ID NO 25
<211> LENGTH: 13
<212> TYPE: DNA
<213> ORGANISM: Artificial
<220> FEATURE:
<223> OTHER INFORMATION: oligonucleotide for detection of IND-C1-WT

<400> SEQUENCE: 25
cggtggtggc tcg                                                             13

<210> SEQ ID NO 26
<211> LENGTH: 23
<212> TYPE: DNA
<213> ORGANISM: Artificial
<220> FEATURE:
<223> OTHER INFORMATION: oligonucleotide for detection of IND-C1-EMS09
      and -WT

<400> SEQUENCE: 26
cgaggacccc cagacggtgg tgt                                                  23

<210> SEQ ID NO 27
<211> LENGTH: 14
<212> TYPE: DNA
<213> ORGANISM: Artificial
<220> FEATURE:
```

```
<223> OTHER INFORMATION: oligonucleotide for detection of IND-C1-EMS09

<400> SEQUENCE: 27
actcgtcggc gtag                                                          14

<210> SEQ ID NO 28
<211> LENGTH: 12
<212> TYPE: DNA
<213> ORGANISM: Artificial
<220> FEATURE:
<223> OTHER INFORMATION: oligonucleotide for detection of IND-C1-WT

<400> SEQUENCE: 28
gctcgtcggc gt                                                            12
```